US010466152B2

(12) United States Patent
Gillette, II et al.

(10) Patent No.: US 10,466,152 B2
(45) Date of Patent: Nov. 5, 2019

(54) FLUID MONITORING AND MANAGEMENT DEVICES, FLUID MONITORING AND MANAGEMENT SYSTEMS, AND FLUID MONITORING AND MANAGEMENT METHODS

(71) Applicant: Logilube, LLC, Fort Collins, CO (US)

(72) Inventors: William J. Gillette, II, Fort Collins, CO (US); Charles E. Ogden, Laramie, WY (US); Harish Muralidhara, Laramie, WY (US)

(73) Assignee: LogiLube, LLC, Fort Collins, CO (US)

( * ) Notice: Subject to any disclaimer, the term of this patent is extended or adjusted under 35 U.S.C. 154(b) by 145 days.

(21) Appl. No.: 14/877,896

(22) Filed: Oct. 7, 2015

(65) Prior Publication Data

US 2017/0102308 A1   Apr. 13, 2017

(51) Int. Cl.

| | | |
|---|---|---|
| *G01N 11/00* | (2006.01) | |
| *G01N 33/28* | (2006.01) | |
| *G01N 33/30* | (2006.01) | |
| *G01N 1/20* | (2006.01) | |
| *G01N 11/08* | (2006.01) | |
| *F01M 11/10* | (2006.01) | |
| *F01M 11/04* | (2006.01) | |

(52) U.S. Cl.
CPC ............. *G01N 11/00* (2013.01); *F01M 11/10* (2013.01); *G01N 11/08* (2013.01); *G01N 33/2888* (2013.01); *F01M 11/04* (2013.01); *F01M 11/0458* (2013.01); *F16N 2250/08* (2013.01); *F16N 2250/36* (2013.01); *G01N 1/2035* (2013.01); *G01N 2001/2071* (2013.01); *G01N 2011/0006* (2013.01); *G01N 2011/0013* (2013.01)

(58) Field of Classification Search
CPC .............................................. G01N 2011/0006
See application file for complete search history.

(56) References Cited

U.S. PATENT DOCUMENTS

| | | | |
|---|---|---|---|
| 2,621,672 A | 12/1952 | Jacobs | |
| 3,044,860 A * | 7/1962 | Verley | ................ G01N 33/2888 |
| | | | 436/60 |
| 4,934,419 A | 6/1990 | Lamont | |
| 5,049,729 A | 9/1991 | Dease | |
| 5,303,163 A | 4/1994 | Ebaugh | |
| 5,464,883 A | 11/1995 | Sharma | |
| 5,928,291 A | 7/1999 | Jenkins | |

(Continued)

FOREIGN PATENT DOCUMENTS

WO    WO 2011/102129    8/2011

OTHER PUBLICATIONS

WO PCT/US16/54722 Srch Rpt, dated Feb. 6, 2017, LogiLube, LLC (Continued)

*Primary Examiner* — Herbert K Roberts
(74) *Attorney, Agent, or Firm* — Wells St. John P.s.

(57) ABSTRACT

A fluid monitoring and management device that includes a housing with a fluid passageway. The fluid monitoring and management device further includes a fluid property sensor with a sensing element in the fluid passageway. A valve is in the fluid passageway of the fluid monitoring and management device. A removable bottle mount is aligned with the valve to be selectively in fluid communication with the fluid passageway.

41 Claims, 29 Drawing Sheets

(56) References Cited

U.S. PATENT DOCUMENTS

| | | |
|---|---|---|
| 6,253,129 B1 | 6/2001 | Jenkins |
| 6,575,018 B2 | 6/2003 | Berndorfer et al. |
| 6,625,539 B1 | 9/2003 | Kittell |
| 6,629,029 B1 | 9/2003 | Giles |
| 6,741,938 B2 | 5/2004 | Berndorfer |
| 6,826,460 B2 | 11/2004 | Kittell |
| 6,899,151 B1 | 5/2005 | Latka |
| 7,072,775 B2 | 7/2006 | Hemp |
| 7,822,576 B2 | 10/2010 | Flint |
| 7,899,591 B2 | 3/2011 | Shah |
| 8,416,067 B2 | 4/2013 | Davidson |
| 8,666,586 B2 | 3/2014 | Portocalis |
| 8,831,825 B2 | 9/2014 | Shah |
| 8,843,269 B2 | 9/2014 | Anderson |
| 8,896,430 B2 | 11/2014 | Davidson |
| 8,928,473 B2 | 1/2015 | Gilchrist |
| 9,041,548 B2 | 5/2015 | Portocalis |
| 9,080,529 B1 | 7/2015 | Klughart |
| 9,233,828 B2 | 1/2016 | Portocalis |
| 9,324,198 B2 | 4/2016 | Davidson |
| 9,407,105 B2 | 8/2016 | Hyde |
| 9,418,557 B2 | 8/2016 | Kawamata |
| 2003/0222656 A1* | 12/2003 | Phillips .......... G01N 27/02 324/605 |
| 2004/0259189 A1* | 12/2004 | Marschke .......... G01N 1/14 435/34 |
| 2005/0270525 A1 | 12/2005 | Susko |
| 2007/0240649 A1 | 10/2007 | Freeman |
| 2008/0202255 A1 | 8/2008 | Albrecht |
| 2008/0223114 A1* | 9/2008 | Albertson .......... G01N 33/2888 73/54.07 |
| 2010/0199758 A1 | 8/2010 | Tokhtuev |
| 2011/0307160 A1 | 12/2011 | Verdegan |
| 2013/0298642 A1 | 11/2013 | Gillette |
| 2013/0298664 A1 | 11/2013 | Gillette |
| 2013/0298857 A1 | 11/2013 | Gillette |
| 2013/0300341 A1 | 11/2013 | Gillette |
| 2013/0301674 A1 | 11/2013 | Gillette |
| 2013/0304351 A1 | 11/2013 | Gillette |
| 2013/0304385 A1 | 11/2013 | Gillette |
| 2014/0266065 A1* | 9/2014 | Von Herzen .......... G01N 33/2888 320/137 |
| 2016/0003756 A1* | 1/2016 | Suzuki .......... G01N 27/06 210/767 |
| 2016/0033465 A1* | 2/2016 | Schreiber .......... G01N 35/00732 702/50 |
| 2018/0173213 A1 | 6/2018 | Bendert |

OTHER PUBLICATIONS

WO PCT/US16/54722 Wtn Opn, dated Feb. 6, 2017, LogiLube, LLC
WO PCT/US16/57994 Srch Rpt., dated Jan. 9, 2017, Gillette.
WO PCT/US16/57994 Wtn Opn., dated Jan. 9, 2017, Gillette.
Aghayan, et al. "On-Line Monitoring of Engine Health Through the Analysis of Contaminants in Engine Lubricant", Graduate Program in Mechanical & Material Engineering, 2012, pp. I-254.
Agoston et al., "Viscosity sensors for engine oil condition monitoring—Application and interpretation of results", Elsevier, Sensors and Actuators A 121, Netherlands, 2005, pp. 327-332.
Bennett, et al., New Solid State Oil Condition Sensor for Real Time Engine Oil Condition Monitoring, SAE international, 06AE-210, United States, 2005, 8 pgs.
Carey, et al., "The Dielectric Constant and Oil Analysis", Machinery Lubrication Publitation, Noria Corp., United States, 2015, pp. 1-3.
Dobrinski, et al., "Combi-sensor for Oil Level and Oil Qualify Management", SAE Technical Paper Series 2008-01-0906, United States, 2008, 15 pgs.
Dobrinski, et al., "Combi-sensor for Oil Level and Oil Quality Management", SAE International Paper 2008-01-0906, United States, 2008, 1 pg.
Milpied, et al., "Applications of tuning fork resonators for engine oil, fuel, biodiesei fuel and urea quality monitoring", SAE International, United States, 2009, 9 pgs.
Uhrich "Experiment conditions", SAE Technical Papers, United States, 2009, 1 pg.
Uhrich, "Figure 8: Impact of water addition on 10W40 oil dielectric constant", SEA Technical Papers, United States, 2009, 1 pg.
Zhu, et al., "Lubrication Oil Condition Monitoring and Remaining Useful Life Prediction with Particle Filtering", International Journal of Prognostics and Health Management, United States, 2013, pp. 1-15.
Zhu, et al., "Survey of Lubrication Oil Condition Monitoring, Diagnostics, and Prognostics Techniques and Systems", Journal of Chemical Science and Technology, vol. 2, Iss. 3, United States, 2013, pp. 100-115.
WO PCT/US16/57994 IPRP, dated Apr. 24, 2018, Gillette.
WO PCT/US16/54722 IPRP, dated Apr. 10, 2018, LogiLube, LLC.

\* cited by examiner

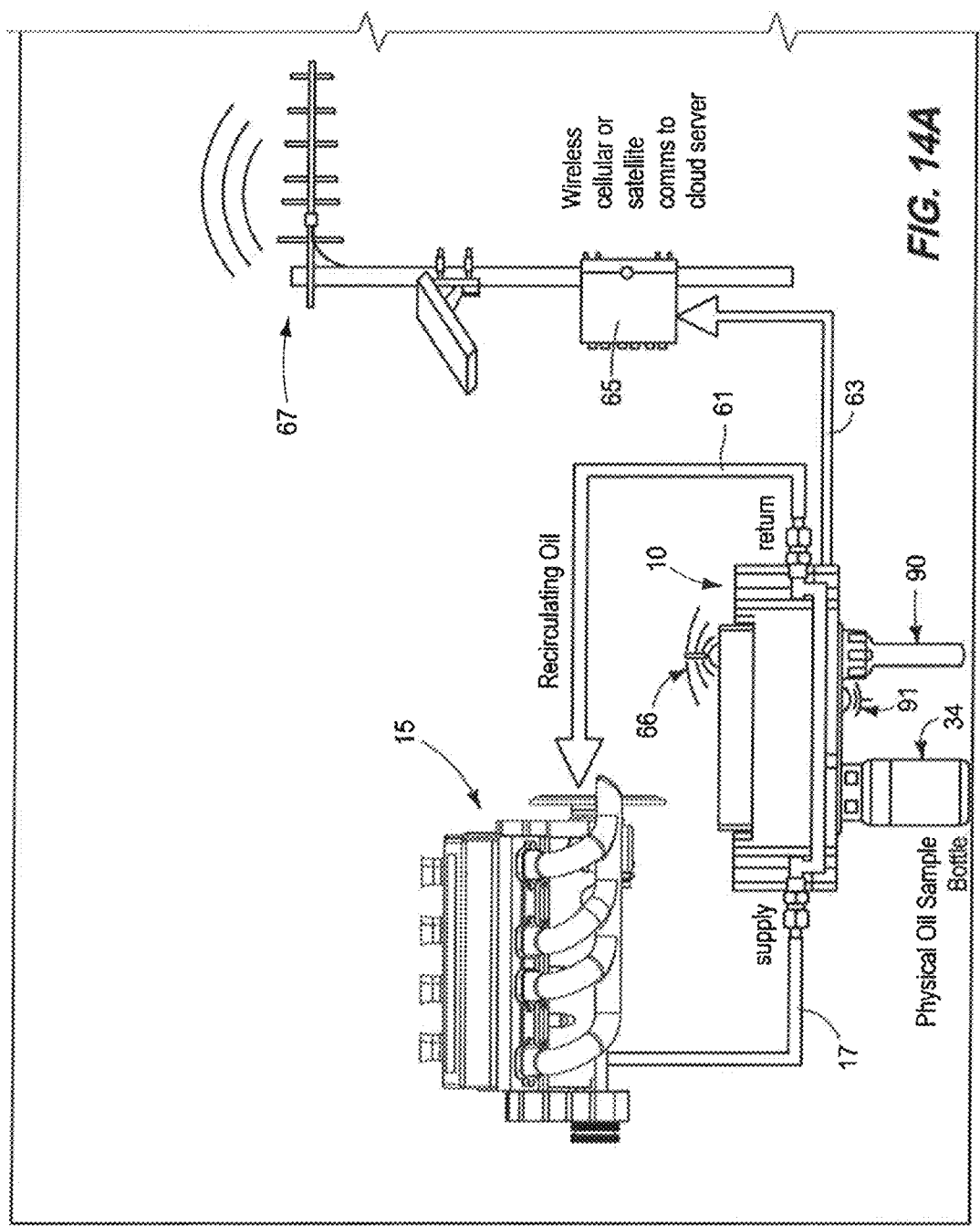

FLUID MONITORING AND MANAGEMENT DEVICES, FLUID MONITORING AND MANAGEMENT SYSTEMS, AND FLUID MONITORING AND MANAGEMENT METHODS

CROSS REFERENCE TO RELATED APPLICATION

This application does not claim priority from any other application.

TECHNICAL FIELD

The subject matter of this application relates to fluid monitoring and management devices, systems and methods.

BACKGROUND OF THE DISCLOSURE

Fluids and liquids are the "life blood" of equipment and machinery having moving components. How goes the fluids/liquids, goes the equipment/machinery. That is, the health of the equipment/machinery depends on the fluids/liquids. Exemplary fluids/liquids utilized in equipment/machinery include fuel (i.e. diesel, kerosene, gasoline, etc.); fluid lubricants such as grease and oil; coolants such as glycol and water; and process fluids such as hydraulic fluid.

Consider an internal combustion engine in an automobile. Engine fuel is the liquid that powers the engine to drive the automobile. Engine coolant is a fluid that flows through the engine to prevent overheating. Engine oil and transmission fluid are the lubricants that reduce wear on moving parts; clean and inhibit corrosion; improve sealing actions; and further cool the engine and transmission, respectively. Hydraulic fluid is the medium for transferring power or action between respective systems, such as, from steering wheel to road wheels (power-assisted steering system) and from brake pedal to brake pads, etc.

If the "health" of any one of these fluids is compromised or diminished, the "health" of the engine and/or automobile is compromised or diminished which ultimately can lead to a catastrophic failure of the engine or automobile. Consequently, there always is a need for improved fluid monitoring and management devices, systems and methods to predict and prevent diminishing health of the fluids, and correspondingly, the equipment and machines that the fluids protect.

While the subject matter of this application was motivated in addressing issues of fluids, it is in no way so limited. The disclosure is only limited by the accompanying claims as literally worded, without interpretative or other limiting reference to the specification, and in accordance with the doctrine of equivalents.

Other aspects and implementations are contemplated.

BRIEF DESCRIPTION OF THE DRAWINGS

Exemplary embodiments of the various disclosures are described below with reference to the following accompanying drawings. The drawings may be considered to represent scale.

FIGS. 14A and 14B are schematic views of an exemplary fluid monitoring and management system according to one of various embodiments of the invention including the fluid monitoring and management device of FIG. 1.

DETAILED DESCRIPTION OF THE EMBODIMENTS

Figure 1:
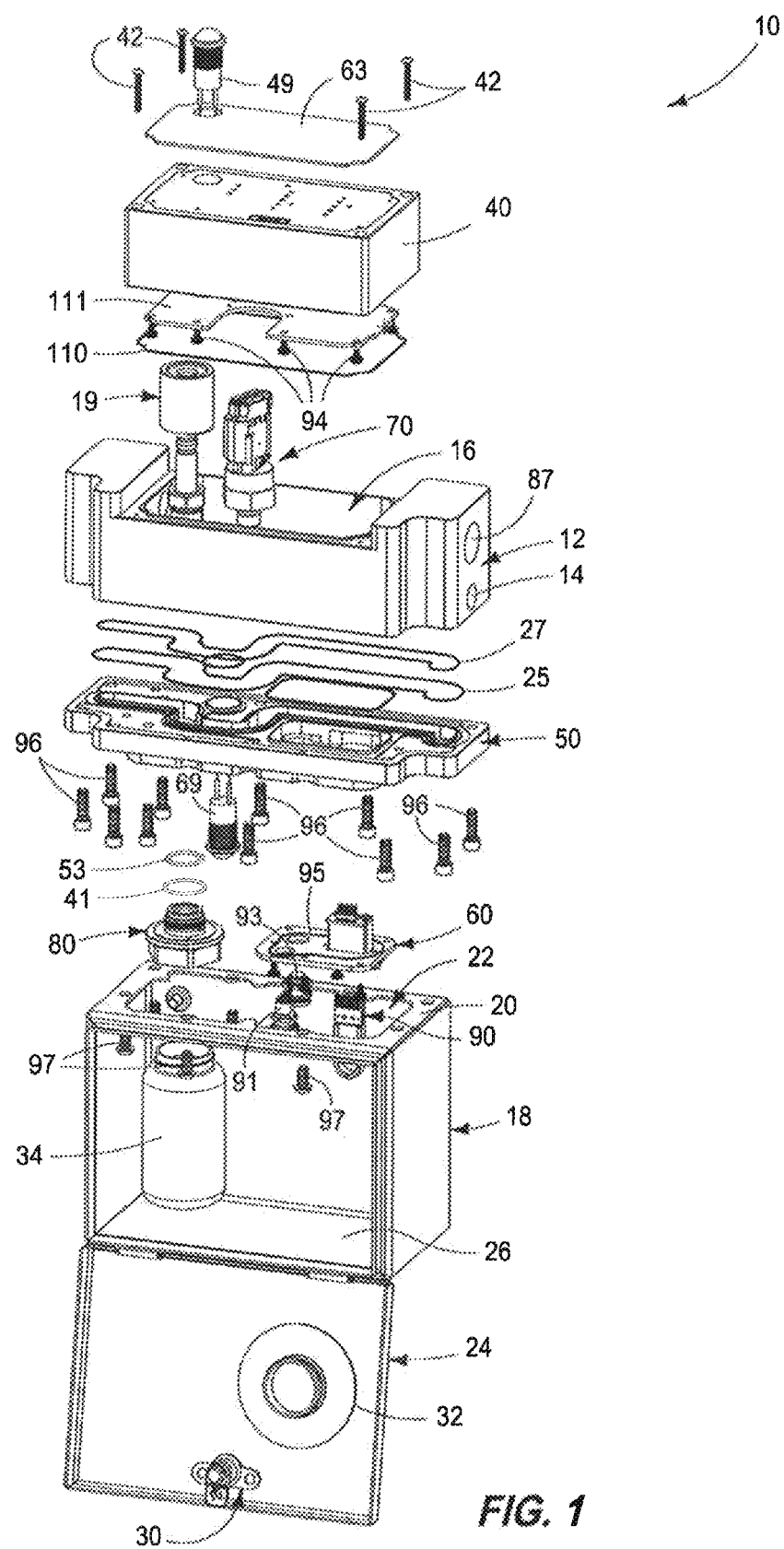
FIG. 1 is an exploded view of an exemplary fluid monitoring and management device of an exemplary fluid monitoring and management system (collectively fluid device/system) according to one of various embodiments of the invention.

This disclosure is submitted in furtherance of the constitutional purposes of the U.S. Patent Laws "to promote the progress of science and useful arts" (Article 1, Section 8).

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one."

The inventive fluid monitoring and management devices, systems, and methods disclosed in this application include a technology platform, data analytics, and fluid quality analysis services that, when combined or used separately, provide real-time condition monitoring and intelligent health perspective of equipment (and/or machines, machinery) that utilizes liquids (fluids) discussed previously (again, such as fuel (i.e. diesel, kerosene, gasoline, etc.), fluid lubricants such as grease and oil, coolants such as glycol and water, and process fluids such as hydraulic fluid, etc.). It should be understood that any reference in this document to any variation of fluid monitoring and management devices, systems, and methods such as "fluid devices," "fluid systems," or "fluid methods" are all inclusive and applicable to the same concept.

Consider one specific use: intelligent health and real-time condition monitoring of lubricants (e.g. lubricating oil) for processing compressor packages (compressor & engine) utilized in the global on-shore/off-shore oil & gas industry.

Since the beginning of the modern industrial revolution, use of lubricants (e.g. lubricating oil) has provided the necessary function of reducing friction and heat from the moving/sliding parts of mechanical equipment. In reciprocating equipment with rotating shafts such as internal combustion (IC) engines and compressors, synthetic, partially synthetic or hydrocarbon-based oil is used to reduce the friction (lowering the heat) and carry away tiny wear metal particles from the mating interface of internal mechanical components such as piston rings & cylinder walls, valve stems and valve guide bearings, crankshaft journals and corresponding bearings, meshed gear teeth, cam shaft lobes and cam followers, etc.

The enemy for this essential lubricating oil tasked with keeping the mechanical parts generously lubricated is heat. As the oil heats up from excess friction and/or inadequate cooling of the mechanical equipment, the oil base-stock will begin to oxidize and breakdown causing the fluid to become acidic in nature, thus promoting corrosion of the metal parts the lubricating oil is supposed to protect. Fuel dilution from "blow-by" in the combustion chamber of an IC engine is another culprit that can degrade the integrity of engine oil. As the piston rings wear from constant reciprocating movement and friction against the mating cylinder walls, the raw fuel from the compression stroke, as well as combustion gases from the ignition & exhaust stroke (ref. Otto cycle), can slip by the piston rings and enter the crankcase containing the engine oil reservoir. Hence, the lighter hydrocarbon (fuel) will dilute the thicker lubricating oil, compromising the ability to provide adequate lubrication of the mechanical parts.

Moreover, the dynamic viscosity of the oil (measure of how thin or thick the fluid is, value of one centipoise (1 cP) being that of water) is an engineered property that provides the oil with specific flow, lubrication, and surface adhesion characteristics which are essential to be maintained in order to facilitate proper lubrication of the moving/sliding parts, even under the harshest of operating conditions, for example, heat and shear. As the oil breaks down due to excess heat, it oxidizes, thus increasing the viscosity (making the oil thicker).

Degraded oil with a higher viscosity loses the ability to properly flow throughout the small passages and tolerances between the moving/sliding surfaces thus compromising the ability to remove the heat of friction. This condition leads to higher metal wear stemming from surface-to-surface abrasion, increasing the particulate contaminant load of material constituents such as copper, iron, silicon, manganese, nickel, cobalt, molybdenum, etc. Proper equipment lubrication systems are designed to carry away the wear metal particulate contaminants by recirculating the oil flow under pressure via flow-through filtration elements and size-exclusion based on the diameter of the targeted particulate size.

Alternatively, as the oil is exposed to excessive shear forces, molecules will break down causing the viscosity to decrease. This "thin" oil is unable to properly cushion the moving/sliding metal surfaces and the likelihood of metal-metal contact within the engine increases. If there is metal-metal wear present in an engine, there will be a great deal of friction and heat generated at the point of contact, severely reducing the life of the affected components. Wear-metal generation will also increase which contributes substantially to the abrasive contaminant loading in the lubricating oil.

Manufacturers of engineered lubricating oils fortify the oil by blending it with "additives" to extend the operating life of the oil while also increasing the range of harsh conditions the oil can be used under; the goal is to develop an oil that can be used in more abusive conditions and run longer between oil change intervals. Increasing the "alkalinity reserve" of the oil (as measured by the Total Base Number in units of mg KOH/gm) extends the length of time the oil can be used before the oxidation and nitration of the oil turns it into a more acidic fluid. The measurement of the oil acidity is determined by the amount of potassium hydroxide (in mg) that is needed to neutralize the acids in one gram of oil. Total Acid Number (TAN) in mg KOH/gm is an important characteristic that determines the useful life of the oil. A lower TAN indicates that the oil exhibits higher acidity and is nearing end of useful life.

A typical additive package ("add-pack") contains detergents such as calcium, magnesium, oxidation inhibitors such as sulfur, and natural metal lubricating agents such as zinc and phosphorus. The lubricating oil used in an IC engine finds its way into the combustion chamber and is "consumed," or burned along with the fuel and then expelled via the exhaust system. When burned in the combustion chamber, the add-pack constituents blended in with the oil base-stock produce an ash deposit on the interior surfaces of the combustion chamber and exhaust valve surfaces. These ash deposits are combustion by-products that are the result of burning fuel and engine oil during the engine's normal operation. Such deposits are in the form of small (>4 micron), hard particulates that have the capacity to contaminate the recirculating engine oil. The engine oil, contaminated with tiny, abrasive particles will severely damage the engine components if unfiltered and left unchecked. This excessive wear condition can lead to a dramatically reduced equipment life and operating efficiency.

An exemplary embodiment of the inventive fluid monitoring and management devices, systems and methods can be deployed, as one non-limiting example, in the Oil & Gas industry, specifically in the Midstream market focused on providing intelligent equipment health condition monitoring of rotating equipment such as, but not limited to, reciprocating compressors and internal combustion engines.

Non-limiting applications for the inventive fluid monitoring and management devices, systems and methods include: a) natural gas gathering and compression application, compressor package comprised of a natural gas-fired internal combustion engine powering a reciprocating multi-stage compressor; b) monitoring the oil quality and consumption of the primary oil lubricating system for the driver (IC engine), i.e. engine crankcase, valve train, and piston lubrication, turbo lubrication; c) Monitoring the oil quality and consumption rate of the crankcase lubricating oil system for the compressor; d) Monitoring the oil quality and consumption rate of the high-pressure cylinder lubricating oil system for the compressor; e) in situ monitoring of oil quality and consumption; and f) scheduled (routine) and exception-based oil sample collection wherein oil samples are collected via an automated solenoid actuated valve driven by a microprocessor controlled autonomous algorithm thereby eliminating the human interface (exception-based rules are unique and based on custom algorithm that determines a 'dangerous condition' event or threshold has been detected).

Inventive fluid monitoring and management methods include, as xnon-limiting examples only, using the fluid devices and systems to collect fluid samples via an automated solenoid actuated valve driven by a microprocessor controlled autonomous algorithm, thereby eliminating the human interface. Exception-based rules in the algorithm determine that a "dangerous condition" detected or that a threshold value has been reached or surpassed. Moreover, fluid (oil) sample analysis can be provided by a third party lab utilizing industry recognized ASTM protocols.

Referring to FIGS. 1-13, an exemplary, non-limiting embodiment of an inventive fluid monitoring and management device 10 (hereinafter most often stated as "fluid device" for simplicity and can be considered one of various exemplary embodiments of a fluid system 120) is described. It should be understood that FIG. 1 is representative of one, non-limiting example, of an exploded view of the fluid device 10 with additional FIGS. 2-13 more readily illustrating various aspects of specific components of fluid device 10. It should be further understood that fluid device 10 described throughout this document is applicable to monitor and manage the utilization of any fluid in any equipment, apparatus and/or machine. However, the focus of the following description of the fluid device 10 (and fluid monitoring and management systems and methods) is directed to, as only one of various possible embodiments, as being utilized with a fluid such as a lubricant, and more specifically, to oil circulating through an engine.

Fluid Device

Referring to FIG. 1, an overview of the major components of the fluid device 10 is first summarily presented to facilitate a more thorough subsequent discussion of the components. A bezel 63 is secured in a recess in a lid 40. Lid 40 houses a printed circuit board assembly 111 (PCBA) and a weatherproof seal 110 is provided over the PCBA 111 in the lid 40. Lid 40 is secured over an opening 16 in an upper housing 12. Upper housing 12 receives in opening 16 a solenoid valve cartridge assembly 19 (solenoid or solenoid cartridge) and a sensor package 70. Sensor package 70 includes a fluid property sensor and a fluid pressure sensor. A lower housing 50 is secured to upper housing 12 with various seals 25/27 in between. A sample collection housing 18 is secured to the lower housing 50. The sample collection housing 18 encloses (houses) sampling bottle 34 (sample bottle), sample bottle mount 80 (bottle mount) and user interface plate assembly 60 (user interface panel). Secured to user interface panel 60 is a removable flash data storage key 90, a reset button 91 and a data/configuration port 93. A door 24 is pivotably secured to sample collection housing 18 wherein the door 24 has a latch 30 and a sample bottle cap 32. Bezel 63 and lower housing 50 each have a light-emitting diode (LED) 49 and 69 respectively. Bottle mount 80 has two o-rings 41/53 and various fasteners 42/94/96/97 secure various components of the fluid device 10 together.

The exemplary fluid device 10 has a body construction (main housing) that includes an upper housing 12 removably secured to a lower housing 50. An exemplary body (upper and lower housings) 12/50 is the main structure of the fluid device 10 and ultimately supports additional structures and is used to attach and mount the fluid device 10 to subject equipment being investigated for oil usage (for example, engine and/or compressor). The body 12/50 is the mount and protection for sensors from damage, as well as sealing structures for the constant flow of fluid (oil) from the engine and/or compressor through the fluid device 10. The body 12/50 also provides for weathertight/explosion-proof conduit connections for power supply and data signal wires.

Still further, processed data from a microprocessor exits the body 12/50 via wires and is transmitted back to a Data Aggregator/Communications Hub (optional wireless connectivity). The body 12/50 is a computer numerical control (CNC) machined aluminum multi-part housing that forms the structural element designed to be sufficiently strong to withstand the rigors of abusive environment typical of oil & gas industry.

Moreover, the fluid device 10 is designed to operate equally well indoors as well as outdoors and includes generally a six (6) main pieces/components in the design which are more thoroughly described subsequently: main Upper Housing 12, Lower Housing 50, User Interface Plate Assembly 60 (or User Interface Panel), Sample (sampling) Bottle Mount 80 and Lid 40.

An exemplary upper housing 12 (sensor housing) of fluid device 10 forms the main housing component body 12/50 and secures/attaches the fluid device 10 to subject equipment with an equipment-specific, load bearing, vibration-isolating bracket. An exemplary bracket is attached via fasteners (threaded bolts) that thread into drilled and tapped holes in the metal upper housing 12. Proper torque setting of the bracket screw fasteners in an interface of upper housing 12 overcomes the likelihood of loosening of the fasteners as the fluid device 10 is subjected to constant vibration during normal operation.

Figure 2:
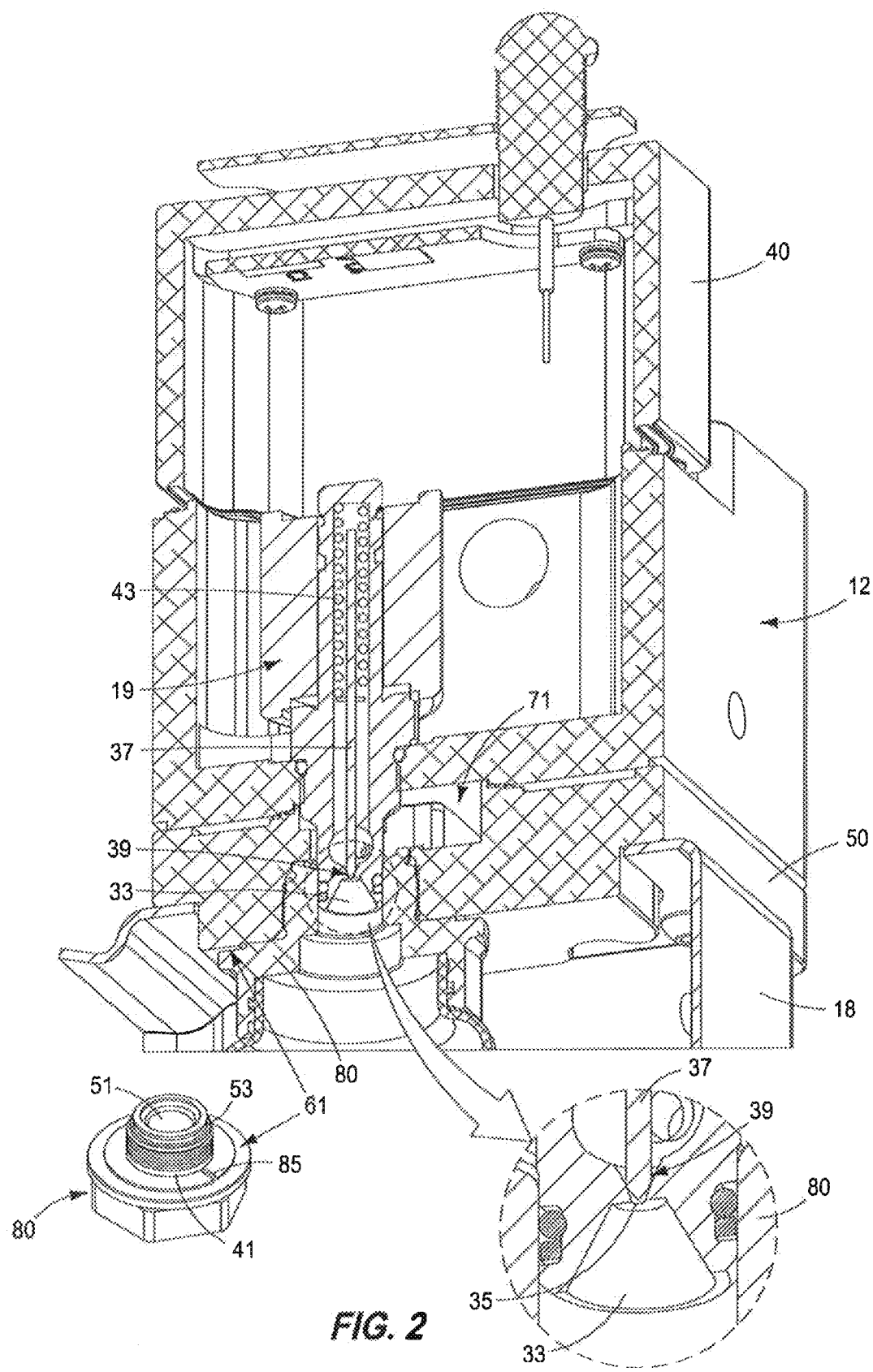
FIG. 2 is a partial sectional and partial cutaway of the fluid device/system of FIG. 1.

Upper housing 12 has an opening 16 through a top portion of the structure that terminates at a lower surface 17 (FIG. 2). In situ sensor bodies, for example, fluid property sensor 70 (and pressure sensor) and solenoid assembly 19, are threaded into the lower surface 17 of upper housing 12. In one embodiment, upper housing 12 is made from CNC machined solid billet aluminum. Alternatively, upper housing 12 is made from near-net shape investment cast aluminum with secondary CNC machining operations to provide tight tolerance features. Upper housing 12 has a detailed seal gland design that provides for the provision of weatherproof high-reliability sealing at interface between lid 40 and upper housing 12. Tapped holes (openings) 87 (only one shown in FIG. 1) (NPT or Machine Thread with o-ring boss seal) on opposing sides (left and right) of the upper housing 12 facilitate installation of inlet and outlet oil line (SS Swagelok™ fittings) in support of leak-free recirculating oil flow to and from the engine. In one embodiment, upper housing 12 is installed such that an oil path is horizontal and level to facilitate a fluid (oil) sampling. Another opening (hole) in side of upper housing will have/receive electrical conduits for electrical/data communication with electronics of fluid device/system 10/120, for example, a printed circuit board assembly (PCBA) 111.

In one non-limiting example, engine oil is supplied from a high-pressure engine oil pump that is plumbed from an engine block (for example, gallery ports) to upper housing 12 via SS tubing. An oil return line is from the upper housing 12 to the engine oil sump (at near-atmospheric pressure, 0-1 psig) and plumbed from fluid device 10 to engine crankcase via SS tubing. Since there is a high pressure differential across the length of the upper housing 12 (between the oil supply~60 psig, and oil return~atmospheric, 0 psig), a provision has been made for a removable, machined threaded orifice plate in the oil exit side of the upper housing 12. This orifice feature will allow for maximizing the pressure drop across the fluid device 10 by reducing the oil flowrate through the upper housing 12. Hence, the measured oil pressure within the oil line can be managed so that the measured pressure is closer to the operating pressure of the engine.

Alternatively, an engineered orifice opening can be machined into the oil exit port as an integral feature of the upper housing 12. In one embodiment, a variable orifice would be incorporated to provide the capability of varying orifice diameters for the purposes of fine tuning the oil flow rate vs. oil pressure differential balance. In one embodiment, the fluid device 10 is mounted to maximize the oil supply flowrate available to the upper housing 12 and fluid device 10.

An exemplary dimensional length of the upper housing 12 is such that the in situ (in-line) sensors can be arrayed in a manner that they conveniently fall within the path of the integral oil line. Should there be a need for additional in situ sensors, and/or solenoid actuated valve bodies, the length of the upper housing 12 can be increased appropriately. The dimensions of mating lower housing 50 and lid 40 would correspondingly increase in dimensions to match.

Fluid device 10 further includes a lid 40 that is a housing component removably secured/affixed to the top of upper housing 12 via tamper-resistant fasteners or screws 42 (in support of "intrinsically safe" design practices). When assembled, the upper housing/lower housing/lid 12/50/40 sub-assembly form a weather-tight, IP67 rated, intrinsically safe enclosure housing the sensitive electronics and sensors for fluid device 10.

All aluminum outer surfaces of the fluid device 10 are finished with a baked "Safety Orange" ceramic coating (Cerakote®) to provide extremely tough, abrasion resistant surface to protect the lid 40 from rigors of the Oil & Gas environment. For offshore applications that are exposed to open water, salt water spray, and the worst of inclement weather, the ceramic coating provides the lid 40 with an excellent and superior finish.

As stated previously, an exemplary fluid device 10 includes the lower housing 50 removably secured to the upper housing 12. The lower housing 50 forms substantially a portion of the oil flow path that enters and exits the upper housing 12 from the engine. The lower housing 50 establishes the oil flow path bottom and sides which is engineered specifically to provide consistent and high quality oil samples and sensor readings. Furthermore, lower housing 50 allows for the connection of the oil sample bottle mount and the protective sampling enclosure. The lower housing 50 additionally contains the mounting location for the removable User Interface Panel (plate) 60.

The oil flow path for the fluid device 10 is designed so that the in situ fluid property sensor 70 (FPS) is constantly able to produce measurements that are representative of the oil flowing through the fluid device 10 at any given time. These measurements are highly repeatable and are accurate. In order to maintain high quality sensor data over the life of the fluid device 10, the oil flow path is designed with features that promote scouring of the sensor elements (sensing elements) through the creation of intensely turbulent zones of oil flow around the in situ sensor elements (described and shown more thoroughly subsequently). This self-scouring feature eliminates the need for regular cleaning or replacement of the fluid property sensor 70 and ensures that quality data will always be produced.

It should be understood that in one embodiment, a representative fluid property sensor can be purchased from Measurement Specialties™ having an internet address of www.meas-spec.com. A specific representative fluid property sensor is listed as FPS2800B12C4-Fluid Property Sensor Module.

Referring to FIG. 1 and more specifically to FIG. 2, the fluid device 10 includes a solenoid assembly 19 to allow oil to exit the flow path and fill a sampling bottle (sample bottle) 34 as needed or indicated by fluid device 10. The solenoid assembly 19 comprises a electromagnetic coil 43 surrounding a solenoid actuated needle 37, and a needle valve 39 (solenoid needle valve or valve needle) including a sampling orifice 35. The solenoid assembly 19 is designed for ultra-high pressure applications. The sampling orifice 35 is positioned above a sampling valve body 33. At lower pressures, for example less than 150 psi (<150 psi), the solenoid assembly 19 exhibits a leak rate that is effectively zero. This means that the solenoid assembly 19 will not drip into the sampling bottle 34, and therefore, is either on or off. In one embodiment, the operational pressure range for the solenoid 19 actuated valve is from about 5 psi to about 150 psi.

Still referring to FIG. 1 and FIG. 2, the fluid device 10 includes a sample bottle mount 80 (also bottle mount) that is interchangeable to accommodate different sample bottle collection geometries. In one embodiment, an oil sample collection is a 4.2-oz. (125 mL) clear plastic (PET) wide-mouth bottle that has a thread and a twist-on sealing screw cap with a thread size defined as 38-400. For an exemplary oil sample analyses which includes a standard set of ASTM protocol tests, the sample volume required is 4.2-oz. However, if a more extensive set of oil analyses to be performed is desired, a larger volume of oil may be required wherein a larger 8-oz. sized PET bottle can be used. In the instance where the larger bottle may have a larger bottle mouth, or possibly have a screw thread that is different than the 4.2-oz. bottle, the fluid device 10 accommodates different bottle mouth/thread geometries.

The interchangeable sample bottle mount 80 (bottle mount) threads onto the underside of the lower housing 50, and while in the fluid device 10, is in a co-axial orientation/configuration with the needle valve 39. The bottle mount 80 is a precision-machined metal part that when threaded onto the lower housing 50, mates up to a machined flat surface that forms a seal and land area for a shoulder of the needle valve 39. The bottle mount 80 has valve body mating surface 51 and a small vent orifice 85 (tiny pinhole vent (vent hole) that allows oil/air to escape from inside the sample bottle 34 during an oil sample collection event. Moreover, the bottle mount 80 has geometry features (i.e. flats, hex, spanner slots, etc.) that allow for a tool to be used to install the bottle mount 80 to the lower housing 50 and apply the appropriate amount of torque to insure the bottle mount 80 will not loosen during exposure to constant vibration.

The sample bottle mount 80 is aluminum and is designed to form the lower body of the sampling valve and the oil flow path sealing surface. The bottle mount 80 includes the tiny pinhole vent (vent hole) 85 to allow oil/air to escape during an oil fill event. The vent 85 is recessed near the threads of the bottle mount 80 to prevent contamination such as from dust. Contamination prevention maintains a sterile oil sample bottle 34 to ensure that contamination does not bias or influence ultimate oil analysis results. The bottle mount 80 is designed with a stepped shoulder to receive a felt pad 61 so that the felt pad 61 can be installed between the lower housing 50 and the bottle mount 80. The felt pad 61 acts as an air filtration mechanism for the vent hole 85. In one embodiment, the bottle mount 80 has a large hex head to facilitate gripping with a wrench for easy removal. In one embodiment, the bottle mount 80 has a thread pattern 1-32 UN for installation in the lower housing 50 that ensures a reliable, high quality seal.

Mating threads on the bottle mount 80 for securing the sample bottle 34 are designed/configured to be slightly undersized to squeeze the sample bottle threads and create a strong friction fit. Furthermore, this thread configuration is designed to prevent loosening of the sample bottle 34 due to the effects of vibration and high temperatures over time.

Since the bottle mount 80 establishes the lower valve housing and a portion of the oil flow path, the bottle mount 80 is sealed with redundant o-rings 41 and 53. A first o-ring 41 is located at the base of the threads (from FIG. 2 view) of the bottle mount 80 near or adjacent the bottom surface of the lower housing 50. A second o-ring 53 is located near the top or terminal end of the threads (from FIG. 2 view) of the bottle mount 80. The second o-ring 53 is sized to protect the female 1-32 UN threads in the lower housing 50 from being damaged during installation, replacement, or removal of the bottle mount 80. Additionally, this reduces the risk of damage to the threads of the bottle mount 80 during installation, particularly during low light or blind installation situations which can be common in the field. The bottle mount 80 can accommodate sample bottle 34 size and bottle neck thread configuration, male or female. The bottle mount 80 is field changeable so that sampling bottle 80 type can be modified at any time in the field.

In one embodiment of the fluid device 10, the bottle mount 80 includes a switch actuation mechanism that allows the fluid device 10 to detect the presence of a sampling bottle 34. One embodiment of a switch actuation mechanism includes a push rod that is interfaced to a pushbutton switch in the fluid device 10. The presence of a sampling bottle 34 results in a lifting action on the pushrod to activate the pushbutton switch. Another embodiment of a switch actuation mechanism uses a magnetic disk that is lifted with the installation of a sampling bottle 34 which in turn activates a reed switch located inside the upper housing 12 of the fluid device 10.

The fluid device 10 can use a pressure transducer instead of the vent hole 85 of the bottle mount 80 to determine if the sampling bottle 80 is full of oil. In this design, the sampling bottle 80 is airtight during a sampling event and as the oil fills the volume of the sampling bottle 80, the oil will displace the air in the sampling bottle 80 causing a rise in air pressure until a threshold pressure is reached indicating an oil sample is collected.

Figure 3A:
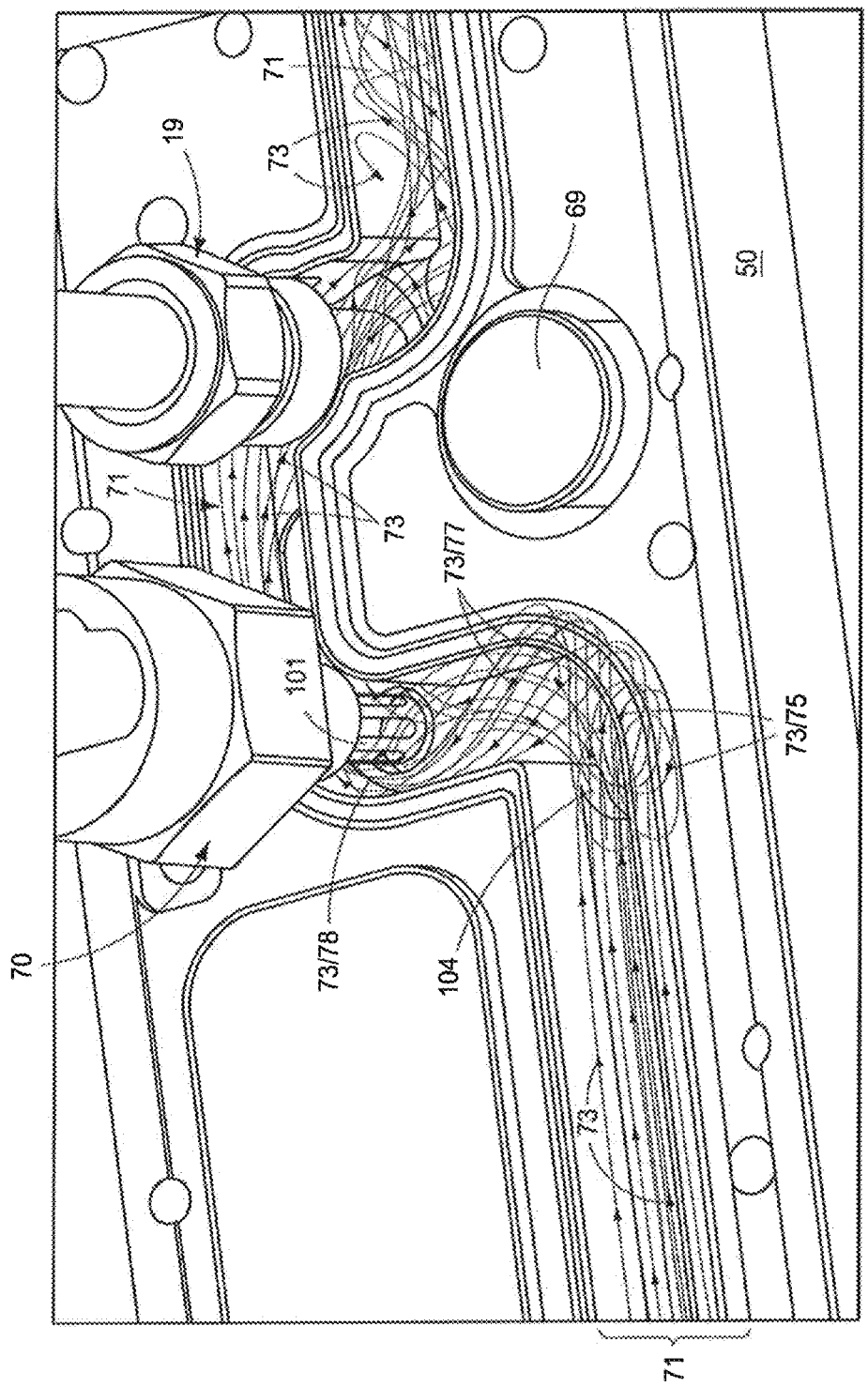
FIGS. 3A, 3B, 3C and 3D are different perspectives of partial sectionals of the fluid device/system of FIG. 1 illustrating exemplary fluid flows.
Figure 3B:
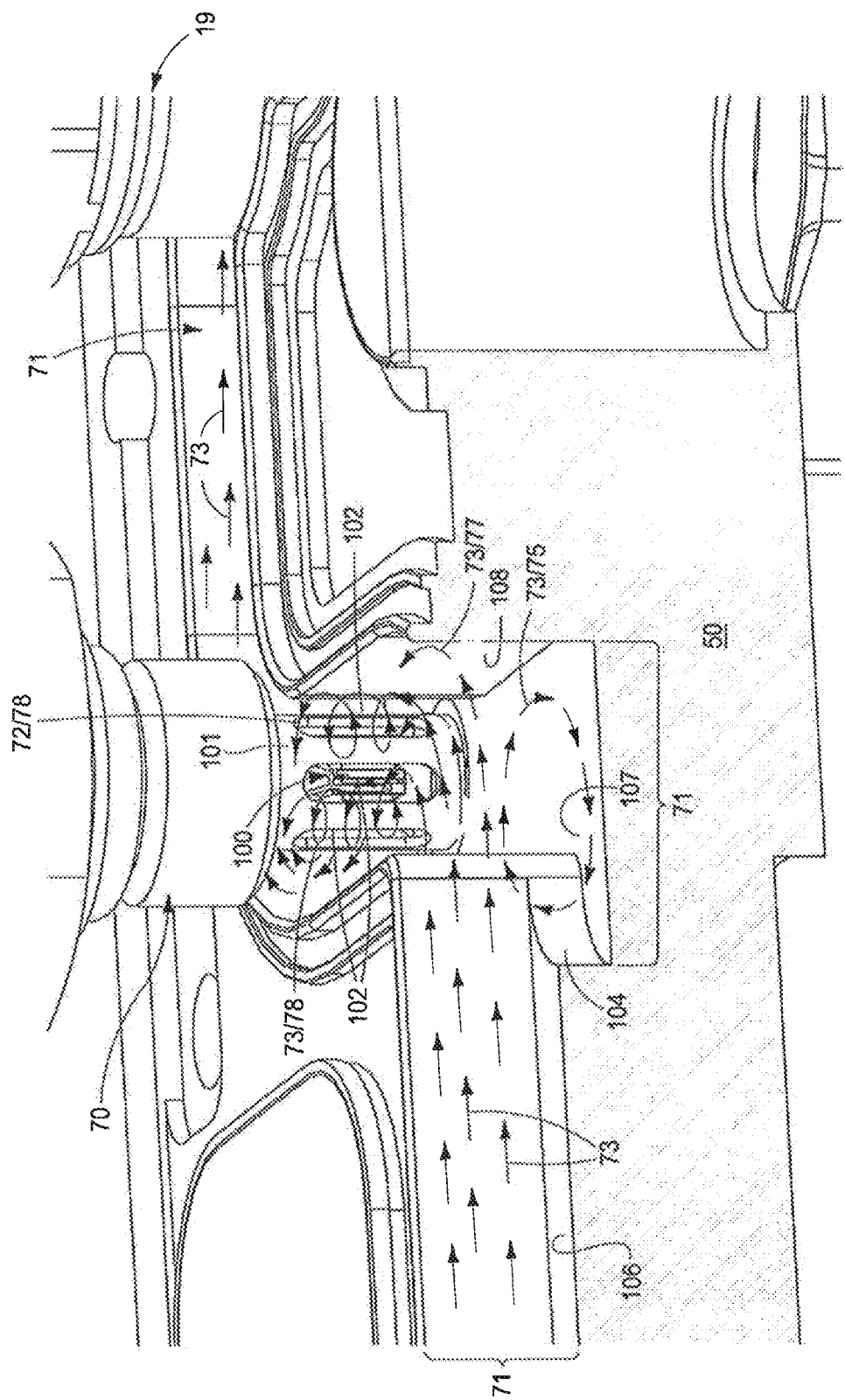

Referring to FIGS. 3A and 3B (and FIGS. 3C and 3D subsequently described), a sectional of the lower housing 50 of the fluid device 10 is illustrated and exposes a portion of a fluid property sensor 70 in a portion of a fluid passageway 71 (pathway, passage, path, or circuit, flow path). The fluid passageway 71 of fluid device 10 is designed so that the in situ fluid property sensor 70 and the solenoid assembly 19, respectively, are consistently able to produce accurate measurements and oil samples that are representative of the oil flowing through the fluid device 10 at any given time. The data produced from oil samples by the fluid device 10 and from any lab analysis are required to be of the highest quality and repeatability. The fluid device 10 uses high speed flows as well as a strategically located square change (sharp square steps 104 and 105 (see FIG. 9)) in floor depth of the fluid passageway 71 to create a phenomenon known as a "Hydraulic Jump" in the flow of the fluid. This condition ensures that turbulence and mixing of oil is maximized in the fluid flow through the fluid passageway 71 proximate to the fluid property sensor 70 and solenoid 19.

Still referring to FIGS. 3A and 3B, oil flow (fluid flow) 73 moves from left to right in this view. A sensor element (sensing element) 100 of the fluid property sensor 70 is mounted in a protective cage 101. Protective cage 101 has elongated openings 102 that are circumferentially spaced around the protective cage 101 and extend vertically. The elongated openings 102 expose the sensor element 100 to the environment outside the protective cage 101 and fluid property sensor 70. In uniform fluid flow conditions, the protective cage 101 creates eddy currents and stagnate zones that promote deposit build up and sensor fouling. However, the fluid device 10 has the fluid passageway 71 configured to prevent accumulation of deposits.

In order to maintain high quality sensor data, the fluid passageway 71 has features that promote scouring of the sensor element 100 of the fluid property sensor 70 through the creation of intensely turbulent zones of oil flow around the in situ sensor element 100. This self-scouring feature eliminates the need for regular cleaning or replacement of the fluid property sensor and ensures that quality data will continually be produced.

In one exemplary fluid device 10, the fluid passageway 71 includes floor 106 that extends to at least one sharp square step (sharp step) 104 which extends to another floor 107 structure at a lower elevation than floor 106. Another (or second) sharp square step (sharp step) 105 (see FIG. 9) impacts fluid flow characters for solenoid 19 the same as the flow fluid characteristics described subsequently for fluid property sensor 70 due to square step 104. In one embodiment, the floors 106 and 107 are planar and generally parallel with the sharp step 104 (and for sharp step 105) extending at ninety degrees relative to each floor 106 and 107. Fluid passageway 71 includes a wall 108 opposite the sharp step 104 that extends at ninety degrees from floor 107 and relative to the floor 106.

The oil flows through the fluid passageway 71 over floor 106 until it encounters the sharp step 104. As the oil flow encounters the sharp step 104 and the different floor depths, the velocity of the oil flow decreases (and for sharp step 105). Moreover, the sharp step 104 causes the oil flow to tumble 73/75 as it is sheared by the slower moving oil flow at the base of sharp step 104 (and for sharp step 105). The oil flow then encounters wall 108 to be diverted toward the sensor element 100 in a ninety degree change of oil flow 73/77 direction from the original oil flow 73 over floor 106.

If the oil flow was uniform at this stage of encountering the wall 108, the oil flow would simply change direction in a uniform manner and enter the fluid property sensor. This oil flow would have minimal mixing and promote formation of eddy currents, which as stated previously, promotes deposit build up and sensor fouling detrimental to consistent and accurate data collection.

However, in the fluid passageway 71 configuration just described for fluid device 10, the oil flow tumbles and encounters the sensor element 100 in a spinning, cork-screw flow pattern. The combination of the sharp step 104 and the wall 108 (ninety degree turn) in the flow path creates a spinning flow that eliminates the potential for deposits collecting on the delicate sensor element 100 (and same fluid flow characteristics for sharp step 105 and solenoid 19).

Still further, the configuration of the fluid passageway 71 for fluid device 10 creates a high velocity and highly turbulent flow around the sampling valve body 33 of solenoid 19 (FIGS. 2 and 9) due to sharp square step 105 (FIG. 9) (and having same fluid flow characteristics as sharp step 104) which ensures that no deposits form near the valve orifice 35. Without this feature, the presence of deposits may lead to oil sample contamination or improper sealing of the valve needle 37 against its seat. It should be noted that the oil sampling valve is threaded into the housing 12/50 of the fluid device 10 and that the oil flow should be able to scour the valve sealing surfaces for any final orientation of the valve as it is screwed in the housing. This is accomplished by creating flows on either side of the sampling valve body 33 that possess very different pressure and velocity characteristics. The result of this is a very high oil flow velocity perpendicular to the flow path at the location of the sampling valve body 33.

In creating zones of intense turbulence for the purposes of scouring, a great deal of energy is dissipated in the oil as it flows through the fluid device 10. This serves to create a pressure drop across the fluid device 10 which allows for the measurement of oil pressures that closely matches the engine oil pressure.

Figure 3C:
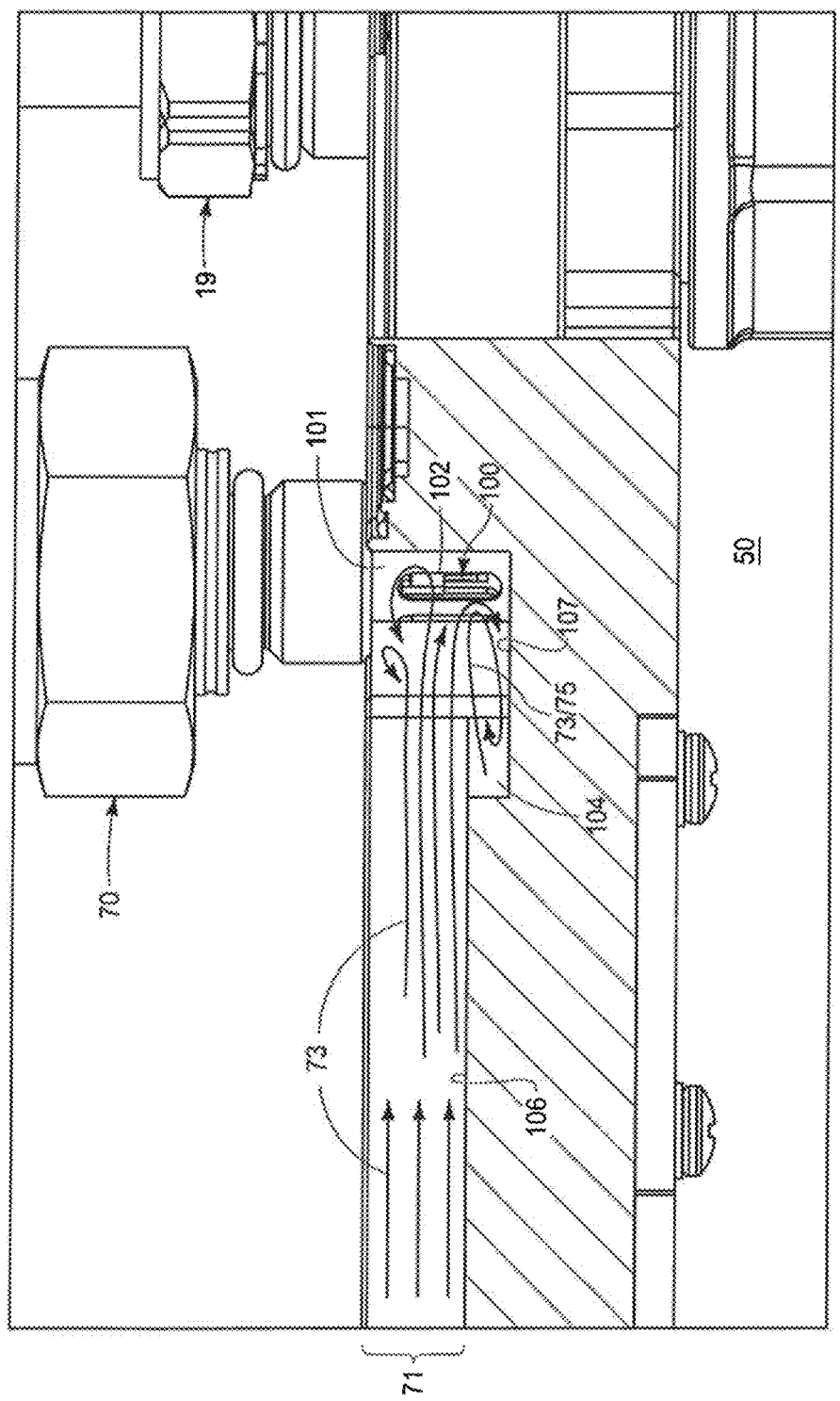
Figure 3D:
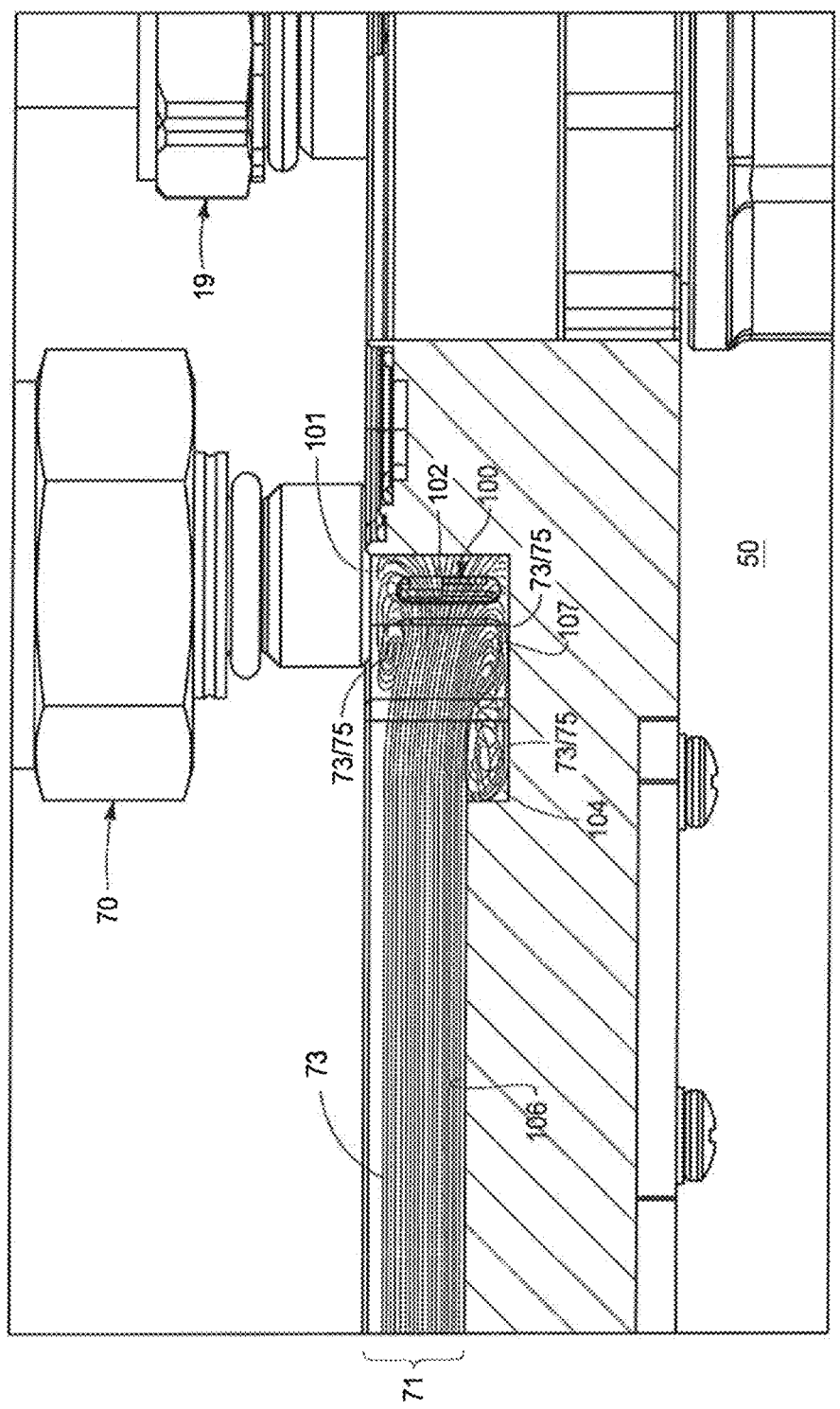
Figure 4:
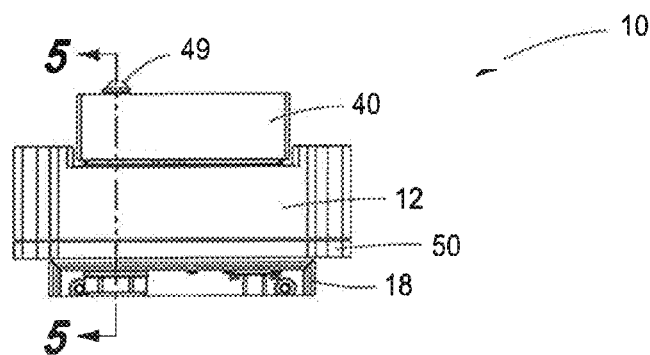
FIGS. 4-13 are different perspectives of various components of the fluid device/system of FIG. 1.

Referring to FIGS. 3C and 3D, the fluid flow through fluid device/system 10/120 is described from a different perspective. The construction of the sensor element 100 of the fluid property sensor 70 incorporates a protective cage 101 configuration that encompasses the senor element 100. In uniform flow conditions oil flowing through the openings 102 in the cage 101 creates eddy currents and stagnant zones (low pressure, low flow zones) that promote buildup of oil precipitates (varnish) that would foul the sensor element 100 rendering the measured data inaccurate or the fluid property sensor 70 inoperable.

Prior attempts to use in situ oil property monitoring have been plagued with damaging varnish build ups on the sensor elements that have led to reduced sensor life and measurement accuracy. In order to prevent such problems, the fluid device/system 10/120 described throughout this document incorporates a novel and unique flow path design.

As the oil flows in a laminar fashion (low Reynolds number) through the fluid device/system 10/120 (recirculating through the engine 15; FIG. 14A), it first encounters a sharp step 104 (and step 105 shown in FIG. 9) in the floor of the oil path asymmetrically increasing the cross-sectional area of the oil path, thus unevenly decreasing the velocity of the oil (consider the Bernoulli principle). This sudden and uneven velocity change causes the oil to "tumble," both roll upwards away from the step and to curl downwards to fill the extra area created by the step 104 (and step 105). The rolling and curling behavior of the oil flow 71 is a result of the flow shearing between the faster moving oil near the top of the flow path 71 and the slower moving oil in the base of the flow path 71 and within the step 104 and step 105). This rolling and curling behavior makes use of the phenomena known as a 'hydraulic jump' which causes the fluid to behave in a way that resembles a rip-tide as waves break on a beach, again, at least in part, due to sharp steps 104 and 105. As the oil tumbles and curls, it becomes intensely turbulent, raising the Reynolds Number of the flow. As the Reynolds number is nothing more than an expression for the ratio between the inertial forces of a fluid and the viscous forces, the increased Reynolds number allows the inertial forces to dominate the flow characteristics, thereby minimizing the potential size of any stagnation zones or eddy currents within critical parts of the oil flow path 71.

The "tumbling," rolling and curling oil then encounters a sharp, 90 degree turn 108 relative to the flow path 71 of the oil. Under normal conditions (with uniform flow), the oil would simply change direction in a uniform fashion and enter the sensor with very little mixing which would promote the formation of eddy currents, especially on the inside of the flow path after the 90 degree turn and on the inside face of the protective cage 101 of the fluid property sensor. However, in the case of the inventive fluid device flow path 71, the flow 71 begins to tumble and spin before it enters the fluid property sensor 70 in a spinning, cork-screw flow pattern. The combination of the square step 104 in the flow path 71 and the 90 degree turn 108 of the oil creates a spinning flow that eliminates the potential for deposits collecting on the delicate sensor elements 100.

In one embodiment, the 90 degree turn 108 can range from about 60 degrees to about 120 degrees relative to the flow path 71 of the oil. Moreover, while the sharp square step 104 is effectively a surface oriented at 90 degrees extending between the two planar and parallel surfaces, the square step 104 can be oriented to range from about 60 degrees to about 120 degrees extending between the two planar and parallel surfaces.

Figure 9:
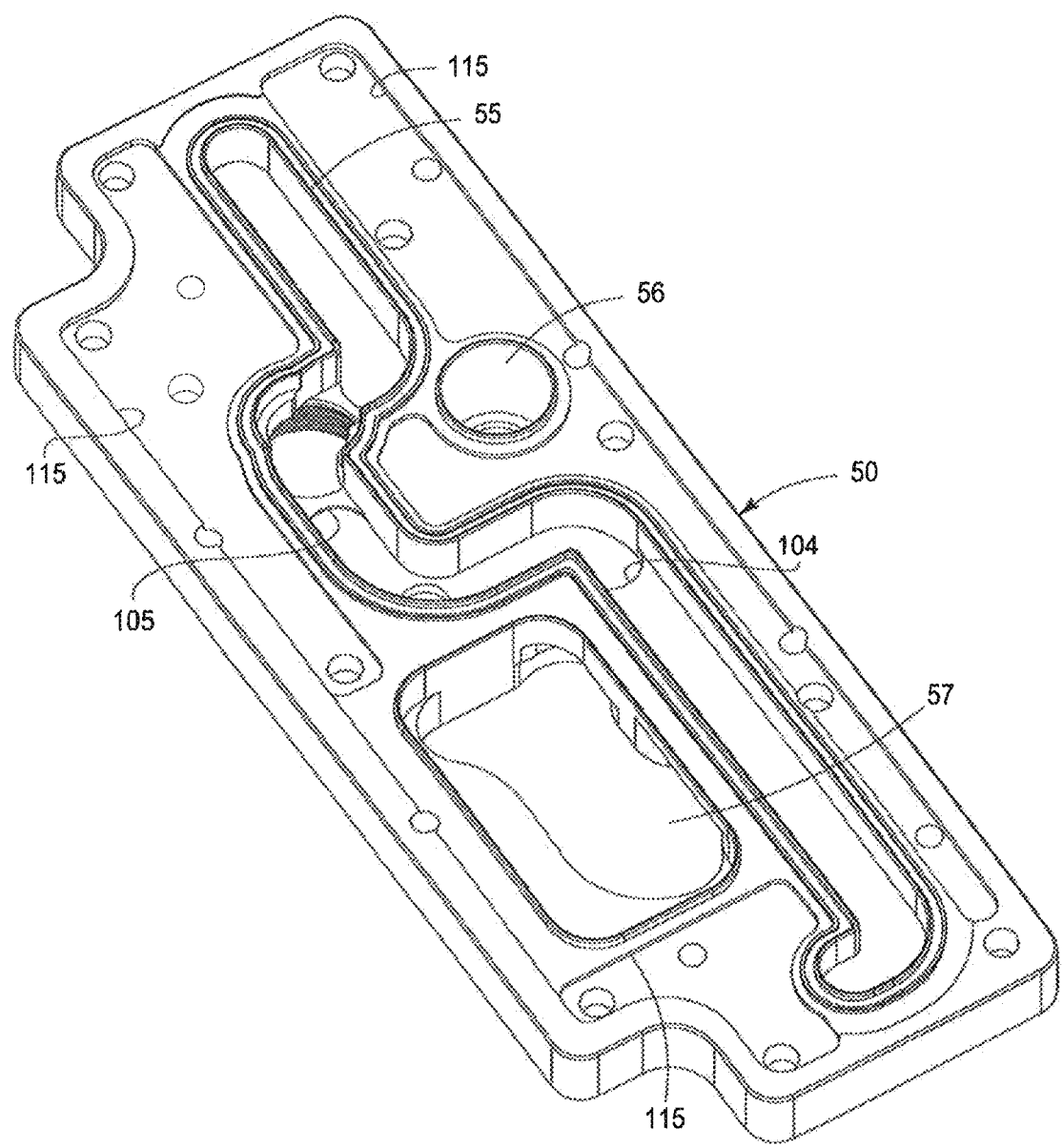
Figure 10:
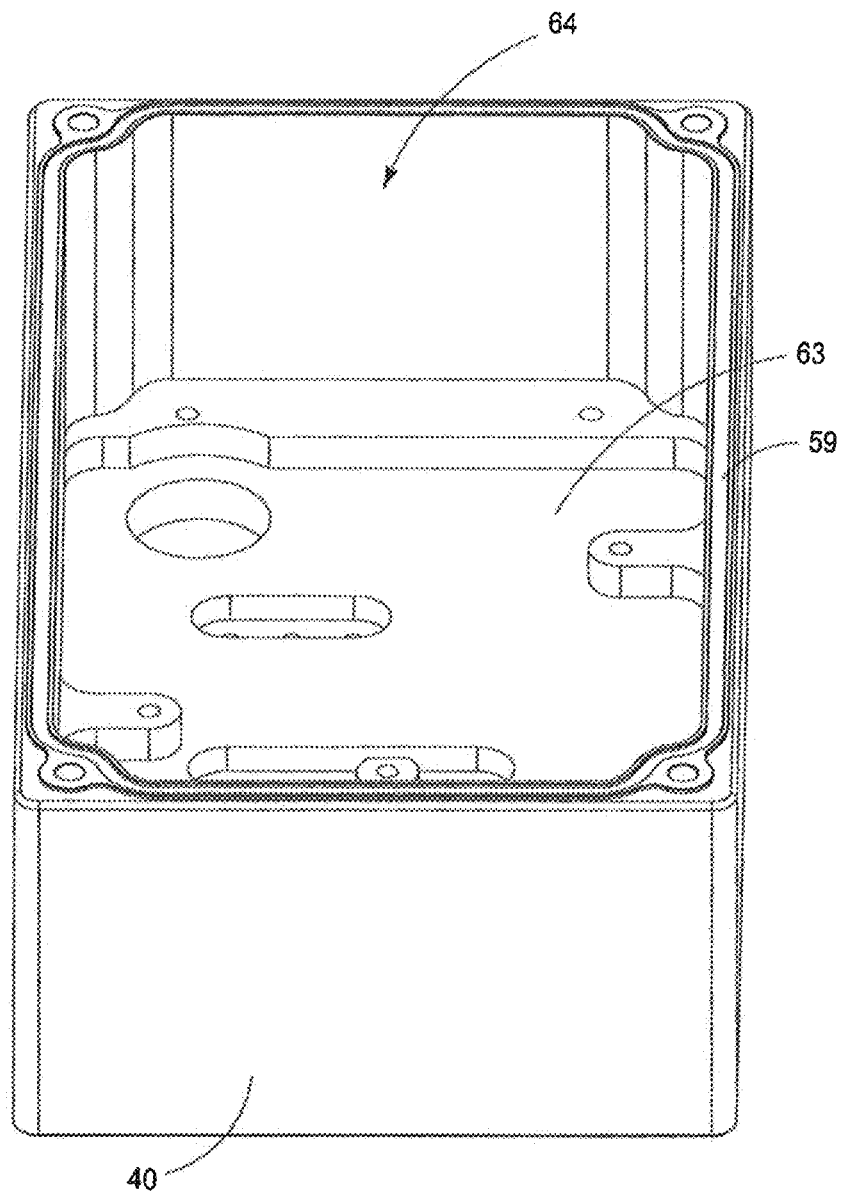
Figure 11:
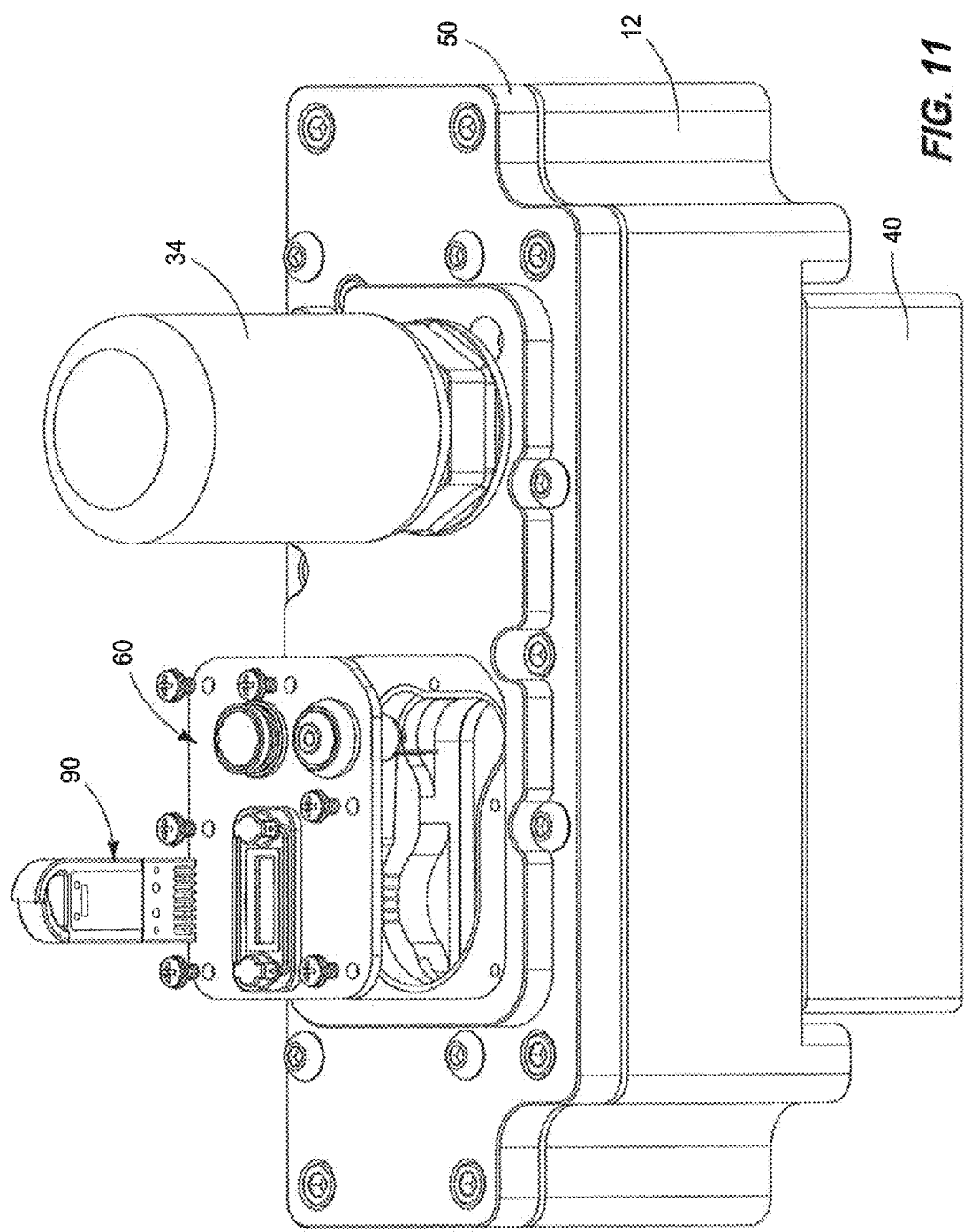
Figure 12:
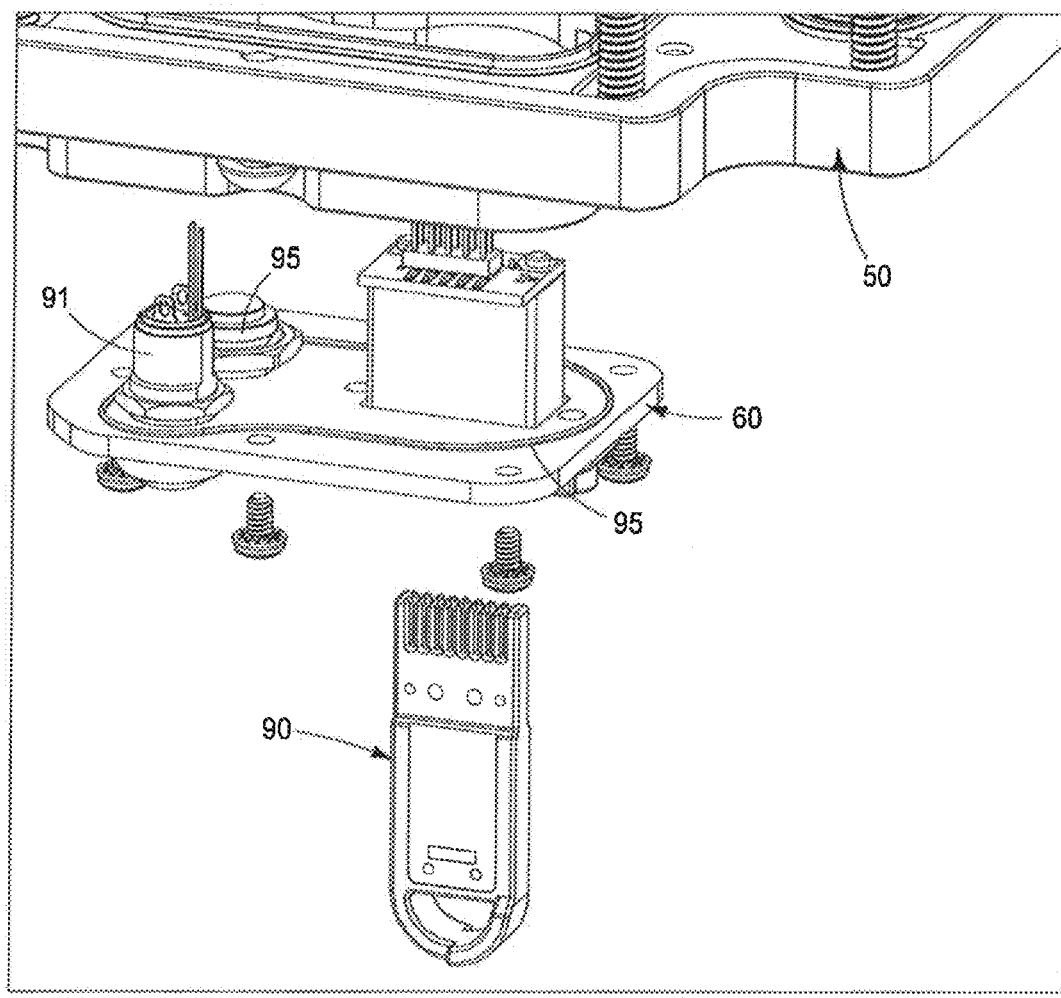

Referring to FIG. 9, sharp square step 105 is shown adjacent, and upstream from, a port 109 (opening) for solenoid 19. The configuration and dimensions of sharp step 105 can be the same as the configuration and dimensions of sharp step 104. In one embodiment, sharp step 104 has different dimensions relative to the dimensions of sharp step 105. In one embodiment, sharp step 104 has a different configuration relative to the configuration of sharp step 105. In one embodiment, sharp step 104 has different dimensions and a different configuration relative to the dimensions and configuration of sharp step 105. Opening or port 109 in lower housing 50 receives solenoid 19 body. It should be noted that port 109 has a specifically designed geometric shape that facilitates and promotes orifice scouring wherein the orifice is for sampling of the fluid flowing in the passageway 71 via solenoid 19 described throughout this document. Recess areas 115 in lower housing 50 reduce thermal conduction from the fluid circulating through passageway 71 such as oil at a high temperature.

Figure 13:
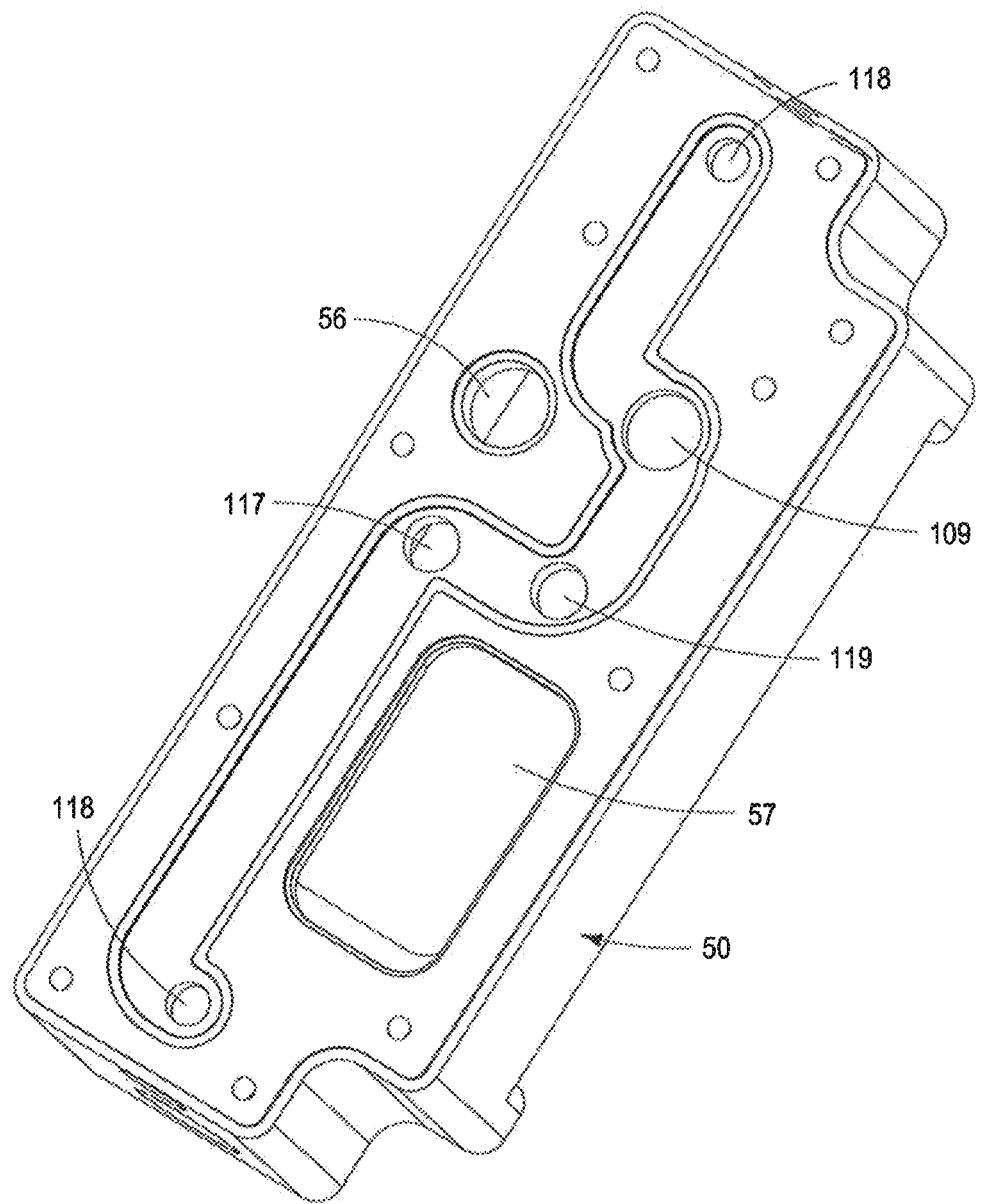

Referring to FIG. 13, lower housing 50 is again illustrated and shows inlet/outlet ports 118 for a fluid entering and exiting lower housing 50 and passageway 71. Still further, port 117 receives a pressure transducer and port 119 receives fluid property sensor 70.

As the goal of the flow path 71 of the fluid device/system 10/120 is to promote a controlled, spinning flow that is devoid of stagnation zones (areas of the sensor element 100 surfaces which have zero fluid velocity past them), uniformly scouring the sensor element 100 surfaces to prevent build-ups from happening. Due to the need to eliminate stagnation zones around the sensor element 100, the flow path 71 cannot simply be made rougher or less direct. The result of features such as increased surface roughness or "speed bumps" along the flow path 71 would result in uncontrolled and somewhat random zones of fluid stagnation in close proximity to the sensor.

Figure 5:
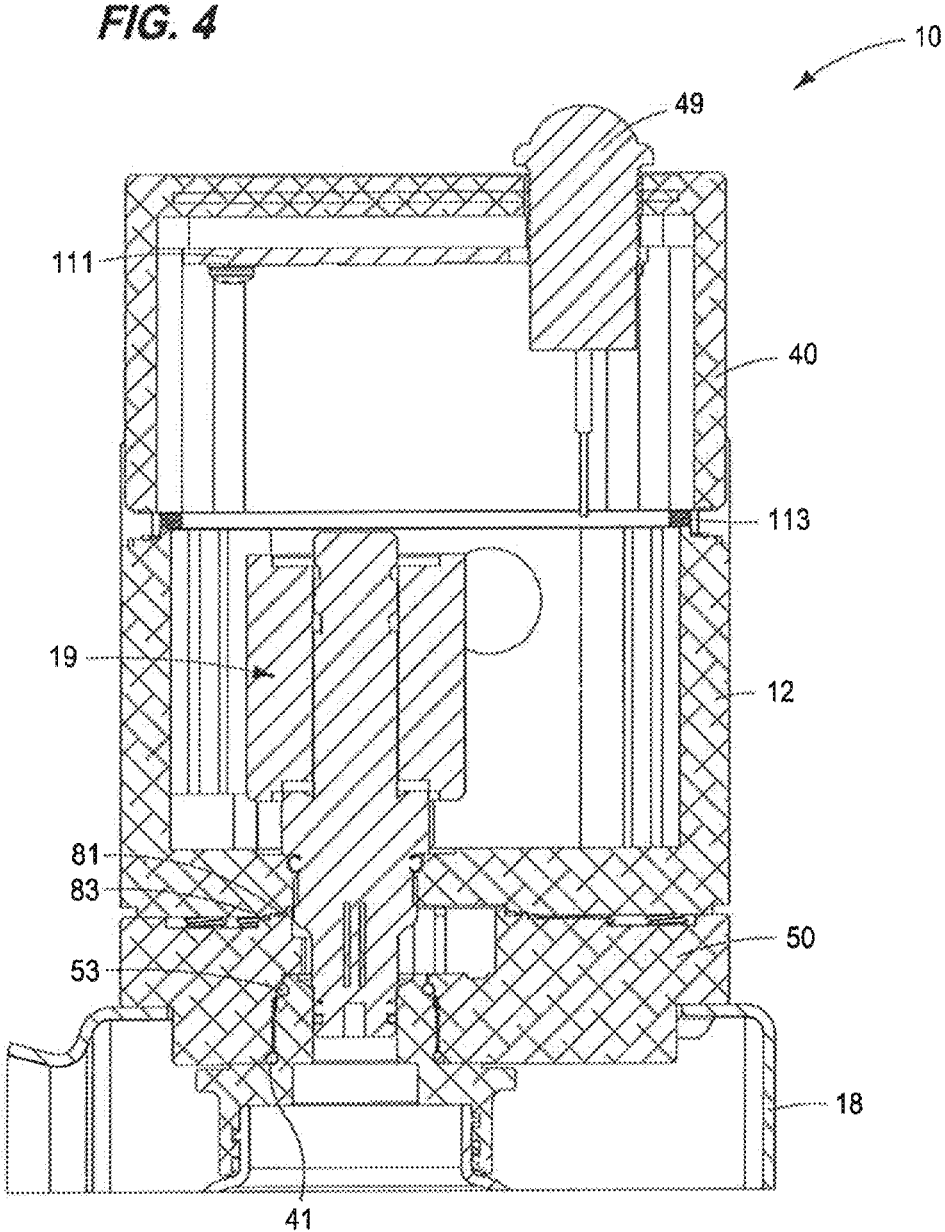

Still referring to FIGS. 1-13, the fluid device 10 includes, between upper and lower housings 12/50, high pressure oil seals (gaskets) 25/27 configured as form-in-place (FIP) seals (gaskets) that are designed to resist the oil pressure imparted by the engine oil pressure system. In one embodiment, exemplary oil pressure range from about 60 psi to about 150 psi. An exemplary FIP seal design is a compression bead contained within a land area that when compressed to about 40% of vertical travel, the bead fills the land groove. A compression stop is integrated into the design to prevent the sealing bead from being over compressed, thus potentially causing a seal failure. In one embodiment, the seal design actually utilizes a double FIP seal path to provide a redundant oil seal providing a safety margin. Dual seal design creates a backup seal to eliminate the risk of oil leaking out of the fluid device 10 flow path. Referring to FIG. 5, a primary FIP seal 81 and a secondary FIP seal 83 are shown between upper and lower housings 12/50.

It should be understood that the reference to "40%" of vertical travel is based solely on the mechanical properties (hardness as measured by the Shore Durometer Type A scale) of the specific silicone sealant material used in this FIP application. If we chose a different sealant with a softer (lower Durometer Share A value) or harder (higher Durometer Shore A value), then the compression value (e.g., 40%) would be adjusted accordingly.

Exemplary seal material is silicone-based for use in high temperature environments. Seals 25/27 provide a sealed environment for the sensitive electronic sensors in fluid device 10 that are placed in situ to the flow-thru oil path. Seals 25/27 (FIP gaskets) are applied to lower housing 50 to ensure a high quality, reusable seal and are removable, and therefore, can be re-applied in the event of seal damage.

Fluid device 10 includes a user interface panel 60. An exemplary user interface panel 60 includes at least three devices for access to interactive features of the fluid device 10. Exemplary devices mounted on user interface panel 60 are: 1) an on-board removable flash data storage key 90; 2) a reset button 91; and 3) a data/configuration port 93. The user interface panel 60 is pre-assembled prior to installation into the lower housing 50 and incorporates an additional form-in-place (FIP) gasket 95 to provide an IP67 seal when properly assembled. The user interface panel assembly 60 can be removed in the field for fast component change-out and ease of upgrade.

An exemplary reset button 91 is a lighted IP67 rated momentary push button switch which allows for the operator of the fluid device 10 to easily reset an oil sampling counter or to collect a manual oil sample vs. a scheduled oil sample. In one embodiment, the reset button 91 is a lighted reset button that provides a visual status indication if a sampling reset is required.

An exemplary removable flash data storage key 90 is a flash memory device that locally stores processed data acquired from or by the fluid device 10 and provided for archival retrieval when needed. If the fluid device 10 is installed without a wired/wireless data link to a database, then the archived processed data can be retrieved manually from the data storage key 90.

An exemplary data/configuration port 93 allows users to locally connect the fluid device 10 to a laptop for the purposes of viewing live data, configuring fluid device 10 settings, or performing a firmware update. In one embodiment, the data/configuration port 93 is a mil-spec IP67 design with a ratcheted locking plug retention mechanism for vibration resistance. In one embodiment, the sampling bottle mount is installed with a 1⅝" wrench and features a precision machined landing surface so that it can be installed extremely tightly into the lower housing 50 (lower body) without over-compressing the o-ring seals.

The fluid device 10 included the previously discussed lid 40 and provides a cover to the upper housing 12 effectively sealing the fluid device 10 from weather, dust, water, gases, etc. The lid 40 also provides mounting for the electronics package and product brand labeling. Lid 40 incorporates a weatherproof seal 110, an integral form-in-place (FIP) seal made from oil resistant silicone. A crush-proof land area is machined into the seal region to prevent the FIP seal bead from being over-compressed, thus potentially compromising the integrity of the seal. This design feature also minimizes the metal-to-metal contact area between the lid 40 and Upper Housing 12. Minimizing the metal-to-metal surface contact means there is less opportunity for heat conduction from the Upper Housing 12 (heated by the hot engine oil coursing through the machined oil path) and the Lid 40 which contains a printed circuit board assembly 111 (PCBA) with heat sensitive electronic components. The Lid 40 remains relatively cool compared to the rest of the fluid device housing and allows for heat to be conducted away from the electronics and into the Lid 40 via the circuit board mounting hardware.

Machined into the Upper Housing 12 is a small "lip" that serves as a shear protection feature, preventing the mounting hardware and integral FIP seal from failing should the Lid experience a sideways blow. Should such an event happen, the shear lip will receive all of the shear loading and the small diameter mounting screws will be left to handle tension only. An exemplary lid 40 is fastened to the Upper Housing 12 with difficult to access tamper-resistant fasteners 113 to prevent unwanted penetration into the sensitive area of sensors and electronics. The Lid 40 design, materials and fastening method supports guideline for "intrinsically safe" rating. An underside of Lid 40 is used to fasten the PCBA 111. The Lid 40 is made from CNC machined aluminum (but could be cast aluminum) so as to provide an efficient heat conduction path for naturally cooling the PCBA 111 heated by the board-mounted components. The external surface of the Lid 40 might also contain heat-rejecting features, i.e. fins, to further reject heat, via passive convective heat transfer to the surrounding air.

Attachment points for the PCBA 111 utilize integrally machined aluminum mounting headers (attachment bosses) which conduct heat away from the PCBA 111 through the pads and out the external surface of the Lid 40. The mounting bosses are arranged in a non-standard, non-symmetrical fashion with respect to the geometry of the PCBA 111. This process minimizes the potential harmonic vibrations that could resonate in the PCBA 111 while operating on a constantly vibrating machine. Any harmonic resonances present in the PCBA 111 could be very damaging to the integrity of the PCBA 111, i.e. solder joints of the surface-mounted components could fatigue, thus allowing the components to "pop off" the board 111. A relatively large contact area between the PCBA 111 and the mounting bosses will facilitate a greater conductive heat flux, thus cooling the PCBA 111 faster and more efficiently. The mating surface between the mounting bosses and the PCBA 111 will be gold (PCBA 111) and machined aluminum (Lid 40). In another embodiment, a heat conducting material (washer, film, grease) can be laminated between the PCBA 111/boss interfaces to increase the heat conduction efficiency, further protecting the PCBA 111 from overheating.

Once the Lid 40 and PCBA 111 have been assembled, it is possible to completely encapsulate the PCBA 111 by flooding the Lid 40 with a heat conducting encapsulation formulation. The 100% encapsulation of the PCBA 111 and related components will substantially add to tamper resistance, vibration stability, providing structural support to the electronic components, i.e. discrete parts, surface mounted parts, etc. In one embodiment, fluid device 10 includes all aluminum outer surfaces being finished with a baked "Safety Orange" ceramic coating (Cerakote®) to provide an extremely tough, abrasion resistant surface for protection from the rigors of an environment experienced in the Oil and Gas industry. Furthermore, for offshore applications that are exposed to open water, salt water spray, and the worst of inclement weather, the ceramic coating will provide the fluid device 10 with an excellent and superior finish.

Figure 6:
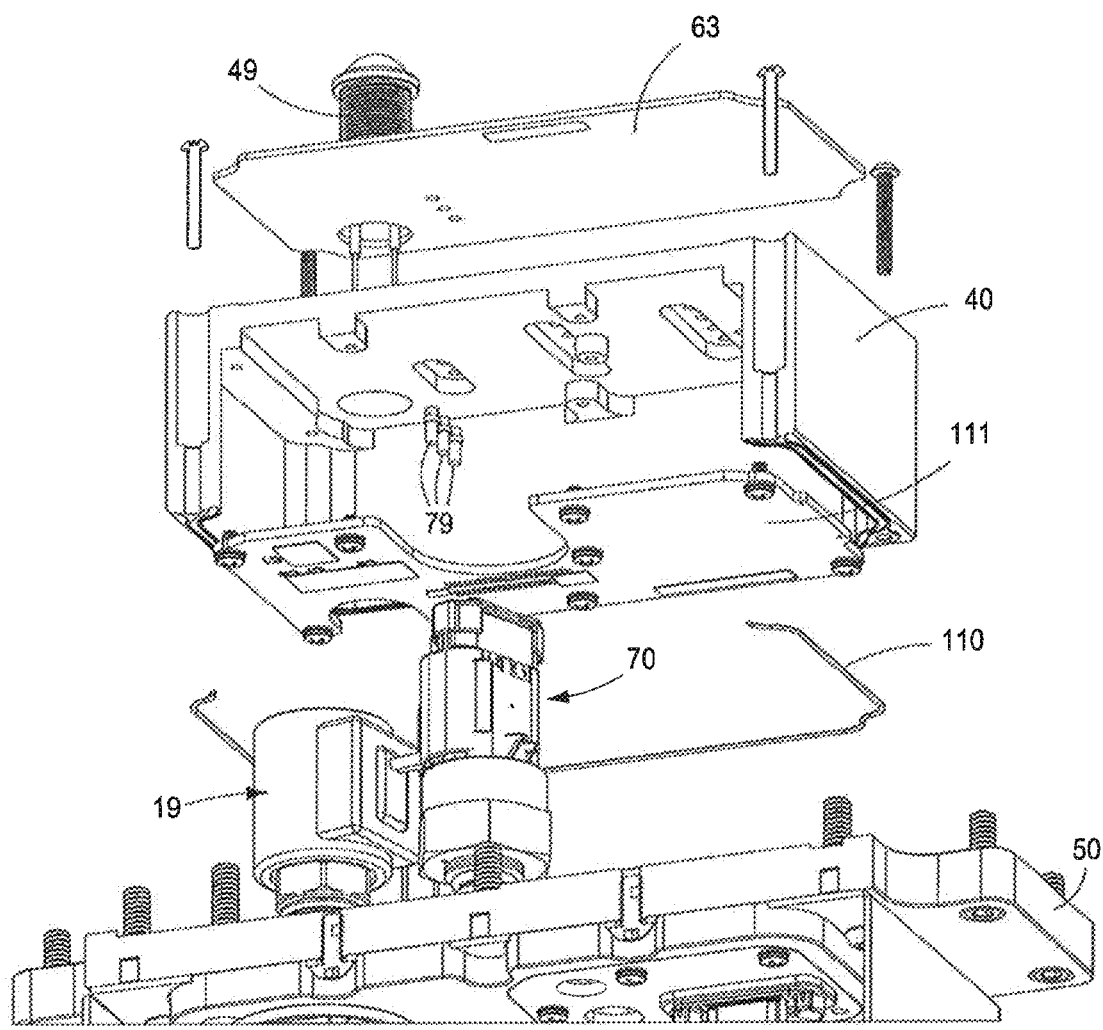
Figure 7:
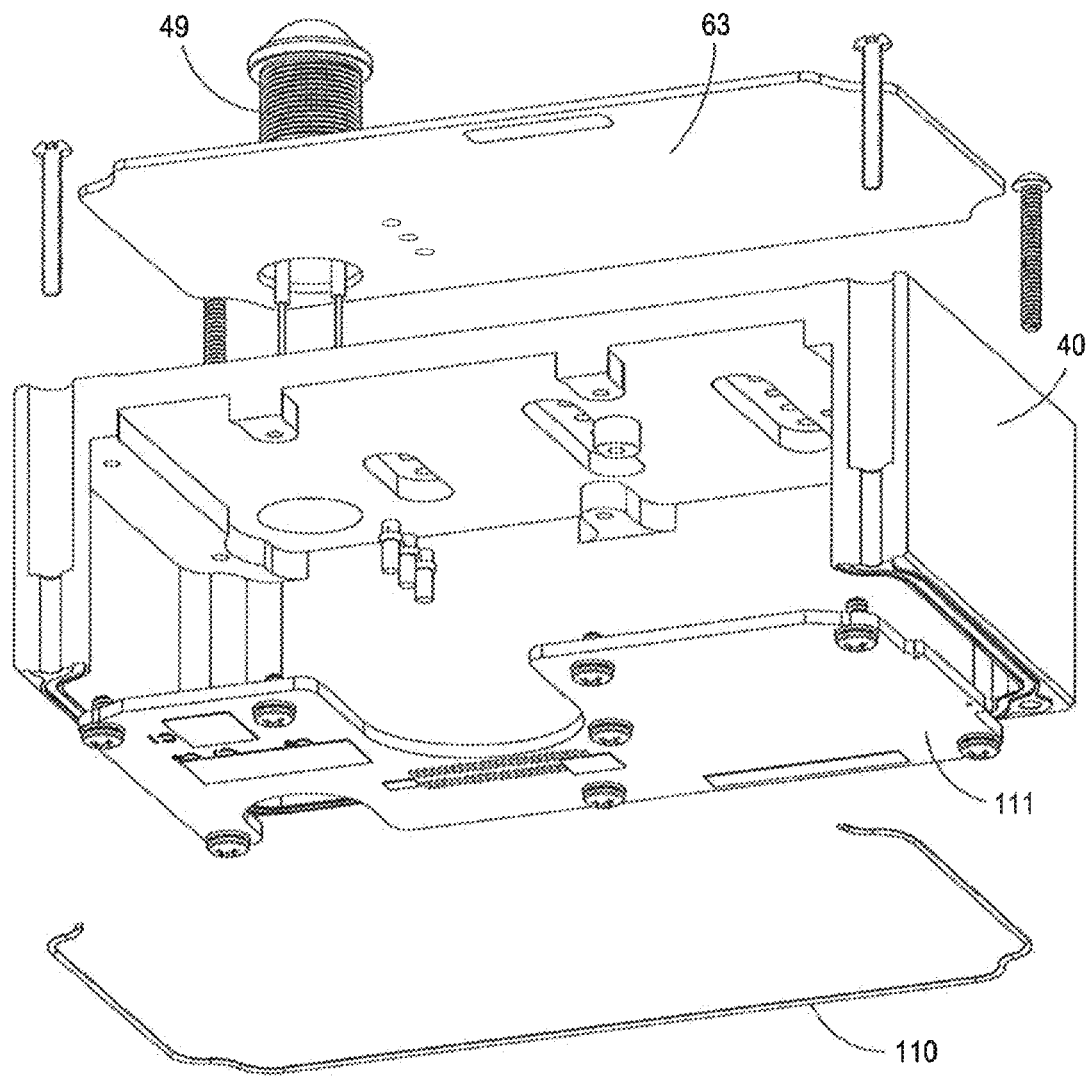
Figure 8:
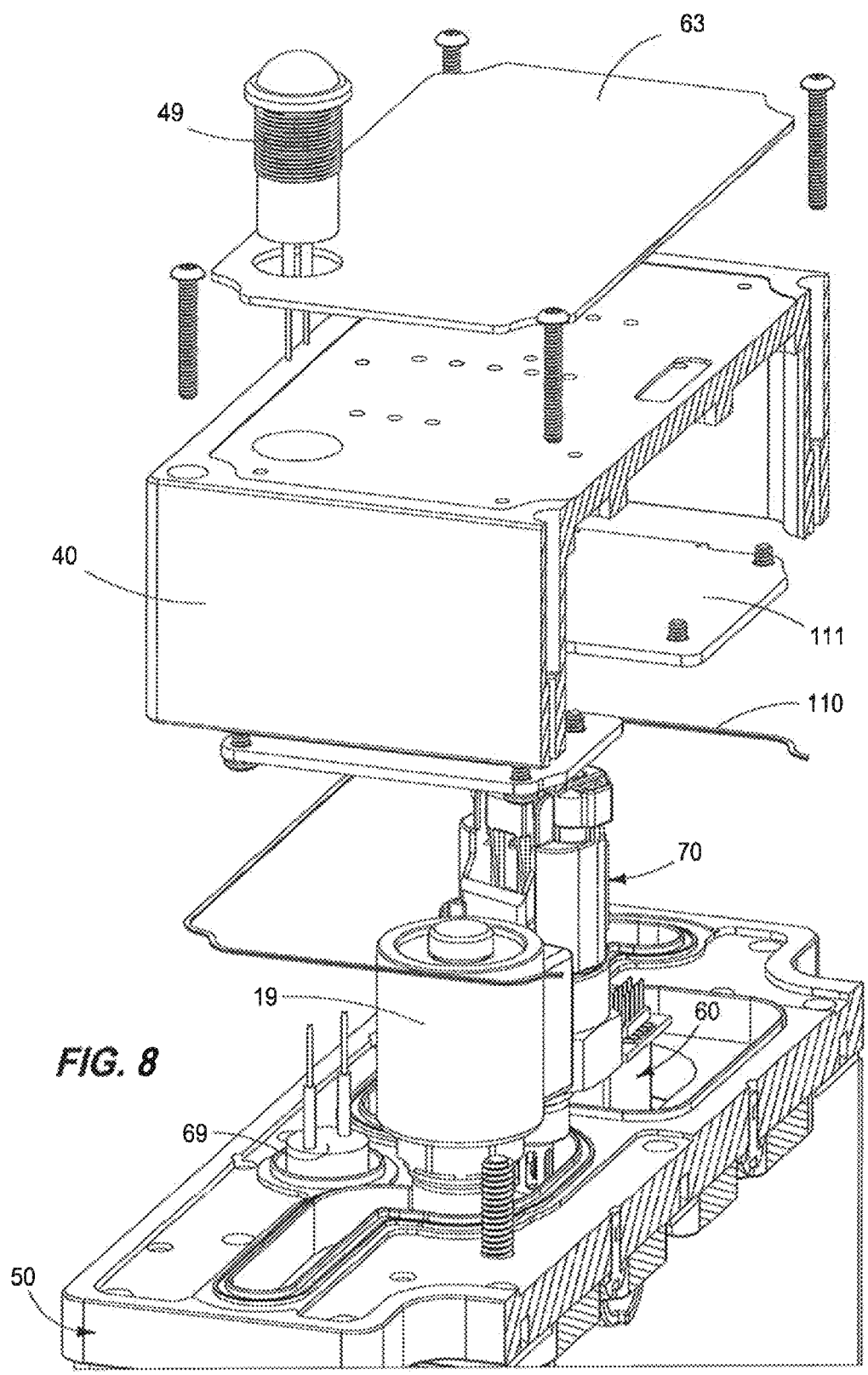

The fluid device 10 includes LEDs, for example LEDs 49 and 69 and light pipes 79 (see FIG. 6). Light Pipe interface holes are machined to a dimension for a snug press-fit of injection molded plastic (clear, light transmitting polycarbonate) Light Pipe components. Machined through holes are counter-bored into the underside of the Lid 40 to position the face of Light Pipe very close (approximately 0.005 inch) to the underside of clear Bezel 63 surface. A recessed pocket is machined into the top (outer) surface of the Lid 40 to accept the adhesively bonded Bezel 63. The depth of the recessed pocket is such that when installed, the top, upper most surface of the Bezel 63 is sub-flush by 0.005 in in order to prevent the Bezel 63 from easily being peeled out off of the Lid 40. This is a tamper-resistance and product durability feature.

Moreover, a through-hole antenna window is machined all the way through the top surface of the aluminum Lid 40 to allow radio waves to be transmitted from, as one example, a Bluetooth® 2.4 GHz PCB-mounted "patch" antenna, through the radio-transparent window and subsequent Bezel 63. The Antenna Window is precisely located to align with the patch antenna mounting location on the PCBA 111. A recessed pocket is machined into the top (outer) surface of the Lid 40 to accept an adhesively bonded metallic Serial Number Plate (SNP). The depth of the recessed pocket is such that when the SNP is installed, the top, upper most surface of the SNP is sub-flush by 0.005 in.

The Bezel 63 serves as a product label and user interface. Bezel 63 construction is that of a laminated polymer featuring: a) pressure sensitive adhesive (PSA) layer (Adhesive Layer) that is on the bottom of the lamination stack and serves to permanently adhere the Bezel 63 assembly to the aluminum Lid 40; a decorative graphics layer (Graphics Layer) that contains the product branding, company information, product safety information and user interface text and/or icons; a media layer (Media Layer); and a clear UV stabilized weather protection layer (Protective Layer). The Adhesive Layer features an application-optimized pressure sensitive adhesive (PSA) for high durability bonding of the plastic Bezel 63 to the ceramic coated (ref. Cerakote®) finish of the Lid-Bezel mounting surface (recessed pocket). The Graphics Layer features the reverse printed product labeling which is selectively applied to allow for visibly transparent windows that align with the location of each LED 49 indicator light, LCD display, lid 40 serial number, etc.

The Media Layer of bezel 63 features a plastic (polyester) sheet that forms the majority of the Bezel's thickness. This material is UV inhibited and designed to hold up to prolonged high temperature exposure and outdoor operation with direct sun UV exposure. The protective layer features a high hardness, UV blocking, satin textured coating to each label that prevents ink pigment fade or label discoloration as a result of long term outdoor operation of the product. This top coating reduces the likelihood of scratches or degradation of the label in all practical fluid device 10 installations. The bezel 63 is adhesively installed into the recessed pocket on the top most outer surface of the Lid 40.

The solenoid cartridge 19 of the fluid device 10 utilizes a solenoid actuated needle valve to allow oil to exit the flow path and fill the sampling bottle 34. This needle valve is designed for ultra-high pressure applications and at lower pressures (<150 psi) it exhibits a leak rate that is effectively zero. This means that the valve will not drip into the sampling bottle 34, it is either on or off. The fluid device 10 can accept multiple sampling valves, mounted in external modules to the main body 12/50, or mounted internally to the main body 12/50. This optional configuration allows for the fluid device 10 to accommodate multiple oil collection samples and store the filled bottles 34 until conveniently able to collect. For example, if daily oil samples are desired, but only collect the bottles 34 once per week, a fluid device 10 configured for 7 bottles 34 would meet this need. This would require that the main body 12/50 would accommodate 7 independent solenoid actuated valves 19, sample bottle mounts 80, bottles 34, etc., all aligned linearly within the oil path. Similarly, a 1-bottle fluid device 10 could be combined together with 6 additional single bottle 34 add-on units (or 1 additional 6-bottle unit).

Sampling needle valves of solenoid 19 are interchangeable so that orifice size can be varied, to accommodate different fluid viscosities. The fluid device 10 is specifically designed so that the sampling valve can be replaced in a rapid and efficient manner.

An exemplary sample bottle 34 includes a high temperature rated 4.2 oz capacity, clear PET bottles to accept hot oil samples without risk of bottle degradation. Cleaned, sealed and sterile sample bottles 34 may be provided directly from a factory to eliminate the risk of sample contamination as a result of impure bottles.

The exemplary sample collection housing 18 of fluid device 10 provides a secure, lockable enclosure for fragile sample bottle 34 and other user interface components. Furthermore, sample collection housing 18 provides for controlled access to the programming port 93 and secure SD card interface, this serves to increase the tamper resistance of the fluid device 10. Sample collection housing 18 is a stainless steel (SS) enclosure (NEMA 4, IP67 rated enclosure) that is bolted to the underside of the Lower Housing 50 utilizing the same shear lip functionality mentioned previously. A custom shaped hole in the top surface of sample collection housing 18 provides an interface with the CNC machined surface of the Lower Housing 50. Fasteners (SS screws with pre-applied nylon thread-locking compound) are installed from within the lockable metal enclosure so as to prevent tampering from the outside of the enclosure by unauthorized personnel. Still further, the sample collection housing 18 acts as a heat-sink by virtue of its extensive SS metal mass and surface area aids in conductive heat transfer from the oil heated Lower Housing 50 (aluminum) thus cooling the main body 12/50.

The fluid device 10 has LED Light Windows in the Bezel 63 configured as transparent areas so that LED indicator lights can clearly and effectively shine through. The clear LED windows are made by selectively applying product labeling ink so as to create transparencies in the Bezel 63 and these are aligned with each LED on a daughter board mounted to underside of Lid 40. Upper most surface of LED light pipe surfaces (for example 49 and 69) is positioned to within 0.005 in. of the underside of the clear LED window to reduce the likelihood of scattering (diffusing) the light from the LEDs 49/69.

The fluid device 10 includes a LED Character Display. In one embodiment, the Lid 63 and Bezel 40 designs have LED/OLED display options for increased flexibility of notification options. The LED display can feature either high brightness 16-segment LED modules for alphanumeric character display, or a high brightness OLED (Organic LED) display for more detailed display capabilities. A clear LED display window is constructed in Bezel 40 in the same fashion as the transparent windows for the LED light pipes.

The fluid device 10 includes at least one antenna window that allows the radio frequency signals necessary for Bluetooth® Communications to penetrate the lid 40. A radio-transparent plastic insert is installed into the lid 40 in place of the aluminum material that makes up the top of the lid 40, with an approximate projected area of 0.5 in×1 in, between product labeling and the Bluetooth® antenna. The Bluetooth® antenna is mounted co-planar, on the top surface of the daughter board, very close to the underside of the lid 40. In combination with the radio-transparent antenna window, this allows an operator's smart device to communicate with the fluid device 10 when in close proximity to the top of the lid 40. This configuration is for security reasons because it requires close proximity to the fluid device 10 to function. In one embodiment, located on the bezel 63 is a variety of system status indicators that are linked to the core functions of the fluid device 10, for example, real-time data collection, oil sampling, dangerous condition checking, add-on sensors, etc.

The printed circuit board assembly 111 (PCBA) of the fluid device 10 includes a motherboard which is the main board and contains all essential electrical components and connectors that are required to complete the core functions of the fluid device 10. In one embodiment, the core functions include: oil sampling procedure, real-time data collection, communications, data processing, dangerous condition determination, and alerting. The PCBA/motherboard 111 also facilitates expansion ability.

The PCBA/motherboard 111 has a multilayer board design for space optimization of component layout and ruggedness as the use environment is continuous heat and vibration. The PCBA/motherboard 111 consists of a 4-Layer laminated printed circuit board (PCB) with both surface mount device (SMD) and discrete through-hole components. Manufacturing and product information is printed on the outer surface of the PCB for easy tracking of part number, revision, and date of manufacture. Furthermore, each PCB is serial numbered for traceability and lot control. Trace widths on the PCB are extra wide (0.015 in.) with respect to their thickness to facilitate reliable PCB-to-component solder joints in high temperature, high vibration operation synonymous with an exemplary application in the Oil and Gas Industry.

If the PCBA/motherboard 111 is to be sold/used in European Union (EU) countries, the PCBA/motherboard 111 can be made RoHAS compliant. If not, the solder used in the PCBA 111 is lead-based which allows for stronger solder joints.

The PCBA/motherboard 111 of the fluid device has a design/configuration that allows for the addition of modular daughter boards to be added on to the assembly. This design/configuration allows for convenient and rapid functionality changes without the need for a complete PCB re-design. Consequently, because of this design/configuration, fluid device 10 can provide a diverse set of functions dependent upon application needs. Still further, modular daughter boards allow for quick change out to adjust for installation specific functions, i.e. indicator light layout, communication antenna, etc. Moreover, the header connector used to mechanically and electrically join the motherboard and daughter board provides conditioned power and a data bus between the mating boards. Furthermore, the number of LEDs installed on a daughter board can be varied depending on the product feature-set (i.e., add-on sensors).

As one non-limiting example, fluid device 10 can include a user interface LED indicator light daughter board designed to present a series of system status, operational condition, and/or warning lights (LED) to meet a specific application. The resulting daughter board may include a dense matrix of LED light positions (i.e. 6 row×5 LEDs per row=30 available LED positions) that are available for utilization depending on specific fluid device 10 application and product configuration. Once determined, the LED light position on the matrix of the available LED locations can be populated with appropriate LED components (soldered to the PCB) to customize the product, i.e., LEGO® fashion. The advantage of this pre-fabricated LED indicator light matrix design is the ability to rapidly configure the daughter board with a custom LED arrangement in order to offer an application-specific feature set.

LEDs are arranged for high visibility in high brightness environments. For example, one embodiment of the fluid device 10 features a unique in-plane RF antenna design that incorporates several high brightness "SERVICE REQUIRED" LEDs for visibility in any condition. Vibration resistant, high reliability board-to-board connector provides for signal transfer and power between the two boards (motherboard and daughter board of PCBA 111). Signal integrity is maintained by carefully designing the data transmission paths within the PCBA 111, as well as selecting high quality electrical connectors for the fluid device 10.

Mounting of the PCBA 111 for the fluid device 10 is provided for by the use of machined in bosses on the underside of the Lid 40 surface that space the PCBA 111 adequately away in the vertical direction from the inner surface of the Lid 40 in order to provide clearance for components, thus eliminating physical interference issues. Stainless steel (S.S.) mounting hardware (i.e., screws, lock washers) is used for durability, longevity, and reliability. Self-locking fasteners (e.g., NyLok®), or use of epoxy on the fasteners may be used to insure fasteners do not loosen over time as a result of cyclical thermal stress and/or vibration. Relatively large contact area between the PCBA 111 ground pads and the mounting bosses integrally machined from the underside of the Lid 40 will facilitate a greater conductive heat flux into the Lid 40, thus cooling the PCBA 111 more efficiently.

Attachment points for the PCBA 111 of the fluid device 10 utilize integrally machined aluminum mounting bosses which conduct heat away from the PCBA 111 through the ground pads and out the external surface of the Lid 40 via natural convection of air movement over the fluid device 10. The mounting bosses (and mounting holes on the PCBA 111) are arranged in a non-standard, non-symmetrical fashion with respect to the geometry of the PCBA 111. This physical geometry configuration minimizes the potential for low frequency and high frequency harmonic vibrations that could resonate in the PCBA 111. Any harmonic resonances present in the PCBA 111 could be very damaging to the integrity of the PCBA 111, for example, solder joints of the SMD components could fatigue thus allowing the components to "pop off" the board.

Due to the need for vibration resistance of the fluid device 10 mentioned in the above paragraph, further design considerations for the fluid device 10 reduce the likelihood of vibration-related failures in the PCBA 111. Multiple layers of copper (heavier copper weight) designed into the multilayer PCBA 111 is employed so as to introduce additional mass-dampening effects that will counteract the effects of vibration related strains placed on the PCBA 111. In one embodiment, a 0.5-oz copper layer is in the PCBA 111 of the fluid device 10. In another embodiment, a 4-oz copper layer is in the PCBA 111 of the fluid device 10. In the embodiment with the 4-oz copper layer, the extra thick layer of copper will add mass and resistance to vibration-induced harmonics in the PCBA 111.

Asymmetric mounting holes in the PCBA 111 of the fluid device 10 (as mentioned above) help to mitigate the risk of damaging harmonic resonances. Local potting (encapsulated) of key (heavy) components can be employed to add additional stability and robustness to the component-to-board solder joints. Lid 40 and PCBA 111 sub-assembly is designed to be completely encapsulated (potted) so as to mechanically and thermally couple the Lid 40 to the PCBA 111. This not only eliminates the risk of vibration related damage to the PCBA 111, it also enhances the conductive cooling of PCBA 111 components and adds an additional level of tamper resistance. The full encapsulation also provides a brute force approach to providing an "intrinsically safe" design to meet explosion proof rating.

The microprocessor of the fluid device 10 assigns both mathematically intensive and time sensitive tasks to a main processor, or CPU. In order to optimally complete these tasks, both ARM and PIC based microprocessor platforms have been considered. In one embodiment, the fluid device 10 utilizes a 16-bit PIC microprocessor. In other embodiments, the fluid device 10 utilizes ARM microprocessors. The microprocessor is physically located on the PCBA 111 as far away from high power, electrically noisy components as possible. This isolation design is intended to minimize the effects of electromagnetic interference (EMI) and radio-frequency interference (RFI), thus increasing the overall reliability of the electrical system.

The fluid device 10 operates on a 24 VDC input, which powers the Sampling Valve Solenoid 19 as well as the high brightness status LEDs 49/69. This 24V supply also powers a 12 VDC and a 3.3 VDC step down regulator to power all logic level components (i.e., microprocessor, sensors, communications, data storage devices). The 24 VDC input is heavily surge protected, over-voltage protected, and reverse polarity protected for robustness. In one embodiment, all power management systems are designed per intrinsic safety best practices and standards.

Since the exemplary application for the fluid device 10 selected has hot oil, for example, 180-190° F., continuously circulating through it, all electronics have to be selected to reliably operate in elevated temperatures. For this reason, board-mounted components have very high rated operating temperatures that range, at least, from about 221° F. (105° C.) to about 257° F. (125° C.). The fluid device 10 includes a high accuracy on-board temperature sensor used to measure the temperature of the PCBA 111 in real-time to confirm that the electronics are not overheating. Redundant critical-to-function on board sensor components (i.e., accelerometer and temperature sensor) are utilized to ensure proper function and to prevent false system alarms. In one embodiment, component-to-board contact area is maximized to facilitate optimal thermal continuity throughout the entire PCBA 111. This facilitates the best possible conduction of heat out of the PCBA 111 and into the Lid 40 where natural convection currents can shed heat.

Fluid device 10 includes sensitive digital (logic level) components such as memory devices, the microprocessor, and associated electronic components are located as far away as possible from radio transceivers and high power, electrically noisy and switching components. This electronic component isolation design is intended to increase the overall reliability of the electrical system for the fluid device 10.

The PCBA 111 of the fluid device 10 utilizes both unidirectional and omnidirectional antennas to support both Bluetooth® and 900 MHz RF communications. The Bluetooth® LE antenna is of the unidirectional type and is mounted co-planar to the PCBA 111, on the top surface of the daughter-board, on the surface facing the underside of the Lid 40, and aligned with a clearance hole machined in the aluminum to facilitate RF transmissions directed up and out of the Lid 40. By optimizing the component clearances and the dimensions of the mounting bosses (integrally machined from the aluminum Lid 40), the PCBA 111 is positioned in a manner that allows for the Bluetooth® LE antenna to be located very close (approximately 0.030 in.) from the underside of the Lid 40.

The fluid device 10 includes a thin (0.062 inch thick) radio-transparent plastic (polycarbonate) sheet laminated and adhesively bonded to the outer surface of the Lid 40 with a permanent pressure sensitive adhesive (PSA) providing a weather sealed cover to the machined RF antenna opening in the aluminum Lid 40. This antenna configuration allows for a smart device (i.e., tablet, smartphone, etc.) to wirelessly communicate with the fluid device 10 when the Bluetooth® LE device is in close proximity to the top of the Lid 40. For security reasons, this is an optimal configuration because it requires close proximity to the machine in order to wirelessly transmit data from the fluid device 10.

The 900 MHz antenna of the fluid device 10 is of the omnidirectional type. The fluid device 10 uses a board-mounted strip antenna (ref. Fractus S.A.) to communicate with other 900 MHz devices. The strip antenna is soldered to a dedicated PCB (Antenna Board) and is mounted perpendicular to the daughterboard via a connector. The antenna board is optionally populated with high brightness LEDs that when flashing/blinking can serve as a visual indication the RF transmission is occurring. This strip-antenna/LED assembly is designed to protrude past the top surface of the lid 40 and is protected by a transparent impact resistant plastic (polycarbonate) shroud or dome that prevents impact or vibration damage to the antenna.

The fluid device 10 includes a firmware stack that provides control for all of the functions performed by the fluid device 10 as well as the data processing algorithms discussed more thoroughly subsequently. The fluid device 10 functions both synchronously and asynchronously in nature. The firmware handles both kinds of processing. Real-time data acquisition (DAQ) and processing is constantly handled by the on-board embedded processor. The firmware performs a large number of on-board data processing functions which enable it to detect a dangerous machine condition ("Dangerous Condition") and initiate a chain of alerts/alarms/notifications so that the dangerous condition can be addressed in real time.

Data gathered by the fluid device 10 is stored in a secure server facility and processed by powerful computing platforms to provide fleet wide analytics and performance metrics. An On-processor RAM is used for storing data required for short term computations. In one embodiment, the PIC microprocessor is equipped with 53 KB of data storage. An On-board SRAM is used for storing all short term data that comes from the sensors or the microprocessor for writing to the ROM or FLASH storage. The PCBA 111 is equipped with 256 KB of SRAM. An On-board ROM is used to store system configuration data and all required device ID information. The PCBA 111 is equipped with 1 KB of EEPROM. The Fluid device 10 includes a removable FLASH media and utilizes a secure and encrypted FLASH storage system, up to 16 GB capacity (ref. DataKey®, ATEK Access Technologies). Fleet-wide 30-sec data is aggregated by communications hardware and transmitted to a secure datacenter for display and for further storage and processing.

The fluid device 10 is designed to maintain two time counts: 1) "Real-Time (RT);" and 2) "Machine-Time (MT)." Employing the dual time management strategy provides the capability for intelligent machine health data that can be evaluated in terms of either: 1) the RT, as in the calendar date and time, that is, year/month/day and hour:minute:second, that an event occurred; and 2) in terms of MT, the equipment operating lifetime (that is, 34,562 hours:26 minutes). MT can be thought of similarly as the odometer in a motor vehicle, an official DOT record of the cumulative number of miles the vehicle has experienced in its history. Another comparison is with a Hobbs™ meter, a device used in aviation to determine the cumulative number of hours (expressed in hours and tenths of an hour) an aircraft has been used.

Real-Time (RT) is maintained by an always-on, low power, high accuracy real time clock (RTC). This RTC module is powered by a CMOS (complementary metal-oxide semiconductor) oscillator that is able to very precisely maintain the current time value (that is, year/month/day and hour:minute:second). As an extra level of precision control, the fluid device/system 10/120 is able to receive automatic time updates from the atomic clock operated by NIST (National Institute of Standards and Technology) via wireless communications with the internet connected remote data and application server(s). This enables the fluid device 10 in a fluid system 120 (FIGS. 14A-14B) to self-correct to clock drift that is inherent to digital timekeeping methods, especially at elevated temperatures. Machine-Time (MT) is maintained in the fluid device 10 using a combination of Oil Pressure sensing, dual redundant vibration sensing and a heartbeat of the fluid device 10 which is coded to be every 20 milliseconds (ms) in one embodiment. The combination of these three inputs allows the fluid device 10 to detect the operational state of the machine/engine, that is, is the engine OFF or ON. The fluid device 10 will count the minutes and hours that the machine is detected to be ON in order to maintain an operational time "Odometer" over the life of the engine.

The fluid device 10 is able to communicate data and alert information to servers for enhanced functionality. An integrated RF 900 MHz radio (902-928 MHz ISM radio Band (ISM stands form Industrial, Scientific and Medical)) allows for wireless communication between the fluid device and external devices such as the data aggregator or other add-on sensors to provide an overall fleet-wide picture of equipment health and operation. The fluid device 10 utilizes a wired Modbus (RTU or ASCII) link over RS485 (or TCP/IP) to communicate with the data aggregator which is installed on-site in an IP67 enclosure. This allows several fluid devices 10 to be daisy chained together. This capability facilitates efficient, easy installation with minimal duplicate wire-runs.

The fluid device 10 further includes a Bluetooth® LE (low energy ver. 4.0) transceiver radio in the 2.40 to 2.48 GHz ISM radio band. Over Bluetooth LE, the fluid device 10 can communicate with handheld smart devices (i.e. tablets, smartphones, etc.) for more effective management of fluid device 10 settings. The Bluetooth LE connection also enables seamless management of the workflow surrounding oil sample collection as use of a fluid device 10 mobile application to tag oil sample bottles with an appropriate ID and generate shipping information needed to send the samples to the laboratory.

Referring to FIGS. 1-14, the fluid device 10 employs a series of in situ digital and analog sensors (at least sensors 19 and 70) that are positioned in the recirculating oil path (flow path) 71 (FIGS. 3A and 3B) which is machined into the Upper housing 12 and Lower housing 50. The arrangement of these sensors 19/70 is linear along the path 71. The sensor bodies 19/70 are threaded into the machined aluminum Upper Housing 12 and incorporate an oil resistant seal to prevent leaking of the engine oil that is coursing through the oil path 71 at high pressure (ranging from at least about 45 psi to about 80 psi) as provided by the engine 15 (FIG. 14A) driven oil pump. An exemplary, non-limiting engine 15 is a Caterpillar G3616 TALE~natural gas fired, 16-cylinder, turbo-assisted, lean burn efficiency. The active sensor tip or sensor cage (element) (for example, 101 of fluid property sensor 70) (FIGS. 3A and 3B) is positioned in a manner as to be subjected to the flow 73/78 of the oil at an angle of about 90°, or perpendicular to the axis of the oil flow 73/78. The sensor signal output is facilitated by connecting the sensor data wires to the printed circuit board assembly 111 (PCBA) affixed to the underside of the Lid 40 which is situated just above Upper Housing 12 and contained in the Lid 40.

The engine 15 driven oil pump delivers an oil flow rate, in one embodiment, in excess of 300 gallons per minute (GPM). The galley port on the engine block that the fluid device 10 is tapped into is one of the high-flow, high pressure ports. This is advantageous in that a high flow rate flowing across the sensor tips presents a constant flow of fresh oil that is turbid 73/75/77/78 (as opposed to a laminar flow) with homogeneously mixed contaminates. This is preferred over the alternative of a slow flow, laminar flow, that may deliver erratic pulses of high concentrations of contaminates which could bias the real-time sensing results. Furthermore, a low flow rate with laminar flow (low shear forces in both the axial and transverse flow direction) could facilitate "plate out" or varnish formation on the sensor tip surfaces which would bias the sensor measurements, or even render the sensor output invalid. To prevent this creation of varnish, the design of the oil flow path 71 in the Upper and Lower Housings 12/50 of the fluid device 10 was created in a manner that would maximize the non-laminar (or turbid) motion 73/75/77/78 of the oil flow 73/75/77/78, thus creating a flow stream that exhibits high shear forces in both the axial and transverse flow directions. This is referred to as a "self-scouring" design.

In one embodiment, the fluid property sensor 70 has a sensor body that is made of 316 stainless steel (SS) and is IP68 rated. The temperature data unit of measure is ° C. (degrees Celsius). An exemplary Fluid temperature range of measurement by fluid property sensor 70 is about −40° C. to about 150° C. Fluid. The fluid device 10 is programmed to update temperature data at 30 second intervals. However, other update intervals are possible, such as, every 5 seconds, and a range of possible update intervals include 5 seconds to 60 seconds and including each integer in between (for example, every 6 seconds, 7 seconds, 8 seconds, 9 seconds, 10 seconds . . . to every 60 seconds). In one embodiment, the digital output is per J1939, CAN2.0B standard or CAN2.0A featuring high-resolution parameter readings. The fluid property sensor 70 is connected to the PCBA 111 (located in Lid 40) via a 4-pin FCI style Molex® connector.

The fluid property sensor 70 of fluid device 10 measures fluid viscosity (in this example, oil viscosity). Viscosity is a measure of fluid resistance to flow and is informally referred to as the "thickness" of a fluid. For example, at the same temperature, maple syrup has a much higher viscosity than water. The viscosity of a fluid is highly sensitive to temperature, that is, syrup at a higher temperature is "thinner," less resistant to flow, and therefore, less viscous than when compared to syrup at room temperature.

Dynamic Viscosity of oil is measured by the digital fluid property sensor 70. For dynamic viscosity data, the SI unit of measure is mPa-s (centipoise~cP). In one exemplary embodiment, the fluid property sensor 70 measures Dynamic Viscosity ranging from about 0.5 to about 50 cP. Dynamic Viscosity data update interval is 30-seconds. Digital output of the fluid property sensor 70 is as per J1939, CAN2.0B standard or CAN2.0A protocols featuring 16-bit parameter readings. The fluid property sensor 70 is connected to the PCBA 111 via a 4-pin FCI Automotive style connector, that is, Delphi® and/or Molex®.

Based on an algorithm to be discussed/presented subsequently, the dynamic viscosity output is temperature corrected to determine if the measured value from the fluid property sensor 70 is within the accepted threshold limits of the Society of Automotive Engineers (SAE) grade of oil used in the application (e.g. SAE 40). Utilizing a controlled lab environment and per industry accepted ASTM protocols, the dynamic viscosity of virgin engine oil (Mobil Pegasus 805®) was fully characterized across a wide range of known engine operating temperatures. The resulting temperature-viscosity curve (shown subsequently) for the subject oil was analyzed using nonlinear regression analysis methods to solve for a math-based algorithm which characterizes the viscosity-temperature relationship for the oil within the range of known engine operating temperatures. This algorithm allows one to reliably determine the expected (virgin) dynamic viscosity value of the engine oil anywhere along the temperature spectrum. The algorithm is embedded into the firmware and is used to process the raw dynamic viscosity from the fluid property sensor 70 in order to determine a current status, dangerous condition, and/or useable life of the oil based on the temperature corrected viscosity value.

As a point of reference, the temperature based viscosity values as reported on manufacturer product data sheets are reported at only two (2) temperatures, 40° C. and 100° C. This is also true of industry recognized ASTM test protocols (ASTM D445) used by in-house and independent labs to determine the oil's viscosity properties. However, it is important to note that the temperature-viscosity curve of any fluid between the two (2) temperature extremes (40° C. and 100° C.) will NOT be linear. As a result of this fact, the resulting curve fit to the measured data is non-linear. The importance of this discovery is that it would be unwise and incorrect to determine the health and/or useful life of a lubricant based on the assumed linear behavior of the oil with a temperature measured between the commonly referenced extremes (40° C. and 100° C.).

The fluid device 10 and fluid system 120 is configured to output the following required data:

Dynamic viscosity value (cP): 16-bit value directly measured by the fluid property sensor 70, value updated every 30-seconds;

Density value (gm/cc): 16-bit value directly measured by the fluid property sensor 70, value updated every 30-seconds;

Kinematic viscosity value (cSt): is calculated by utilizing the Oil Density (measured by fluid property sensor 70), computational formulas are embedded in firmware, value updated every 30-seconds; and Relative viscosity-based condition of the oil: value expressed as a percentage (%) of useful SAE Range, developed computational formulas are embedded in firmware, value updated every 30-seconds.

Consider the following as a representative example (SAE 40 Grade). Per SAE standards, a Grade 40 oil can exhibit a viscosity of 12.5 cP to <16.3 cP and still be considered useable. However, if the oil exhibits an increased resistance to flow such that its viscosity becomes greater than 16.3 cP (>16.3), it has exceeded the upper specification limit for SAE 40 oil and slips into the SAE 50 range (or higher). Correspondingly, if the oil is thinner and measures less than 12.5 cP (<12.5), the oil would be classified as a SAE 30 Grade (or lower). The consequences of operating the subject equipment (engine, compressor, etc.) with an off-spec oil (thinner or thicker) would likely cause damage to the equipment, shorten the useful life of the equipment, and/or potentially lead to a catastrophic equipment failure.

The novel fluid device 10 and fluid system 120 approach to temperature correcting the measured oil viscosity in order to compare it against a "nominal baseline" will provide the operator with a more dynamic, accurate and actionable set of real-time data that can contribute to higher equipment reliability and lower overall operating costs of maintaining the physical asset.

The fluid device/system 10/120 collects real-time viscosity (dynamic) data by the fluid property sensor 70 and is timestamped both in terms of modified Julian date (MJD) (i.e. year:month:day:hour:minute:second) and in terms of equipment operating lifetime (i.e. 34,562 hours:26 minutes). During an oil sample collection event (schedule-based routine oil sample or sample-by-exception oil sample initiated by the detection of a Dangerous Condition event), the 4-oz bottle 34 receives sample oil and is ultimately sent off to a lab for further analysis. The sampling bottle 34 also has both timestamps (MJD and Engine lifetime) associated with the solenoid 19 actuated valve opening event. Comparison of the electronic viscosity data value from the fluid property sensor 70 and the ATSM protocol lab analyzed viscosity data value from the oil sample can provide an opportunity to recalibrate the fluid property sensor 70 mounted on the engine 15. This re-calibration of the electronic fluid property sensor 70 can be autonomously performed on a continuous basis through the utilization of a custom developed API between the oil analysis lab database of the fluid device 10 database.

The fluid device/system 10/120 collects real-time dielectric constant data. A dielectric constant of a material is a measure of its ability to transmit electrical potential energy. The dielectric constant is a simple number that is the relative ratio of the speed of an electric field in a material compared to the speed of the electric field in a vacuum. When the dielectric constant of a lubricating oil is measured, changes in the dielectric constant of the used oil compared to new oil may indicate the presence of contaminants, such as water or particles, or changes in chemistry of the oil such as additive depletion or oxidation." (Machinery Lubrication, *The Dielectric Constant and Oil Analysis*, A. A. Carey, et al (September 2001)).

The dielectric constant of the oil is measured by the digital fluid property sensor 70. Dielectric Constant data SI unit of measure is unit-less. The Dielectric Constant measurement range of the MS85C is about 1.0 to about 6.0. The Dielectric Constant data update interval is 30-seconds by the fluid device/system 10/120. Digital output is as per J1939, CAN2.0B standard or CAN2.0A featuring high-resolution parameter readings. The fluid property sensor 70 is connected to the PCBA 111 (located in Lid 40) via a 4-pin FCI style Molex® connector.

The fluid device/system 10/120 collects real-time density data of the oil flowing through the fluid device 10 by the fluid property sensor (FPS) 70. Density data SI unit of measure is grams per cubic centimeter (gm/cc). Oil Density measurement ranges by the FPS 70 is about 0.65 to about 1.50 gm/cc. The Density data update interval is 30-seconds. Digital output is as per J1939, CAN2.0B standard or CAN2.0A protocol featuring high-resolution parameter readings.

The fluid device/system 10/120 collects real-time oil pressure data of the oil flowing through the fluid device 10 by the fluid pressure sensor (referenced generally with numeral 70 same as FPS) which is a component of the Sensor package 70 which also includes the fluid property sensor (FPS). In one embodiment, the fluid pressure sensor is an analog pressure transducer. It should be understood that in one embodiment, a representative fluid pressure transducer can be purchased from Measurement Specialties™ having an internet address of www.meas-spec.com and is a separate structure from the fluid property sensor 70. As a separate structure, pressure transducer is provided in a separate port in lower housing 50 from fluid property sensor 70, such as port 117 shown in FIG. 13. A specific representative fluid pressure transducer is listed as Model 85-100G-4C.

An exemplary fluid pressure sensor can be made of 316 stainless steel (SS) and is IP68 rated. Pressure data is in SI units of measure which is mPa-s (centipoise~cP). Digital output is as per J1939, CAN2.0B standard or CAN2.0A featuring high-resolution parameter readings, The FPS 70 of the fluid device/system 10/120 collects real-time water content data of the oil flowing through the fluid device 10. An exemplary method of determining the water content includes the fluid device/system 10/120 utilizing the dielectric constant measurement from the FPS 70 described above. The dielectric constant measurement in conjunction with an algorithm (described subsequently) which is embedded in the microprocessor is used to determine the amount of water contamination (water content) in the oil.

Real-time measurement or determination of water content provides the real-time capability to detect engine coolant (water/glycol) that is leaking into the oil system of the engine 15. Such leakage would rapidly compromise the integrity of the engine oil, and therefore, rapidly compromise the integrity of the engine. Such real-time capability to measure water content in the oil system provides the opportunity to prevent a likely catastrophic engine failure if the leak was left undetected and unattended. Water Content data SI unit of measure is parts per million (ppm). Water Content measurements range from about 200 ppm to about 2000 ppm. Water Content data update interval is 30 seconds.

Based on the algorithm mentioned above, the Dielectric Constant data value was outputted from the FPS 70 which was measured from a controlled sample of virgin engine oil (Mobil Pegasus 805®) after carefully titrating a known weight percent (wt %) of a water/glycol solution that was added to purposely contaminate the oil sample. The water/glycol mixture was prepared as a 50/50 mix of deionized water and antifreeze (glycol) to simulate a typical engine coolant. Utilizing a controlled lab environment and per industry accepted ASTM protocols (ASTM D6304A), the Dielectric Constant value of the water/glycol contaminated engine oil was fully characterized across a wide range of known engine operating temperatures. The resulting large database of measured Dielectric Constant data values were analyzed using digital signal processing (DSP) methods to determine a math-based algorithm characterizing the Dielectric Constant-Coolant Contamination relationship, thus being able to reliably determine the water/glycol contamination level anywhere along the Dielectric Constant spectrum. The algorithm is embedded into the firmware library of the microprocessor and is used to data process the raw fluid property sensor 70 output in order to determine a current status, Dangerous Condition, and/or useable life of the oil based on the Dielectric Constant value.

Moreover, the Water Content data collected by the fluid device/system 10/120 in real-time by the FPS 70 is time-stamped (i.e. year:month:day:hour:minute:second). During an oil sample collection event (schedule-based routine oil sample or sample-by-exception oil sample initiated by the detection of a Dangerous Condition event), the 4-oz bottle 34 of sample oil collected and sent off to a lab for further analysis also has a timestamp associated with the solenoid 19 actuated valve opening event. Comparison of the electronic Water Content data value (from FPS 70) and the ATSM protocol lab analyzed Water Content data value can provide an opportunity to recalibrate the FPS 70.

The fluid device/system 10/120 has the capability to detect equipment (in this case engine 15) ON/OFF status in real-time. That is, in real-time determine if the equipment (engine, compressor) is actually operating. A Dangerous Condition alarm notification would be generated if the equipment was confirmed to be non-operating. This is important for equipment such as natural gas compression equipment (gathering gas, gas processing, gas transmission applications), which are designed to operate on a 24/7/365 basis, were such equipment to suddenly experience a shutdown event.

The capability to detect equipment ON/OFF status is by utilizing a PCBA 111-mounted accelerometer and the Oil Pressure value from the FPS 70 to make a determination that the equipment has experienced a shutdown event. A Dangerous Condition algorithm is embedded in the firmware of the microprocessor. The Algorithm contains a routine that looks for a minimum of four (4) consecutive 30-second Oil Pressure values (total of 2 minutes) to minimize the possibility of a false positive which would result in an inaccurate alarm notification. Each ON or OFF event is captured and logged in the database maintained on a secure remote server. Still further, equipment OFF duration and frequency is logged to provide Equipment Uptime, a key performance indicator (KPI) metric closely managed.

If the real-time monitored Oil Pressure value were to suddenly go to zero while the accelerometer measured constant vibration, the possible scenario is that the oil line to the fluid device 10 has been compromised and is likely leaking and/or spewing oil all over the place. Conversely, if the Oil Pressure measure is positive and the accelerometer is negative, it would indicate that the PCBA 111-mounted accelerometer has failed and needs to be replaced or re-calibrated.

The fluid device/system 10/120 has the further capability that couples the real-time measurement of oil quality with physical oil sample collection for further oil measurement of oil quality, typically in a controlled lab environment and per industry recognized ASTM protocols, and comparing the real-time quality measurement with the quality measurement of the sampled oil in the lab.

Proprietary Algorithm for Real-Time Temperature Correction of Engine Oil Viscosity In order to develop the Algorithm for Real-Time Temperature Correction of Engine Oil Viscosity for the Fluid Device/System 10/120, an experiment was conducted to determine the effects of oil temperature on oil viscosity in virgin engine oil. The motivation to carry out this experiment was the need for real-time temperature correction in the Fluid Device/System 10/120 as well as lack of data in ASTM D445 documents.

This experiment was carried out in two stages, the first being the laboratory experiment designed to produce the empirical temperature-viscosity data for virgin engine oil (Mobil Pegasus 805®) and the second being the regression analysis performed to obtain the temperature-viscosity algorithm for the Fluid Device/System 10/120.

Stage—1: Baseline Oil Viscosity Recording

Define oil temperature range for the experiment based on data provided in engine OEM specification and ASTM D445 standard. Record baseline dynamic viscosity values (units: cP) for the engine oil at fixed oil temperature intervals spaced evenly within the defined range.
 a. Experimental Apparatus
  250 ml Pyrex® glass beaker
  500 ml Pyrex® glass beaker
  200 ml virgin engine oil
  Hot Plate with magnetic stir bar & temperature probe attachment
  Measurement Specialties FPS 2800 Fluid Property Sensor with Arduino-based data acquisition device Ring stand Ring clamp b. Methodology The 250 ml beaker is placed on the hot plate inside of a 500 ml beaker that is filled with water to provide even heating of the oil sample. Virgin engine oil is poured into the 250 ml beaker. The temperature of the oil is precisely controlled using the hot plate's temperature probe attachment which provides feedback to the hot plate's internal temperature controller. The fluid property sensor element (FPS 70) is immersed in the oil using the ring stand and ring clamp. The fluid property sensor (FPS 70) measures oil properties such as oil temperature, dynamic viscosity, density and dielectric constant and it transmits the measured data over the CAN (Controller Area Network) bus protocol. The Arduino data acquisition device is configured to capture this data into a log file which can be read into the computer for further analysis. In order to produce high quality data, for each oil temperature value, multiple viscosity values were tabulated to remove human and experimental errors.

c. Experimental Results

Figure 24:
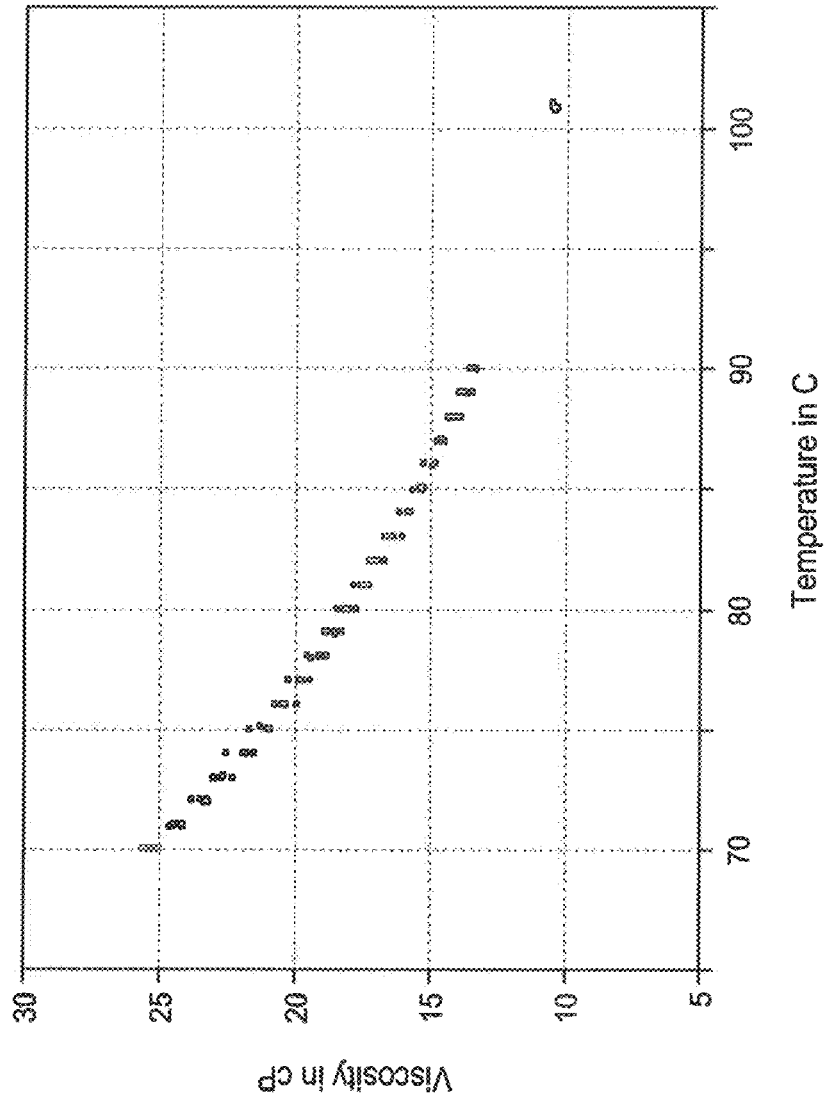
FIG. 24 is Dynamic Viscosity over Oil Temperature in C scatter plot for virgin oil.

The resulting scatter plot of Oil Temperature in Celsius vs. Dynamic Viscosity is shown in FIG. 24 below. As expected, oil viscosity decreases with increasing oil temperature (e.g.: hot maple syrup flows easily compared to cold syrup). Since precision temperature control was adopted, viscosity values appear as a stack at each oil temperature value. Also, the utilization of a precision temperature control served to greatly reduce noise in the data and eliminate outliers. This data is then used in the second stage of the experiment where a curve fit equation is derived.

Stage—2: Baseline Oil Viscosity Curve Fitting

In order to develop the Algorithm for Real-Time Temperature Correction of Engine Oil Viscosity for the Fluid Device/System 10/120, a curve fit equation is derived to describe the experimentally collected data in Stage 1.

a. Methodology

From the scatter plot (FIG. 24), it is clear to the casual observer that the data is non-linear, that is, it appears less as a straight line and more as a curve. The process of evaluating a set of data points and deriving a curve is known as regression. In this case, since the data is non-linear, the optimal regression method is non-linear regression.

The quality of curve-fit is decided by two factors:

Factor 1—Goodness of curve fit: This is indicated as $r^2$ and is termed statistically as co-efficient of determination. The closer $r^2$ value is to 1 (or 100%), the better is the curve fit.

Factor 2—Performance of the curve within the OEM specified temperature range: The performance of an ideal curve would be no bias (or swing) towards extreme values at a given oil temperature. Ideally, the curve should pass through the average (or mean) value of oil viscosity at each oil temperature. A perfect curve for the dataset would exactly represent the behavior of the dynamic viscosity of the specified oil type at a given temperature value.

b. Results

Figure 25:
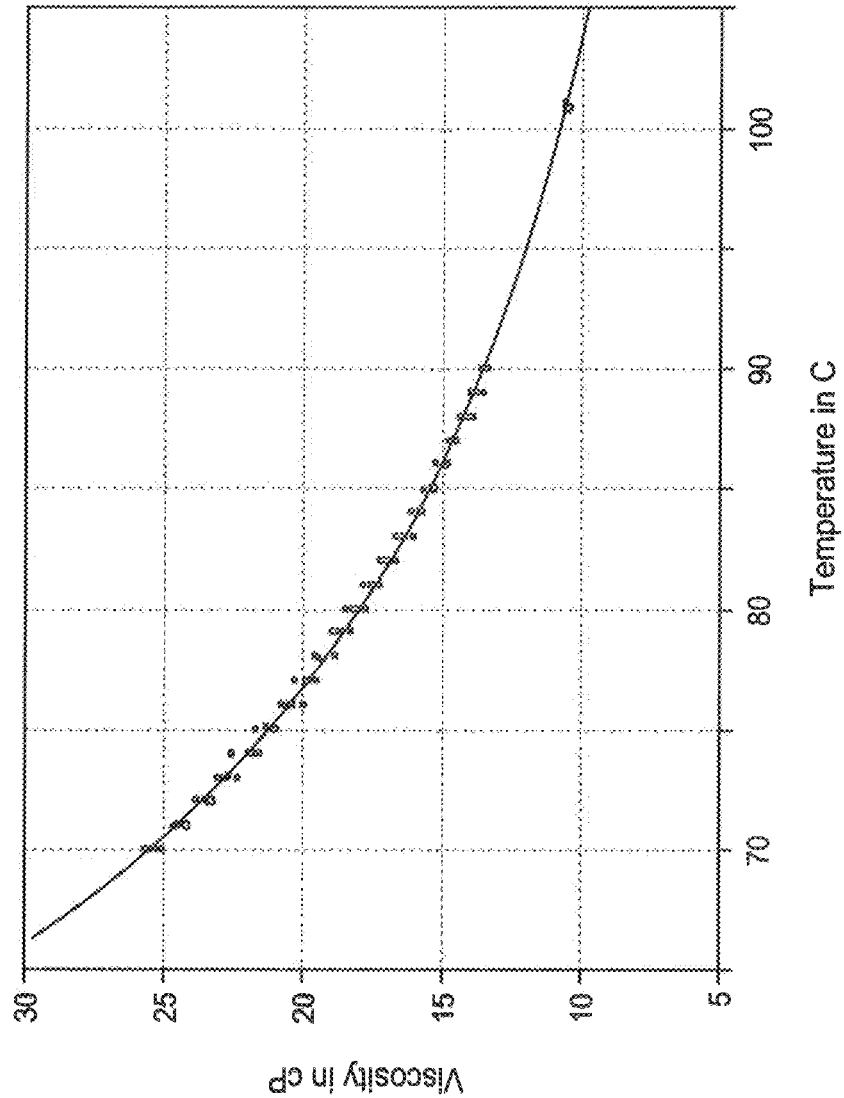
FIG. 25 is Baseline Viscosity curve fit.

The highest performing derived curve for the baseline viscosity values is as shown in FIG. 25.

The derived curve-fit equation can be represented in a mathematical format shown in Equation 1.

$$\mu=(a+b/T^2)^2 \qquad \text{Equation 1}$$

Here,

μ is dynamic oil viscosity in cP

T is oil temperature in Celsius.

a & b are curve-fit coefficients which decide the shape of the curve.

Their values are, respectively: 1.5763649 and 17018.976.

Conclusion

Equation 1 is used in fluid device/system 10/120 firmware to correct oil viscosity values in real time with respect to changes in oil temperature.

The Goodness of Fit (or $r^2$) for the selected equation was found to be 99.758%, which implies the accuracy of the curve fit is high.

The mathematical simplicity of Equation 1 allows for a robust implementation on the fluid device/system 10/120 embedded platform. The relative simplicity helps to eliminate numerical errors such as rounding off and truncation of the calculated values due to the nature of embedded platforms.

Algorithm for Temperature Correction for Dielectric Constant

Water Content—the fluid device/system 10/120 utilizes the Dielectric Constant measurement from the fluid property sensor 70, in conjunction with a custom developed algorithm (see FIG. 16) embedded in the microprocessor to determine the amount of "free" water contamination in the oil. An interest exists in the ability to detect engine coolant (mixture of water and ethylene glycol) leaks in real-time, a condition that would rapidly compromise the integrity of the engine oil if left un-checked. Such a real-time water detection capability would allow operators to prevent a catastrophic engine failure that would have been left undetected and unattended without the fluid device/system 10/120.

Dielectric Constant measured by the digital fluid property sensor 70. Through the use of the Algorithm, dielectric constant data and temperature data are converted into the water contamination in oil as expressed in parts-per-million (ppm).

An algorithm, the result of laboratory experiments, uses dielectric constant data and temperature data provided by the fluid property sensor 70 to determine the water content of oil on 30-second intervals. The water content value is then used to issue WARNING or DANGER alarms if the value is calculated to exceed "safe" operating condition thresholds.

The exact threshold values are set by the engine (or compressor) manufacturer. Example of a DANGER threshold (also referred to as a 'condemning limit' by OEM manufacturers) for a Caterpillar 3600 series engine is 5000 ppm for water and 0 ppm for ethylene glycol.

Water Content data SI unit of measure is parts per million (ppm). Water Content measurement range of the fluid property sensor 70 used in the fluid device/system 10/120 is 200 to 600 ppm. Through the addition of a second water detection sensor that measures "saturated" water (vs. free water) in oil, (for example, an HTM2500 sensor sold by Measurement Specialties), the water-in-oil detection range can be extended to 2000 ppm. Water Content data update interval is 30-seconds.

Based on the algorithm, the Dielectric Constant output from the fluid property sensor 70 was measured from a controlled sample of virgin engine oil (Mobil Pegasus 805®)

after carefully titrating a known volume percent (vol %) of a water and ethylene glycol solution was added to purposely contaminate the virgin oil sample. The water/ethylene glycol mixture was prepared as a 50/50 (vol %) mix of deionized water and antifreeze (ethylene glycol) to simulate a typical engine coolant. Utilizing a controlled lab environment and per industry accepted ASTM protocols (ASTM D6304A), the Dielectric Constant values of water/ethylene glycol contaminated engine oil (Mobil Pegasus 805®) across a wide range of expected engine operating temperatures (150° F. to 200° F.) were fully characterized. The resulting large database of measured Dielectric Constant data values were analyzed using statistical signal processing methods to develop an algorithm for characterizing the Dielectric Constant-Water Contamination relationship, thus enabling the capability to reliably determine the volume amount of water/ethylene glycol contamination present in a given sample of oil. The developed algorithm is embedded into the firmware and is used to process the raw fluid property sensor 70 output in order to determine a current oil-water contamination status, identify the presence of a Dangerous Condition based on water content, and/or calculate the useable life of the oil based on the Dielectric Constant value.

Real-Time Sensor Derived Water Content Data vs. Lab Derived:

The Water Content data produced by the fluid device/system 10/120 from the real-time fluid property sensor 70 output is timestamped both in terms of modified Julian date (MJD) (i.e. year:month:day:hour:minute:second) and in terms of equipment operating lifetime (i.e. 34,562 hours:26: minutes).

During an oil sample collection event (schedule-based routine oil sample, manual sample or sample-by-exception oil sample initiated by the detection of a Dangerous Condition event), the 4.2-oz oil sample bottle 34 is filled and sent off to a laboratory for further analysis. The sample event also has both MJD and MT timestamps associated with the precise instant that the solenoid 19 actuated valve opening event occurred.

Comparison of the electronic Water Content data value (from the fluid property sensor 70 of fluid device/system 10/120) and the ATSM protocol lab analyzed Water Content data value can provide an opportunity to recalibrate the mounted electronic fluid property sensor 70 if required.

Fluid Monitoring and Management System

An exemplary, non-limiting, fluid monitoring and management system 120, while previously mentioned, is now described more thoroughly according to one of various embodiments of the invention.

Figure 14B:
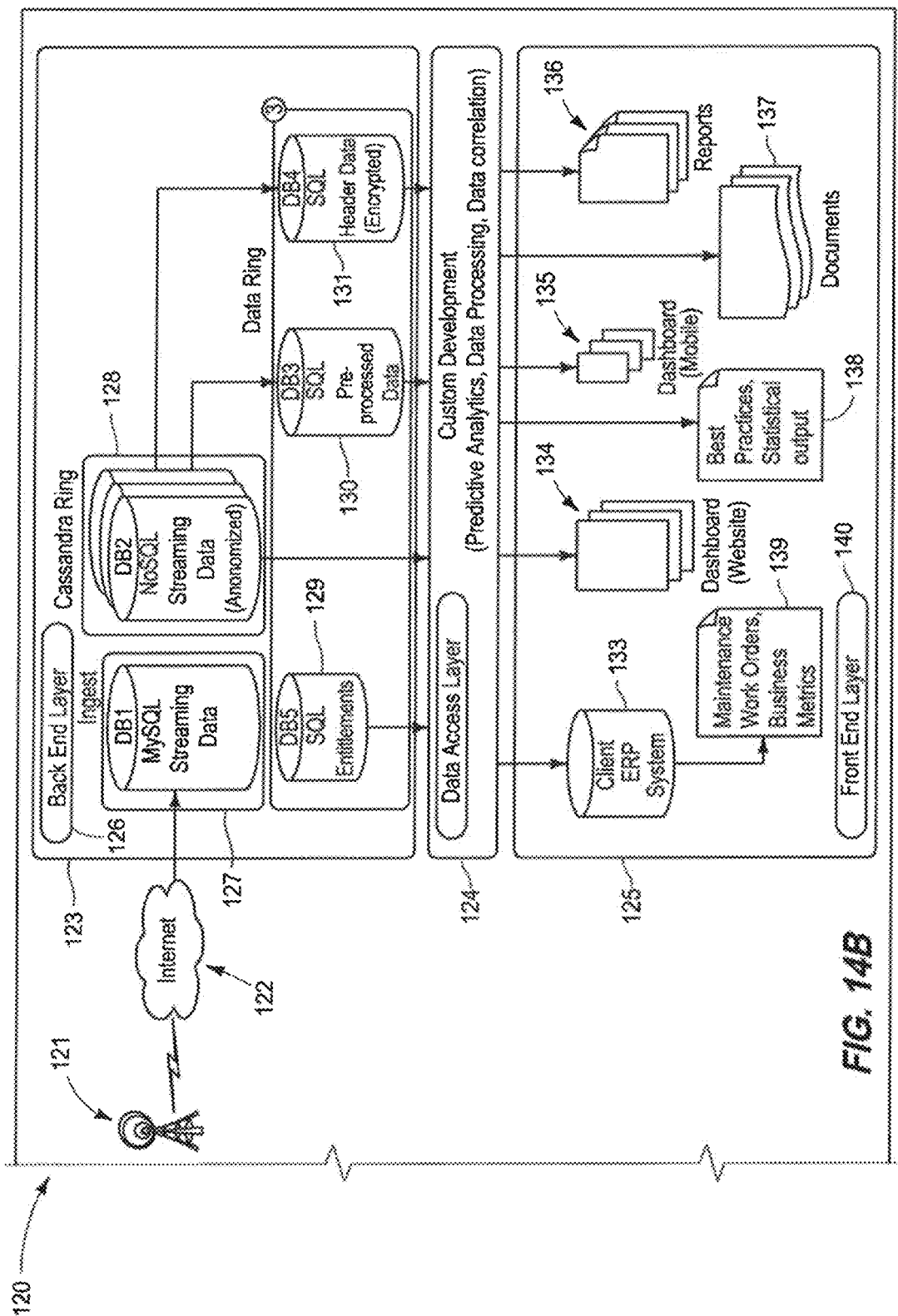

Referring to FIGS. 14A and 14B, the fluid device 10, as previously extensively described, is incorporated into fluid system 120 according to one of various embodiments of the invention. A supply line 17 provides fluid communication between a fluid system of a subject machine or equipment and the fluid pathway 71 (FIGS. 3A and 3B) of fluid device 10. In one non-limiting embodiment as stated previously for this document, the fluid system is an oil system of an engine 15. In one embodiment, fluid device 10 is mounted directly to the subject machine or equipment. In one embodiment, fluid device 10 is mounted remotely from the subject machine or equipment. Supply line 17 allows oil to exit from engine 15 and to enter fluid device 10. A return line 61 provides fluid communication with the oil system of engine 15 and the fluid pathway 71 of fluid device 10. Return line 61 allows oil to exit from fluid device 10 and to reenter engine 15. Fluid device 10 includes a user interface 66 (system status indicator (LED)).

Wired connection 63 provides electrical/data communication between electrical components of fluid device 10, for example, the printed circuit board assembly 111 (PCBA), and a data aggregator/communications hub 65. Data aggregator/communications hub 65 is in electrical/data communication with a wireless receiving/transmission system 67. In one embodiment, the data aggregator/communications hub 65 can support/accommodate 1 to 8 fluid devices 10. In one embodiment, the data aggregator/communications hub 65 can support/accommodate more than 8 fluid devices 10. Wireless receiving/transmission system 67 provides cellular and satellite connectivity to any remote site capable of receiving radio waves. Consequently, this connectivity allows electrical/data communication (signal communication) (radio waves) between the fluid device/system 10/120 and any remote site.

For example, referring to FIG. 14B, the electrical/data communication (signal communication) (radio waves) from wireless receiving/transmission system 67 is received by repeater 121 and transmitted to, and received by, ultimately, the internet 122 (and/or "cloud"). From internet 122, electrical/data communication is transmitted to, and received by, a remote data server 123 (that is, back end layer 126). In one embodiment, remote data server 123/back end layer 126 includes access to/communication with at least one or more databases (DB). For example, remote data server 123/back end layer 126 includes: an exemplary first database DB1 127 that includes MySQL Streaming Data; an exemplary second database DB2 128 that includes NoSQL Streaming Data (Anonomized); an exemplary third database DB3 130 that includes SQL Pre-processed Data; an exemplary fourth database DB4 131 that includes SQL Header Data (Encrypted); and an exemplary fifth database DB5 129 that includes SQL Entitlements.

Databases DB1 to DB5 can individually, or collectively, access and/or communication with a data access layer 124 such as a remote application server 124. Data access layer/remote application server 124 can be configured to be customer specific/customer developed and comprise, as a non-limiting example, predictive analytics, data processing and data correlation.

The data access layer/remote application server 124 can individually, or collectively, access and/or communication with a front end layer (remote Output Server) 125 such as a graphical user interface (web dashboard). In one embodiment, the front end layer/graphical user interface/remote Output Server 125 includes as a non-limiting example, a Client ERP system 133 that can access and/or communication with maintenance work orders, business metrics, etc., 139. The front end layer/graphical user interface 125 can further include Dashboard (website) 134; best practices, statistical output 138; Dashboard (mobile) 135; documents 137; and reports 136.

Fluid Monitoring and Management Methods

Using the inventive fluid monitoring and management device 10 and system 120 described previously throughout this document, the following various inventive, and non-limiting, fluid monitoring and management methods can be implemented and are now described.

Figure 15A:
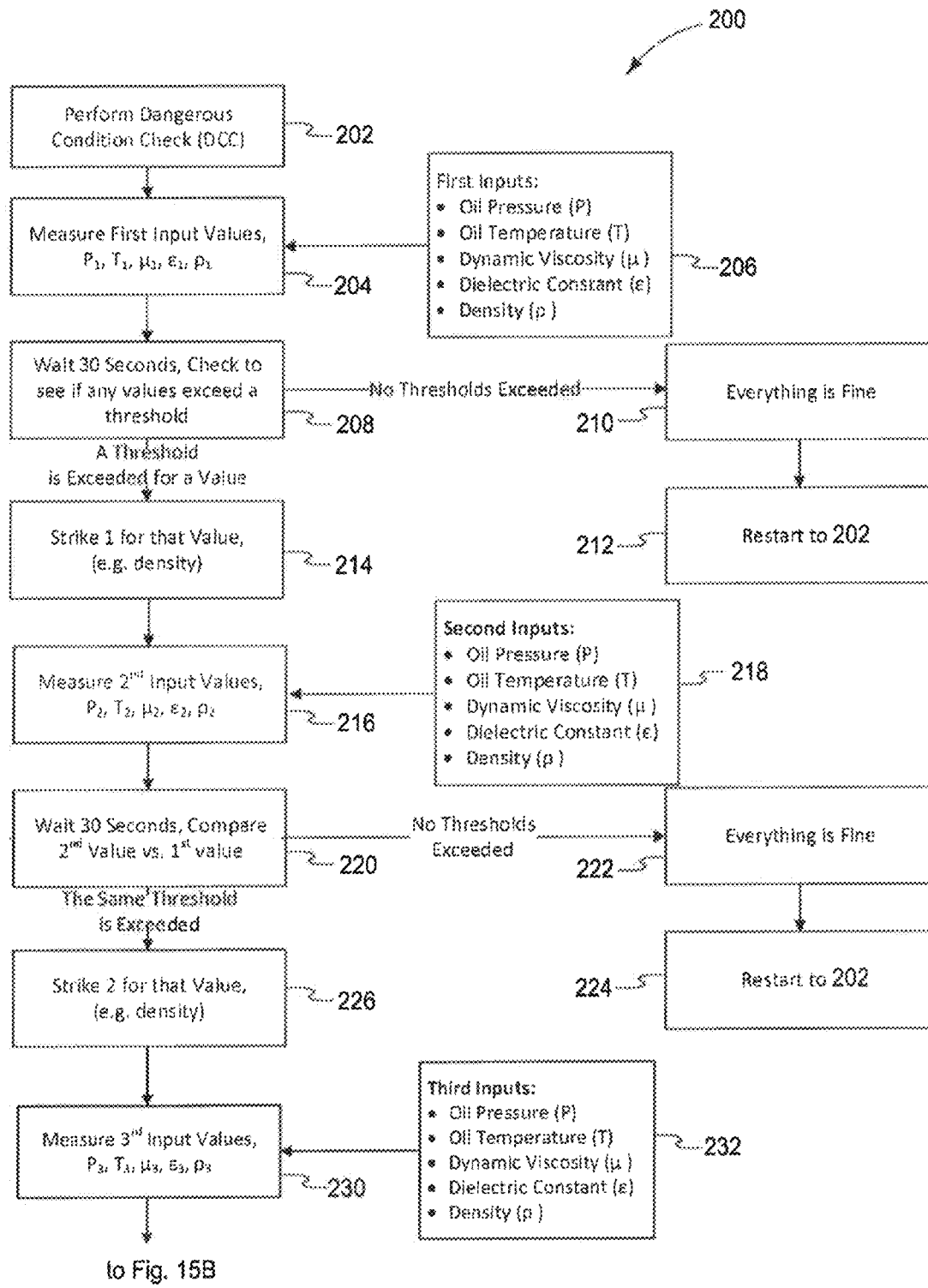
FIGS. 15A-15B are flow charts of various exemplary fluid monitoring and management methods according to various embodiments of the invention and using the fluid monitoring and management device/system of FIGS. 1-14.
Figure 15B:
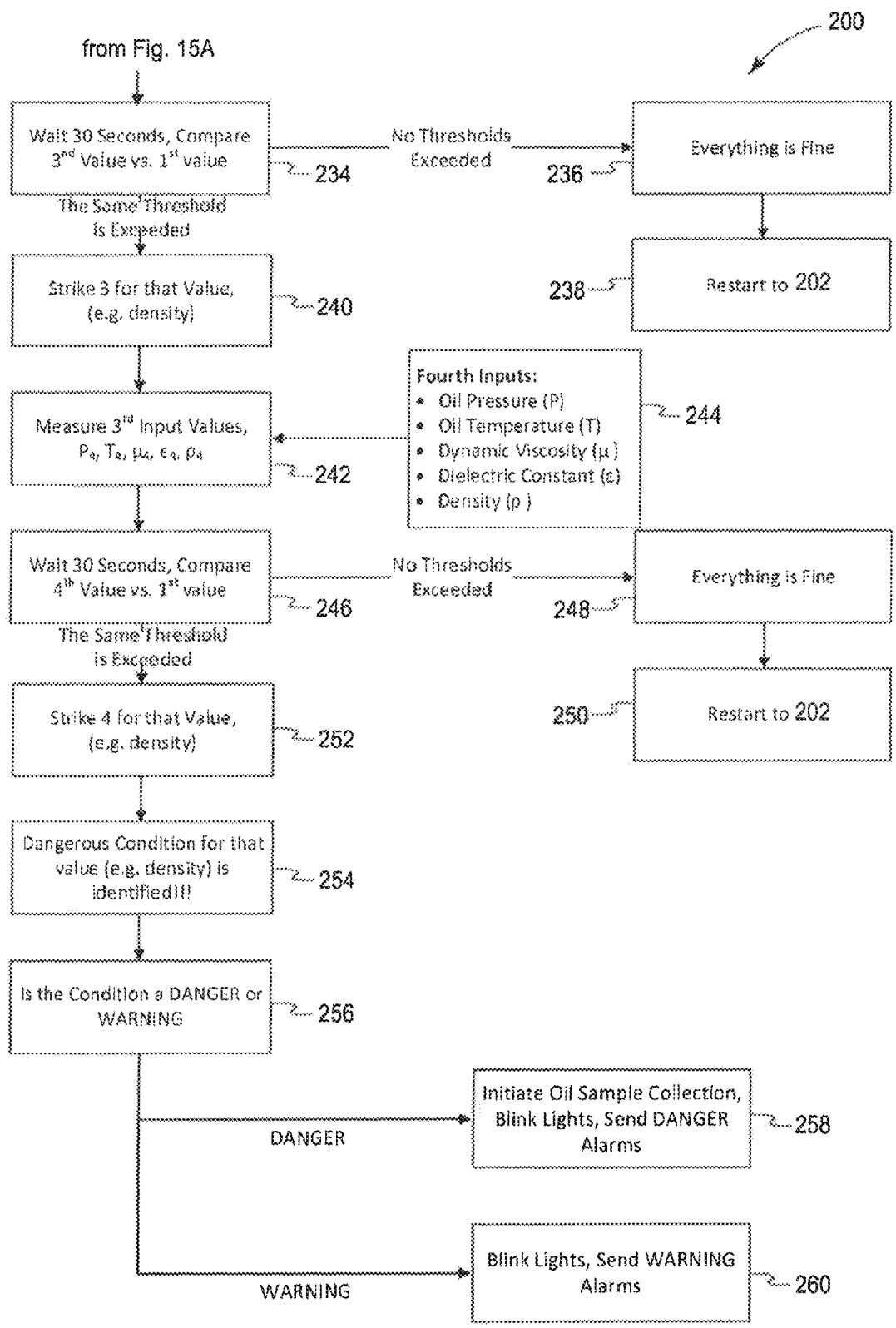

An exemplary one non-limiting fluid method 200 includes Performing a Dangerous Condition Check 200. Referring to FIGS. 15A and 15B, the fluid device/system 10/120 can identify harmful lubricant conditions or machine failures. Performing a Dangerous Condition Check 200 includes the following method steps:

Method step 202: The fluid device/system 10/120 performs a "dangerous condition" check every thirty seconds in order to determine if a sensor input has reached (and surpassed) a threshold value.

Method step 204: The fluid property sensor 70 installed in situ within the fluid device/system 10/120 measures several parameters of the fluid flow and stores the measurement data on a data storage device (e.g. RAM) located on the PCBA 111. This measurement process occurs every 30 seconds.

Method step 206: In situ sensor inputs by Fluid device/system 10/120 include: 1) Fluid Pressure, 2) Fluid Temperature, 3) Dynamic Viscosity of the fluid, 4) Dielectric Constant of the fluid, 5) Density of the fluid.

Method step 208: Upon the FIRST sensor measurement (after 30 seconds have elapsed), measure all fluid property values (method step 206) and compare the values against threshold value settings to see if any of measured values have exceeded the thresholds.

Method step 210: If no threshold value settings are exceeded, there is not likely to be a "Dangerous Condition" present.

Method step 212: Since all measured fluid properties were identified to be within acceptable threshold(s), return to method step 202 and repeat the process again after 30-seconds have elapsed.

Method step 214: If one or more thresholds are exceeded, there is a potential "Dangerous Condition." The Dangerous Condition Process will then assign the FIRST strike to each value that exceeds a threshold.

Method step 216: For the SECOND time, the fluid property sensor 70 installed within the fluid device/system 10/120 measures several parameters of the fluid flow and stores them on a data storage device located on the PCBA 111. This happens every thirty seconds.

Method step 218: perform method step 206.

Method step 220: Upon the SECOND sensor measurement (after 30-seconds have elapsed), measure all fluid property values and compare them against threshold values to see if any of them are still exceeded.

Method step 222: If all measured values are within expected parameters, there is not likely to be a Dangerous Condition present.

Method step 224: Since all measured fluid properties were identified to be within acceptable threshold(s), return to method step 202 and repeat the process again after 30-seconds have elapsed.

Method step 226: If one or more of the SAME thresholds are exceeded for two consecutive cycles, there is a potential Dangerous Condition. The Dangerous Condition Process will then assign a SECOND strike to each value that exceeds a threshold. If one or more new thresholds are exceeded, assign a FIRST strike to those values.

Method step 230: For the THIRD time, the fluid property sensor installed within the fluid device/system 10/120 measures several parameters of the fluid flow and stores them on a data storage device located on the PCBA 111. This happens every thirty seconds.

Method step 232: perform method step 206.

Referring to FIG. 15B, Performing a Dangerous Condition Check 200 continues with the following method steps:

Method step 234: Upon the THIRD sensor measurement (after 30-seconds have elapsed), measure all fluid property values and compare them against threshold values to see if any of them are still exceeded.

Method step 236: If all measured values are within expected parameters, there is not likely to be a Dangerous Condition present.

Method step 238: Since all measured properties were identified to be within acceptable threshold(s), return to method step 202 and repeat the process again after 30-seconds have elapsed.

Method step 240: If one or more of the SAME thresholds are exceeded, there is a potential Dangerous Condition. The Dangerous Condition Process will then assign a THIRD strike to each value that exceeds a threshold. If one or more new thresholds are exceeded, assign a FIRST strike to those values.

Method step 242: For the FOURTH time, the fluid property sensor 70 installed within the fluid device/system 10/120 measures several parameters of the fluid flow and stores them on a data storage device located on the PCBA 111. This happens every thirty seconds.

Method step 244: Fluid device/system 10/120 sensor inputs include: 1) Fluid Pressure, 2) Fluid Temperature, 3) Dynamic Viscosity of the fluid, 4) Dielectric Constant of the fluid, 5) Density of the fluid.

Method step 246: Upon the FOURTH sensor measurement (after 30-seconds have elapsed), measure all fluid property values and compare them against threshold values to see if any of them are still exceeded.

Method step 248: repeat method step 236.

Method step 250: repeat method step 238.

Method step 252: If one or more of the SAME thresholds are exceeded, there is a potential Dangerous Condition. The Dangerous Condition Process will then assign a FOURTH strike to each value that exceeds a threshold. If one or more new thresholds are exceeded, assign a FIRST strike to those values.

Method step 254: All values with thresholds that have been exceeded for FOUR consecutive times (FOUR strikes) measured over four (4) consecutive 30-second cycles (total elapsed time of two (2) minutes) are taken to be indicators of the presence of one or more Dangerous Conditions, one for each threshold exceeded.

Method step 256: Utilize the threshold definitions stored on the fluid device/system 10/120 to determine if each Dangerous Condition is representative of a WARNING Condition (Less Severe) or a DANGER Condition (More Severe).

Method step 258: If there is a DANGER Condition present, initiate an "exception-based," autonomous oil sample collection event, blink appropriate SmartOil system status indicator light(s), and send DANGER alarm notifications (that is, SMS (short message service) text message, email, auto-attendant phone call(s), etc.).

Method step 260: If there is a WARNING Condition present, blink appropriate fluid device/system 10/120 status indicator light(s), and send WARNING alarms (i.e. SMS text message, email, auto-attendant phone call(s), etc.).

Figure 16:
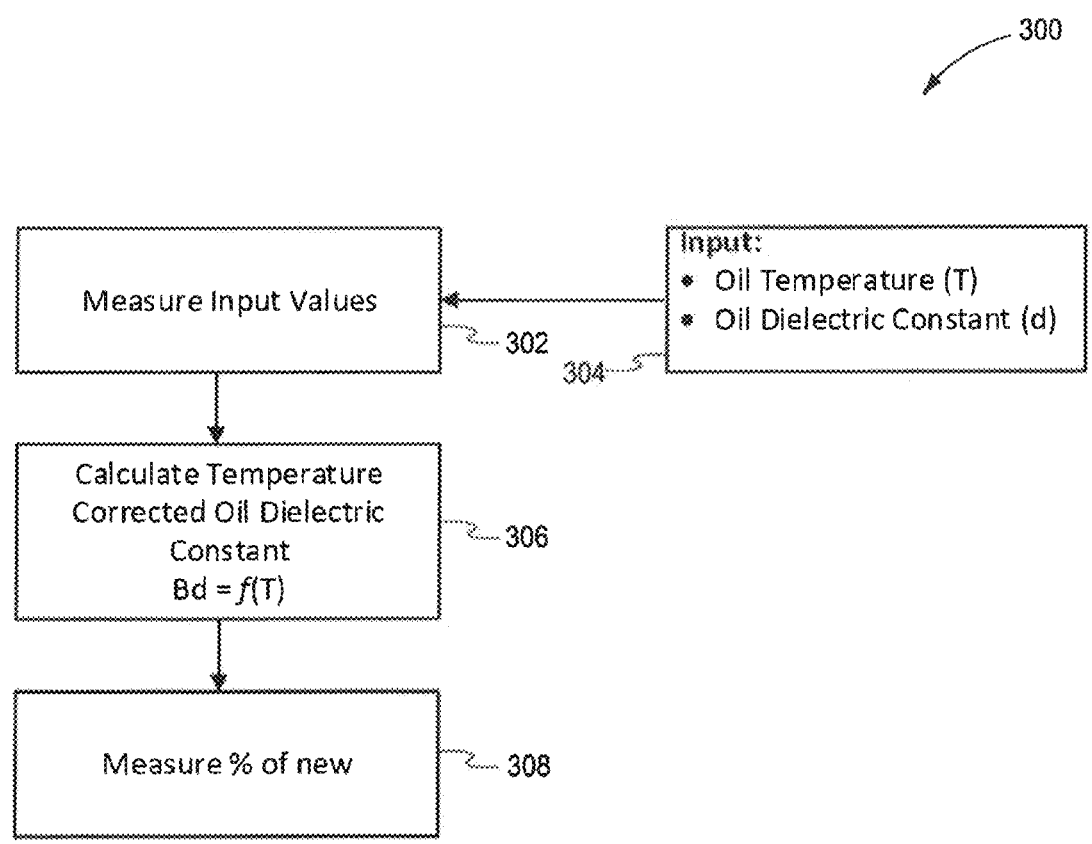
FIGS. 16-22 are flow charts of various exemplary fluid monitoring and management methods according to various embodiments of the invention and using the fluid monitoring and management device/system of FIGS. 1-14.

Referring to FIG. 16, another exemplary non-limiting fluid method 300 includes Temperature Correcting Oil Dielectric Constant Measurements 300. The fluid device/system 10/120 is capable of eliminating the effects of temperature changes to dielectric constant measurements and determining the real departure of an oil's dielectric constant from the oil's baseline (virgin) dielectric constant. Performing a Temperature Correcting Oil Dielectric Constant Measurements 300 includes the following method steps:

Method step 302: The fluid device/system 10/120 utilizes the in situ fluid property sensor 70 to measure the Temperature and Dielectric Constant of the fluid every 30-seconds.

Method step 304: The fluid property sensor 70 inputs include: 1) Fluid Temperature, 2) Dielectric Constant of the fluid.

Method step 306: The fluid device/system 10/120 applies the mathematical function for temperature correction of dielectric constant, where the inputs are defined in method step 304. This function is specifically derived in the laboratory for a given manufacturer, SAE grade, and/or formulation of hydrocarbon based lubricant. Bd=Baseline Dielectric Constant; T=Oil Temperature in degrees Celsius; Bd=exp(0.8226736+(−6.1007466×1e−6×T×T)).

Method step 308: The fluid device/system 10/120 system is able to produce the temperature corrected dielectric constant in terms of "% OF NEW," thereby allowing for the identification of harmful oil property changes, thus providing the operator with Actionable Information in order to make informed decisions and take appropriate corrective action, if deemed necessary.

Figure 17:
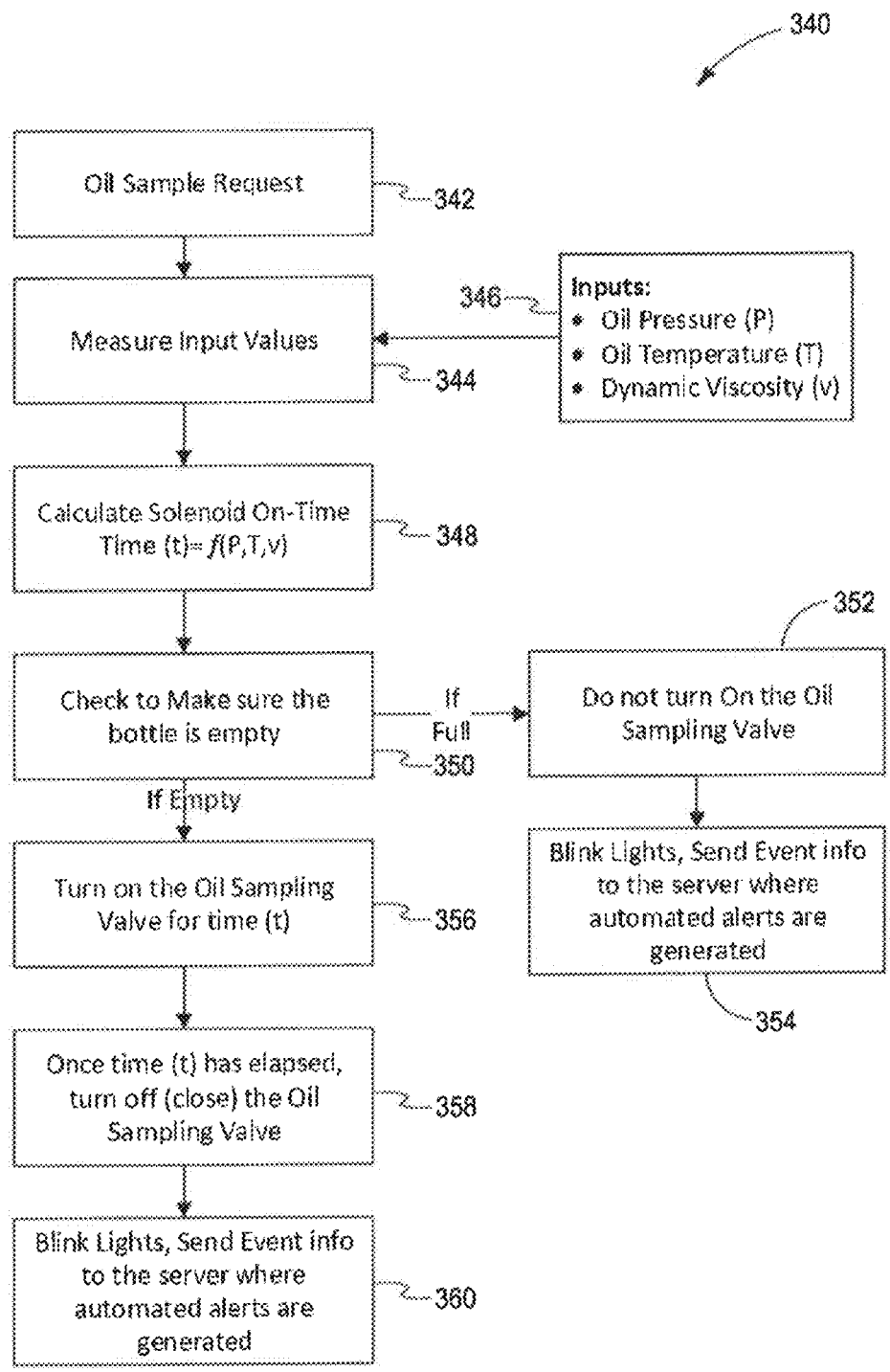

Referring to FIG. 17, another exemplary non-limiting fluid method 340 includes Performing an Oil Sample Collection (Oil Sample Bottle Fill Event) 340. The fluid device/system 10/120 is able to use this process to precisely and repeatably fill an Oil Sample Bottle 34 for subsequent Laboratory Analysis. Performing a Oil Sample Collection 340 includes the following method steps:

Method step 342: performing a request for an Oil Sample Collect Event.

Method step 344: The fluid device/system 10/120 utilizes on-board in situ sensors 70 to measure the Pressure, Temperature and Viscosity of the fluid.

Method step 346: Fluid device/system 10/120 sensor inputs include: 1) Fluid Pressure; 2) Fluid Temperature; and 3) Viscosity of the fluid.

Method step 348: The fluid device/system 10/120 applies the mathematical function for calculation of Solenoid 19 Valve On-Time, where the inputs are defined in method step 346. This function is specifically derived in the laboratory for a given SAE Grade and/or formulation of hydrocarbon based lubricant.

Method step 350: The fluid device/system 10/120 performs a system check to ensure that the Oil Sample bottle 34 is empty.

Method step 352: If the Oil Sample Bottle 34 is not empty, do not turn on the Solenoid 19 Oil Sampling Valve.

Method step 354: Instead, blink applicable fluid device/system 10/120 status light(s) 49 and/or 69, send the sampling event information to the Remote Data Server 123 (FIG. 14B) where the appropriate alerts and notifications are generated. In the case of a ROUTINE sampling event (as opposed to EXCEPTION or MANUAL), wait to perform the oil sample collection until the sample bottle 34 has been retrieved and an empty sample bottle 34 is put in its place.

Method step 356: The solenoid 19 Oil Sampling Valve is turned on (Opened) for the Solenoid 19 Valve On-Time calculated in method step 348. This allows oil to flow to be diverted from the recirculating oil flow path into the Oil Sample Bottle 34, and filling the bottle 34 with the precise fluid volume per the bottle configuration programmed into the fluid device/system 10/120 microprocessor firmware.

Method step 358: Once the Solenoid 19 Valve On-Time value has elapsed, the Solenoid 19 Oil Sampling Valve is turned off (Closed) to stop the diverted flow of oil into the Oil Sample Bottle 34.

Method step 360: Blink applicable Solenoid 19 status light(s) 49 and/or 69, send the sampling event information to the remote data server 123 where the appropriate alerts and notifications are generated (i.e. SMS text message, email, auto-attendant phone call(s), etc.).

Figure 18:
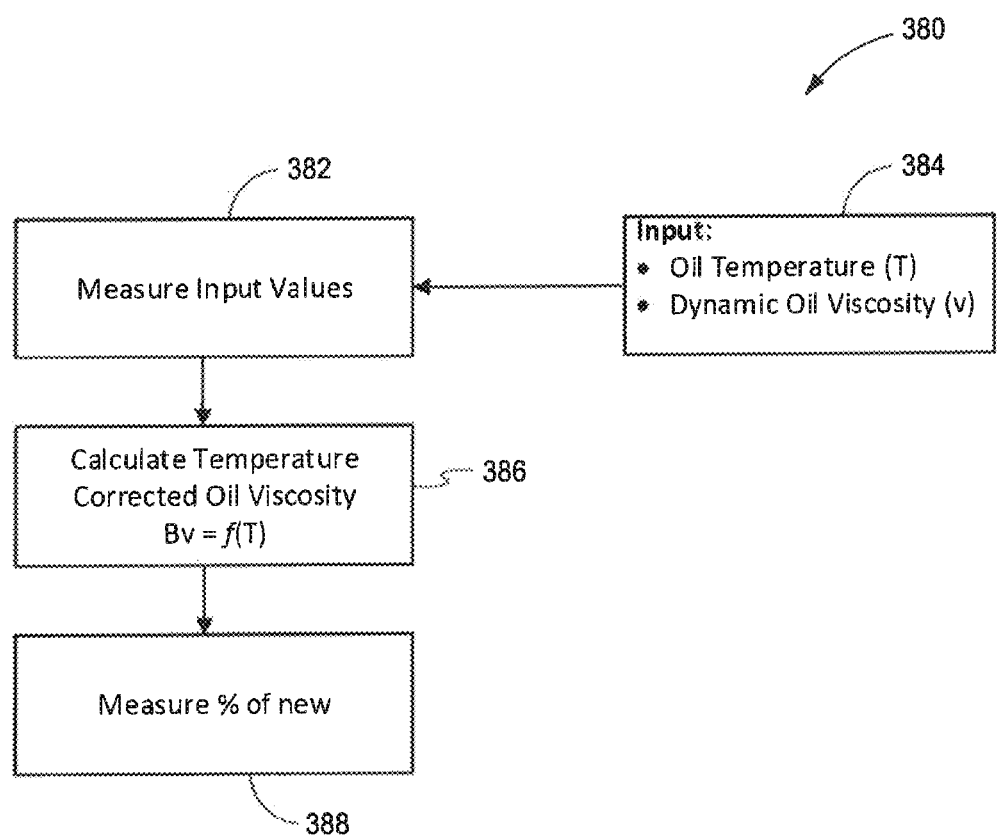

Referring to FIG. 18, another exemplary non-limiting fluid method 380 includes Temperature Correcting Oil Viscosity Measurements 380. Enabling the fluid device/system 10/120 to eliminate the effects of temperature changes and determine the real departure of an oil's viscosity from the oil's baseline (virgin) viscosity. Performing a Temperature Correcting Oil Viscosity Measurements 380 includes the following method steps:

Method step 382: The fluid device/system 10/120 utilizes the in situ fluid property sensor 70 to measure the Temperature and Viscosity of the fluid every 30-seconds.

Method step 384: Fluid device/system 10/120 inputs include: 1) Fluid Temperature; and 2) Viscosity of the fluid.

Method step 386: The fluid device/system 10/120 applies the mathematical function for temperature correction of viscosity, where the inputs are defined in method step 384. This function is specifically derived in the laboratory for a given manufacturer, SAE grade, and/or formulation of hydrocarbon based lubricant. Bv=Baseline Viscosity; T=Oil Temperature in degrees Celsius; Bv=(1.5763649+ (17018.976/(T×T))^2)). Please refer to the above the section entitled: *Proprietary Algorithm for Real-Time Temperature Correction of Engine Oil Viscosity* for additional support and disclosure.

Method step 388: The fluid device/system 10/120 is able to produce the temperature corrected viscosity for the oil in terms of "% OF NEW," thereby allowing for the identification of harmful oil property changes, thus providing the operator with Actionable Information in order to make informed decisions and take appropriate corrective action, if deemed necessary.

Figure 19:
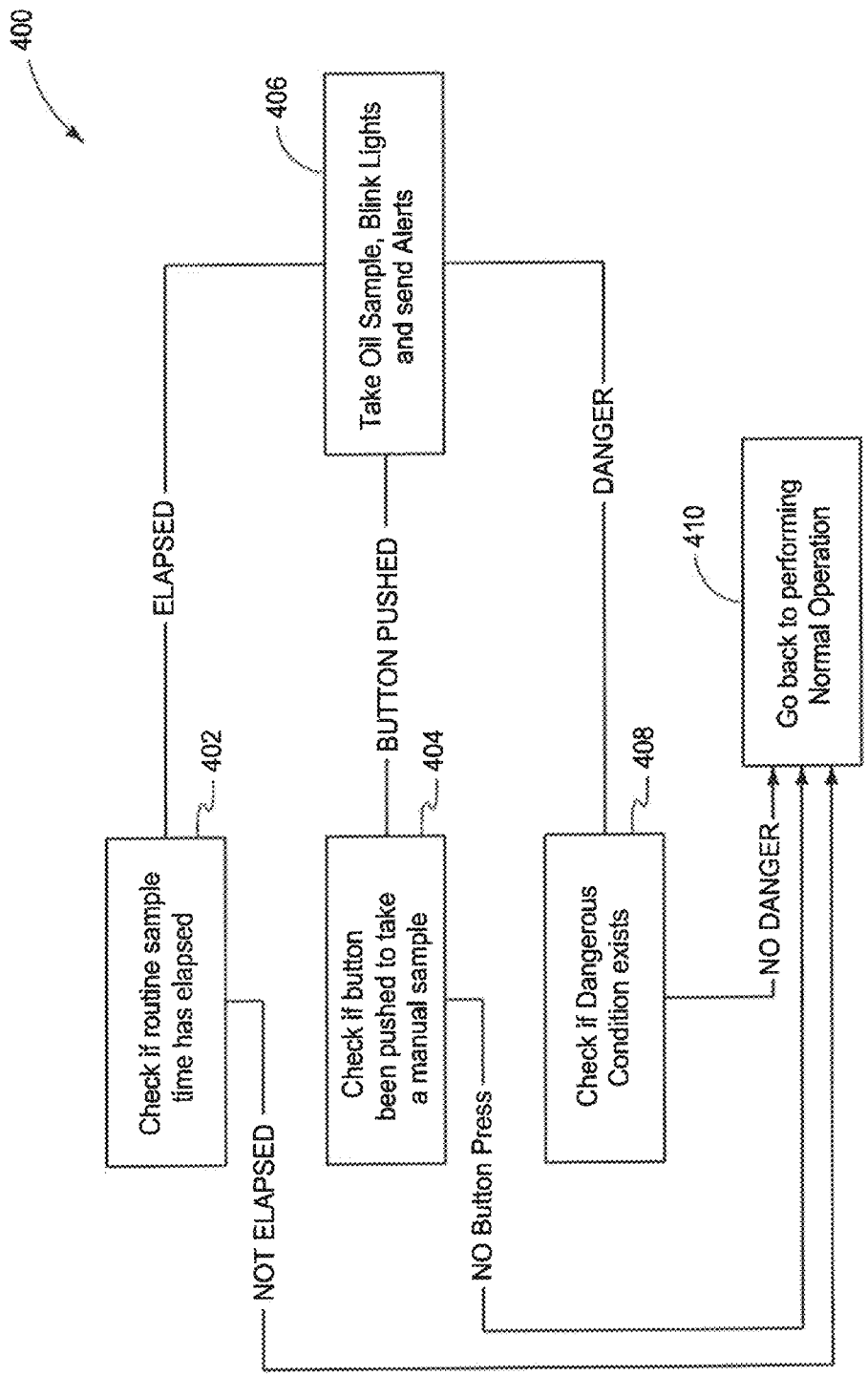

Referring to FIG. 19, another exemplary non-limiting fluid method 400 includes Triggering an Oil Sample Collect 400. The Oil Sample Events can be triggered in one of three ways, these include: 1) MANUAL SAMPLE—manually performed by a mechanic/operator (human), 2) ROUTINE SAMPLE—automatically triggered by the fluid device/system 10/120 firmware (machine time schedule-based), 3) SAMPLE-BY-EXCEPTION—automatically triggered by the fluid device/system 10/120 firmware (Dangerous Condition exception-based). Performing Triggering an Oil Sample Collect 400 includes the following method steps:

Method step 402: The fluid device/system 10/120 counts the machine's operating time in hours and is able to trigger a ROUTINE oil sample collection event based on a pre-set (user configurable) interval of machine operating hours. This ensures that Oil Samples are collected consistently and regularly based on the machine's operation. Every time the configurable machine hour interval elapses, the fluid device/system 10/120 performs an Oil Sample Collect Event and the interval is re-set, starting the countdown over again.

Method step 404: If the fluid device/system 10/120 RESET/SAMPLE button 91 is pressed, a MANUAL (human triggered) Oil Sample Collection Event can be performed. This enables the user of the fluid device/system 10/120 to collect a sample of oil upon demand, or at will.

Method step 406: Any of the three (3) fluid device/system 10/120 Sampling Trigger methods (Manual vs. Routine vs. Exception-Based) causes the Sample Collection process to be activated, this method/process is described in fluid method 340 shown in FIG. 17.

Method step 408: If the Dangerous Condition Method/Process (described in FIG. 15A, 15B as fluid method 200) identifies the presence of a DANGEROUS CONDITION, the Oil Sample Collection process is triggered automatically (e.g. Exception-Based method), generating a Sample-by-Exception oil sample.

Method step 410: If none of the conditions required to trigger a Oil Sample Collection process are present, the fluid device/system 10/120 will continue its normal operations by default.

Figure 20:
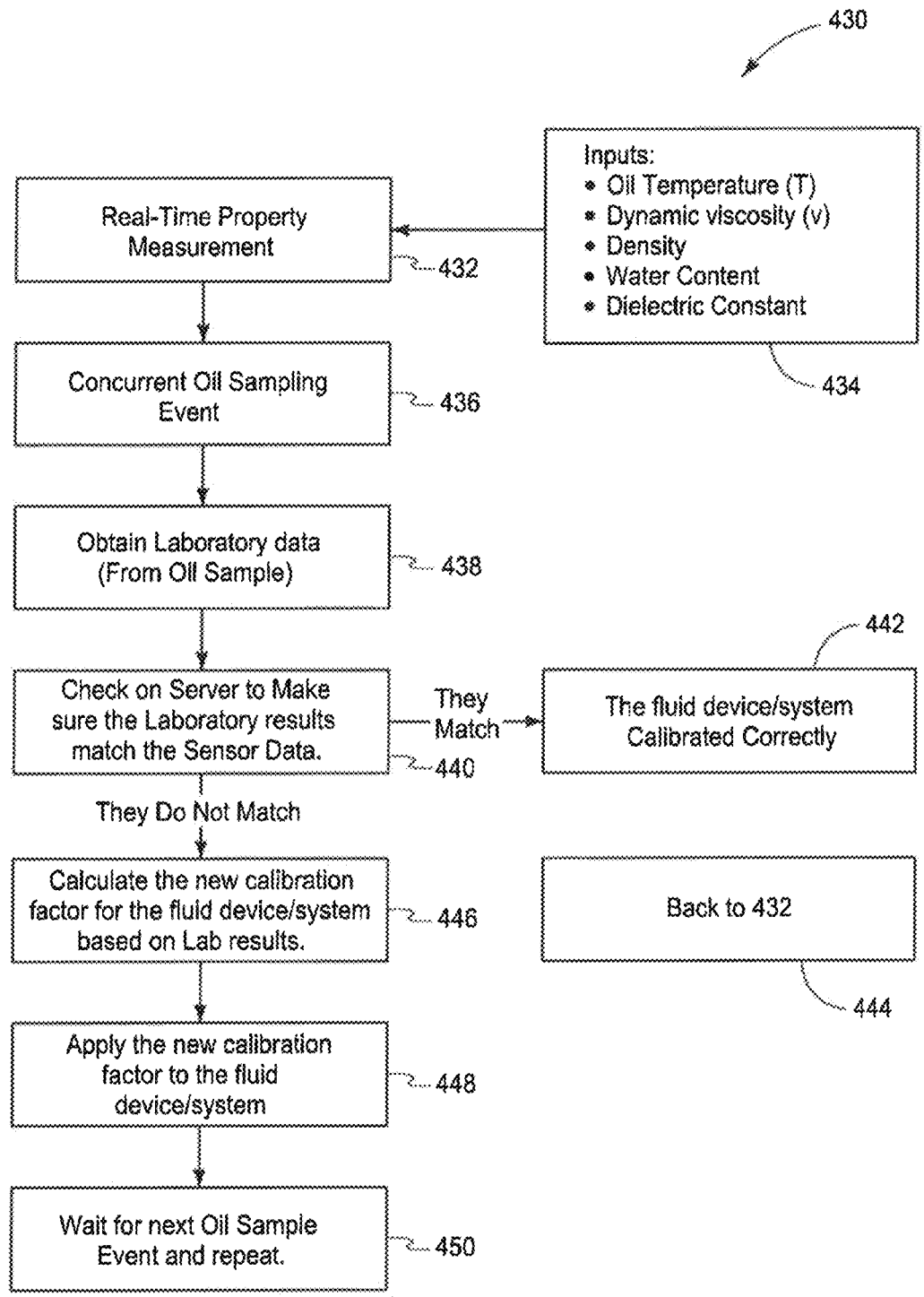

Referring to FIG. 20, another exemplary non-limiting fluid method 430 includes Auto-Calibration of fluid device/system 10/120 Sensor Measurements 430. Auto-Calibration of Sensor Measurements; The unique combination of Real-Time Sensor Data and High-Quality Laboratory Analysis allows the fluid device/system 10/120 sensors to be automatically calibrated if or when the need arises. Performing Auto-Calibration of fluid device/system 10/120 Sensor Measurements 430 includes the following method steps:

Method step 432: The fluid property sensor 70 installed within the fluid device/system 10/120 measures several parameters of the fluid flow and stores the measurement values to data storage device (i.e. RAM, ROM, Flash memory) located on the PCBA 111. The data is also transmitted to the remote Data Server 123 (FIG. 14B) via the internet.

Method step 434: Fluid device/system 10/120 sensor inputs include: 1) Density of the Fluid, 2) Fluid Temperature, 3) Dynamic Viscosity of the fluid, 4) Dielectric Constant of the fluid, 5) Water Content of the fluid.

Method step 436: The fluid device/system 10/120 performs an Oil Sampling event and makes a sensor measurement at the same time the sensor data is sent up to the remote Data Server 123. The Oil that is collected in the Oil Sample Bottle 34 is representative of the previously mentioned sensor measurements. Theoretically, the laboratory analysis results and the fluid device/system 10/120 sensor data values should agree very closely.

Method step 438: The Oil Sample bottle 34 is shipped to the oil analysis laboratory where the oil in the bottle is analyzed and the oil analysis data is sent to the remote Data Server 123.

Method step 440: On the remote Application Server 124 (FIG. 14B), the lab analysis data (method step 438) and the concurrent sensor data (method step 436) are compared against each other.

Method step 442: If the lab analysis data and the fluid device/system 10/120 sensor data agree closely with each other, it can be said that the fluid device/system 10/120 sensors are calibrated correctly and there is no need for calibration.

Method step 444: In the case that there is no need for calibration, the process is repeated at the time of the next ROUTINE oil sample collection event.

Method step 446: If the lab analysis data and the fluid device/system 10/120 sensor data do NOT agree closely with each other, it can be said that the fluid device/system 10/120 sensors are not calibrated correctly and there is a need to calibrate the fluid device/system 10/120 sensors. The remote Application Server 124 calculates the appropriate calibration factor(s) for each affected fluid device/system 10/120 sensor based on the discrepancy between the laboratory analysis results and the concurrent sensor data.

Method step 448: The calibration factor(s) calculated on the remote Application Server 124 are automatically sent from the remote Output Server 125 (FIG. 14B) to the fluid device 10 via its wireless data link in order to appropriately calibrate the fluid device/system 10/120 sensors.

Method step 450: Now that the fluid device/system 10/120 has been auto-calibrated correctly, the Auto-Calibration process is repeated at the time of the next ROUTINE oil sample collection event.

Figure 21:
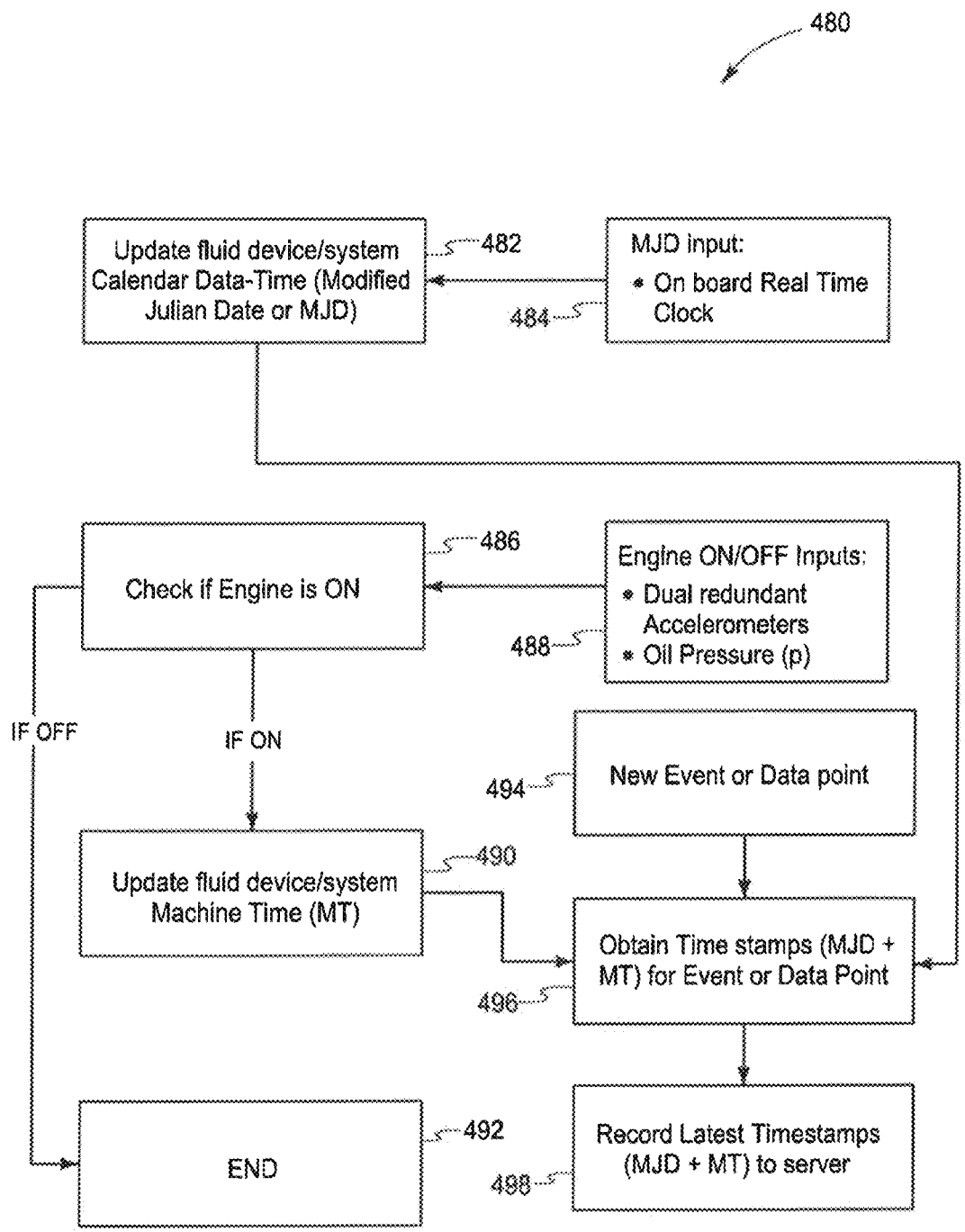

Referring to FIG. 21, another exemplary non-limiting fluid method 480 includes a method/Process for the Application of Dual Timestamps to all recorded fluid device/system 10/120 Functions 480. This enables sensor data, alerts, alarms, and events to be time-stamped according to two distinct and important measurements of time: 1) Calendar time, or Modified Julian Date (MJD), tracks the actual date/time of an event or sensor measurement; 2) Machine time (MT) tracks the time of an event or sensor measurement with respect to the machine's life history. The fluid device/system 10/120 is able to track MT and only increment the MT counter if the machine is operating. This enables the possibility of viewing fluid device/system 10/120 events, sensor data, or Laboratory data with respect to the machine's operating history. Performing a method/Process for the Application of Dual Timestamps to all recorded fluid device/system 10/120 Functions 480 includes the following method steps:

Method step 482: The fluid device/system 10/120 constantly updates the time values stored in its microprocessor with a clock device (real-time-clock) that is mounted on the motherboard, for example, main printed circuit board 111.

Method step 484: The fluid device/system 10/120 has an on-board real-time-clock (clock device) that precisely keeps track of the MJD timestamp (e.g. 2015-08-25 2:45:26 PM). The real-time-clock is automatically synchronized with a world time server on a regular interval. This synchronization is performed at period intervals (configurable and programmed in the microprocessor firmware) via a data link between the fluid device/system 10/120 and the internet. Due to the fluid device/system 10/120 operating in a hot environment as it is directly mounted to an internal combustion engine or a compressor, the real-time-clock synchronization interval is set to an hourly schedule.

Method step 486: The fluid device/system 10/120 utilizes sensor input to determine if the machine is in operation or not.

Method step 488: Inputs to method step 486 are redundant accelerometers and oil pressure, if oil pressure is not below a threshold, and BOTH accelerometers register vibration, the machine is in operation (ON). If there is no vibration registered (state 1) AND the oil pressure is below a threshold (state 2), the machine is NOT in operation (OFF).

Method step 490: If the machine is registered to be in operation (ON), the fluid device/system 10/120 increments the Machine Time counter.

Method step 492: If the machine is registered to NOT be in operation (OFF), the fluid device/system 10/120 does not increment the Machine Time counter.

Method step 494: Any and all new fluid device/system 10/120 events/data points are generated as a result of normal fluid device/system 10/120 operations.

Method step 496: At the instant of the new event/data point, the fluid device/system 10/120 reads the MJD date/time and the MT counter value and applies both time values to the event or data point in such a way that they correspond.

Method step 498: The new event/data point, now linked to BOTH the MJD and MT timestamps, is sent to the remote Data Server 123 for long term storage, analysis on the remote Application Server 124, and output via the remote Output Server 125.

Figure 22:
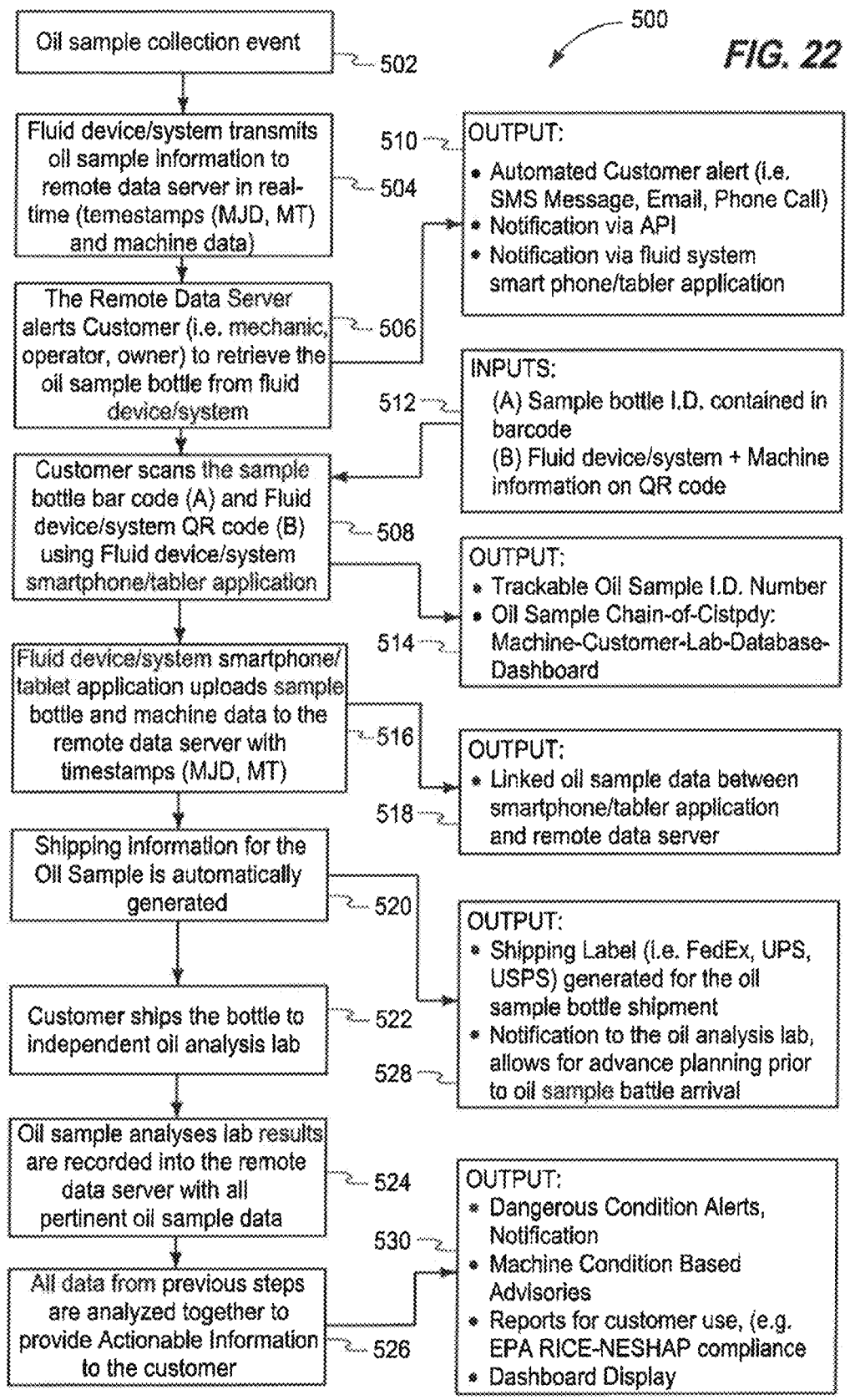

Referring to FIG. 22, another exemplary non-limiting fluid method 500 includes an Oil Sample Collection method/

Process 500. Performing an Oil Sample Collection method/Process 500 includes the following method steps:

Method step 502: Oil sample collection event-solenoid 19 actuated valve opens for a calculated time allowing precise volume of oil to fill the sample collection bottle 34. Sample Collection Event is either manually performed by a mechanic/operator (human), or automatically triggered by the fluid device/system 10/120 firmware (machine-time (MT) schedule-based (fluid method 480; FIG. 21), or Dangerous Condition exception-based (fluid method 200; FIGS. 15A and 15B)).

Method step 504: Immediately upon an oil sample event, the fluid device/system 10/120 transmits a timestamp (machine time (MT), and calendar time (MJD)) of the oil sample collection event (and all other pertinent machine information) to the remote Data Server 123.

Method step 506: Once the fluid device/system 10/120 sends oil sample collection event to the remote Data Server 123, the remote Data Server 123 automatically sends out an email/SMS (short message service) text to client informing of an oil sample collection has just occurred.

Method step 508: The operator/mechanic (human) who is dispatched to the equipment-mounted fluid device/system 10/120 retrieves the FILLED oil sample bottle 34. Prior to removing the bottle from the fluid device/system 10/120, the person uses a smartphone/tablet equipped with scanning application and manually scans two (2) labels: 1) the bar code label that is on the oil sample bottle, and 2) the QR code that is affixed to the fluid device/system 10/120 housing 18 (located on inner door 24 surface of enclosure).

Method step 510: Various forms of client-facing Actionable Information communications may include: SMS text messages, email messages, real-time web-based dashboard, auto-attendant phone calls, etc.

Method step 512: Input-Sample of bar code (affixed to oil sample bottle 34) and QR code (affixed to fluid device 10).

Method step 514: Output-Trackable oil sample I.D. number. Oil sample chain-of-custody: machine-customer-lab-database-dashboard.

Method step 516: Once the scanned bar/QR code data has been collected, the smartphone/tablet wirelessly transmits the data to the oil analysis laboratory via the remote Data Server 123.

Method step 518: The scanned bar/QR code information for the specific oil sample and machine is linked to a lab analysis I.D. record in the lab's database.

Method step 520: Shipping information is gathered for shipment of oil sample bottle 34 to oil analysis lab; shipping charges are applied and postage is charged to client account.

Method step 522: After the client has retrieved the oil sample bottle 34, the sample is packaged by the client and shipped to the oil analysis lab for a detailed oil analysis per ASTM-based protocol.

Method step 524: Oil lab analysis results are automatically uploaded from the lab database to the remote Data Server 123 via a developed API. API=Application Programming Interface. (method step 548 of FIG. 23).

Method step 526: Alert notifications are sent to client (i.e., SMS text, email, auto-attendant phone call(s)) informing the client of the fluid device/system 10/120-monitored equipment system status from which the client can choose to take further action (or not).

Method step 528: Shipping label file is generated for shipment of oil sample bottle 34 to oil analysis lab; shipping charges are applied and postage is charged to client account.

Method Step 530: Various forms of client-facing Actionable Information communications may include: SMS text messages, email messages, real-time web-based dashboard, auto-attendant phone calls, etc.

Figure 23:
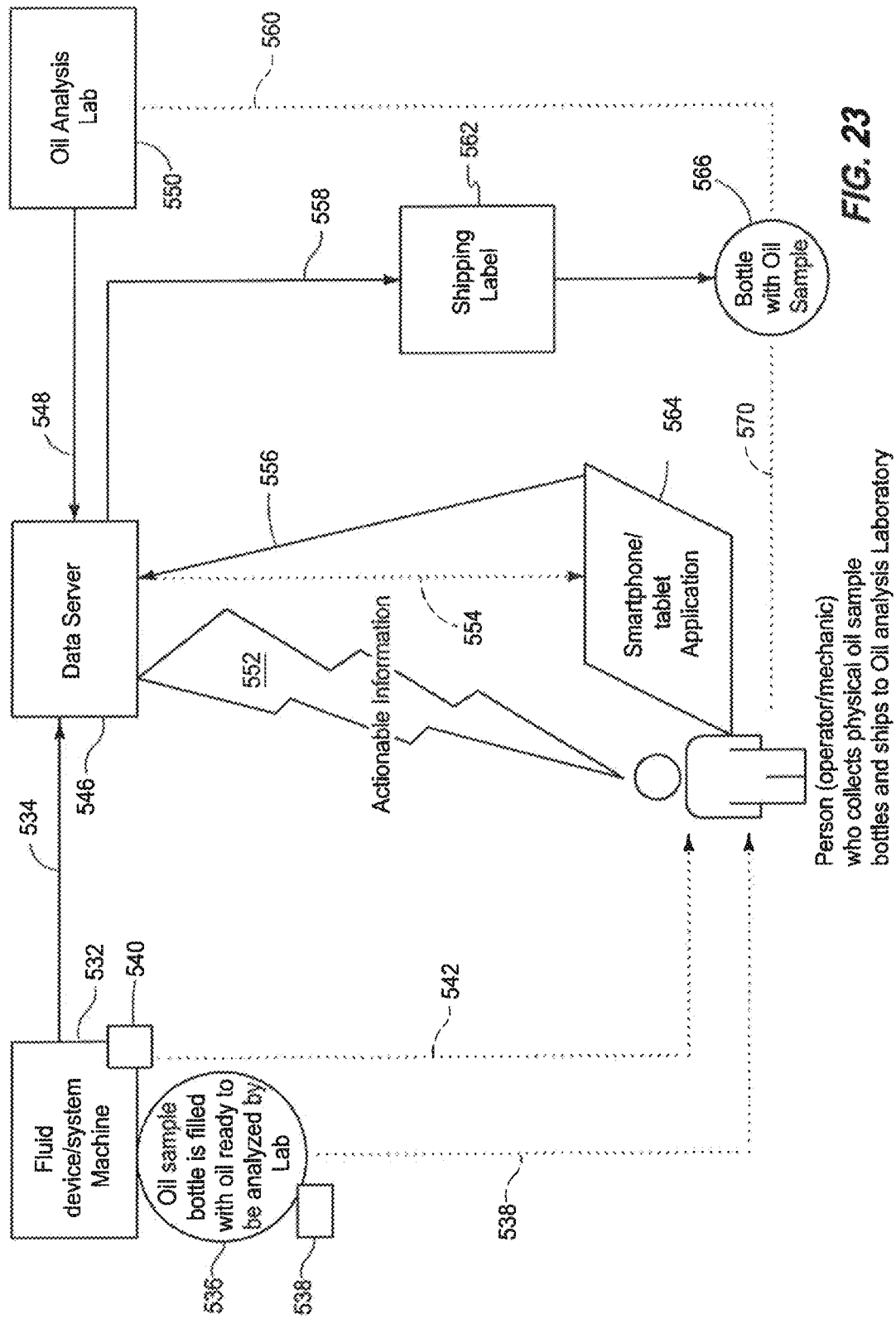
FIG. 23 is a schematic view of the exemplary fluid monitoring and management method of FIG. 22.

Referring to FIG. 23, a diagram to further illustrate fluid method 500 of FIG. 22 for an Oil Sample Collection method/Process. This diagram includes the following reference numerals:

532: a fluid device/system 10/120 had been provided on a machine/equipment (method step 502 of FIG. 22).

534: Data transmission is performed from fluid device/system 10/120 to remote Data Server 123 (method step 504 of FIG. 22).

536: Oil Sample Bottle 34 is filled with oil ready to be analyzed by Laboratory.

538: Bar code containing unique serial number, affixed to oil sample bottle 34 (method steps 512, 514 of FIG. 22).

540: QR code containing unique machine I.D. information (method steps 512, 514 of FIG. 22).

542: Operator retrieves FILLED oil sample bottle from fluid device/system 10/120 (method step 508 of FIG. 22).

544: Person (operator, mechanic) who collects physical oil sample bottles 34 and ships to Oil Analysis Laboratory.

546: Remote Data Server 123.

548: Oil analysis test results is data wirelessly transmitted to remote Data Server (method step 524 of FIG. 22).

550: Oil Analysis Laboratory where physical oil sample bottles are shipped and analyzed.

552: Actionable Information (method step 524 of FIG. 22).

554: Wireless data link between remote Data Server 123 and smartphone/tablet application (method step 506 of FIG. 22).

556: Bar/QR code data scanned by the smartphone/tablet Scanning App and wirelessly transmitted to Data Server 123 (method steps 516, 518 of FIG. 22).

558: Shipping label file generated by remote Application Server 124 and wirelessly transmitted to customer for local printing and affixing to shipment of physical oil sample bottle 34 (method step 536 of FIG. 22) to Oil Analysis Laboratory (method steps 550, 520 of FIG. 22).

560: Physical Oil Sample Bottle 34 shipped to Oil Analysis Laboratory utilizing generated Shipping Label (method step 522 of FIG. 22).

562: Custom shipping label for physical oil sample bottle 34 (method step 536 of FIG. 22).

564: Smartphone/Tablet Application used for scanning bar/QR codes and wirelessly transmitting to Oil Analysis Laboratory.

566: Physical oil sample bottle 34 with bar code label affixed (method step 514 of FIG. 22).

570: Bottle I.D. and timestamp data wirelessly transmitted to Oil Analysis Laboratory (method step 522 of FIG. 22).

In compliance with the statute, the various embodiments have been described in language more or less specific as to structural and methodical features. It is to be understood, however, that the various embodiments are not limited to the specific features shown and described, since the means herein disclosed comprise disclosures of putting the various embodiments into effect. The various embodiments are, therefore, claimed in any of its forms or modifications within the proper scope of the appended claims appropriately interpreted in accordance with the doctrine of equivalents.

What is claimed is:

1. A fluid monitoring and management method comprising:

measuring temperature of a fluid in a fluid system having a sensor and obtaining a first temperature value;

measuring viscosity of the fluid and obtaining a first viscosity value;

calculating a first temperature-corrected viscosity value utilizing the first viscosity value and the first temperature value;

determining if the first temperature-corrected viscosity value is outside a preselected range of threshold values;

if the determining is yes, automatically collecting a sample of the fluid by extracting the fluid in to one of a plurality of bottles in a housing while simultaneously performing the following steps:
i) measuring a second temperature of the fluid;
ii) measuring a second viscosity of the fluid;
iii) calculating a second temperature-corrected viscosity value of the fluid;
iv) storing data comprising the second temperature, the second viscosity value, and the second temperature-corrected viscosity value;
v) creating a sample bottle identification code which associates the data with the one of the plurality of bottles;
vi) automatically stamping the one of the plurality of bottles with a timestamp and the sample bottle identification code; and
vii) generating an alert notification.

2. The method of claim 1 further comprising determining a departure of the viscosity of the fluid from a virgin (baseline) value for viscosity of the fluid based on the first temperature-corrected viscosity value.

3. The method of claim 1 further comprising:
determining a departure of the viscosity of the fluid from a virgin (baseline) value for viscosity of the fluid utilizing the first temperature-corrected viscosity value; and
presenting the departure determination as a percentage difference.

4. The method of claim 3 further comprising comparing the percentage difference to a range of threshold percentage values.

5. The method of claim 1 wherein the fluid comprises oil.

6. The method of claim 1, further comprising: measuring the viscosity of the fluid and obtaining a third viscosity value, comparing the first and third viscosity values, and during the comparing, removing an influence of fluid temperature.

7. The method of claim 6 wherein the comparing is a first comparing step and comprises obtaining a fourth viscosity value, and further comprising a second comparing step comprising comparing the fourth viscosity value to a viscosity value baseline value.

8. The method of claim 1 further comprising providing a capability to calculate a relative viscosity change of two dissimilar fluids when calculating their relative viscosity changes in terms of a percent departure from a respective baseline value of each fluid.

9. The method of claim 1 further comprising:
evaluating a remaining useful life (RUL) of the fluid by calculating temperature-corrected viscosity values of the fluid over time; and
deriving a time rate of departure from a respective baseline value.

10. The method of claim 1 further comprising:
comparing a performance of a plurality of fluids by determining their temperature-corrected viscosities; and
comparing their respective departures from viscosity baseline values over time.

11. The method of claim 1, wherein the timestamp comprises one of: Greenwich Mean Time and machine time comprising actual accumulated operational time of the fluid system.

12. The method of claim 1 wherein the one of the bottles comprises a volume of at least four ounces.

13. The method of claim 1, wherein the timestamp comprises one of: a modified Julian date (MJD) and equipment operating lifetime.

14. The method of claim 1, wherein the alert notification is a text message or email.

15. The method of claim 1 further comprising, before the collecting of the sample, performing a system check to ensure that the one of the plurality of bottles is empty.

16. The method of claim 1 wherein the collecting of the sample comprises operating a solenoid-actuated valve.

17. The method of claim 1 wherein the housing encloses a microprocessor and the sensor.

18. The method of claim 1 wherein the housing encloses a microprocessor, the sensor and a user interface panel.

19. The method of claim 18 wherein the user interface panel comprises a removable flash data storage key.

20. The method of claim 1 wherein the housing encloses a microprocessor, the sensor and a solenoid.

21. The method of claim 1 further comprising providing a fluid passageway through the housing.

22. A fluid monitoring and management method comprising:
measuring temperature of a fluid in a fluid system having a sensor and obtaining a first temperature value;
measuring viscosity of the fluid and obtaining a first viscosity value;
calculating a first temperature-corrected viscosity value utilizing the first viscosity value and the first temperature value;
measuring a first fluid pressure and a first fluid density;
determining if the first temperature-corrected viscosity value and any one of the first fluid pressure, the first temperature value, and the first fluid density are outside a preselected range of threshold values;
if the determining is yes, automatically collecting a sample of the fluid by extracting the fluid in to one of a plurality of bottles in a housing while simultaneously performing the following steps:
i) measuring a second temperature of the fluid;
ii) measuring a second viscosity of the fluid;
iii) calculating a second temperature-corrected viscosity value of the fluid;
iv) measuring a second fluid pressure and a second fluid density;
v) storing data comprising the second temperature, the second viscosity value, the second temperature-corrected viscosity value, the second fluid pressure, and the second fluid density;
vi) creating a sample bottle identification code which associates the data with the one of the plurality of bottles;
vii) automatically stamping the one of the plurality of bottles with a timestamp and the sample bottle identification code; and
viii) generating an alert notification.

23. The method of claim 22, wherein the timestamp comprises one of: Greenwich Mean Time and machine time comprising actual accumulated operational time of the fluid system.

24. The method of claim 22 wherein the one of the plurality of bottles comprises a volume of at least four ounces.

25. The method of claim 22, wherein the timestamp comprises at least one of a modified Julian date (MJD) and equipment operating lifetime.

26. The method of claim 22, wherein the alert notification is a text message or email.

27. The method of claim 22 further comprising, before the collecting of the sample, performing a system check to ensure that the one of the plurality of bottles is empty.

28. The method of claim 22 wherein the collecting of the sample comprises operating a solenoid-actuated valve.

29. The method of claim 22 wherein the housing encloses a microprocessor and the sensor.

30. The method of claim 22 wherein the housing encloses a microprocessor, the sensor and a user interface panel.

31. The method of claim 30 wherein the user interface panel comprises a removable flash data storage key.

32. The method of claim 22 wherein the housing encloses a microprocessor, the sensor and a solenoid.

33. The method of claim 22 further comprising providing a fluid passageway through the housing.

34. A fluid monitoring and management method comprising:
    measuring temperature over a first time period of a fluid in a fluid system having a sensor to obtain a plurality of temperature values;
    measuring viscosity of the fluid over the first time period to obtain a plurality of viscosity values which correspond to the plurality of temperature values;
    calculating curve fit coefficients of a curve fit equation using the plurality of temperature values and the plurality of viscosity values, wherein the curve fit equation is defined as $\mu=(a+bT^2)^2$, $\mu$ is the viscosity of the fluid, T is the temperature of the fluid, and a and b are the curve fit coefficients;
    measuring temperature of the fluid during a second time period to obtain a second temperature value;
    measuring viscosity of the fluid during the second time period to obtain a second viscosity value;
    calculating a first temperature-corrected viscosity value utilizing the second temperature value, the second viscosity value, and the curve fit equation;
    determining if the first temperature-corrected viscosity value is outside a preselected range of threshold values;
    if the determining is yes, automatically collecting a sample of the fluid by extracting the fluid in to one of a plurality of bottles in a housing while simultaneously performing the following steps:
        i) measuring a third temperature of the fluid;
        ii) measuring a third viscosity of the fluid;
        iii) calculating a second temperature-corrected viscosity value of the fluid;
        iv) automatically timestamping the one of the plurality of bottles; and
        v) generating an alert notification.

35. The method of claim 34, further comprising: determining a useful condition of the fluid using temperature-corrected viscosity values calculated using the curve fit equation.

36. The method of claim 34 wherein the curve fit equation was developed from nonlinear regression analysis methods.

37. The method of claim 34 wherein the calculating of the first temperature-corrected viscosity value is used to determine one of the following statuses of the fluid:
    a present/current status; a dangerous condition status and a useable life status.

38. The method of claim 34 wherein the sensor acquires data at a time interval ranging from 5 seconds to 60 seconds.

39. The method of claim 38 wherein the time interval is 30 seconds.

40. The method of claim 34 wherein the measuring of the viscosity of the fluid over the first time period or during the second time period comprises acquiring dynamic viscosity data in centipoise (cP) units.

41. The method of claim 40 wherein the sensor acquires the dynamic viscosity data over a range of 0.5 cP to 50 cP.

* * * * *